United States Patent
Kakitani et al.

(10) Patent No.: US 9,428,560 B2
(45) Date of Patent: Aug. 30, 2016

(54) PROTEIN COMPRISING TRUNCATED FORM OF EXTRACELLULAR REGION PROTEIN OF FRIZZLED 2, AND PHARMACEUTICAL COMPOSITION FOR TREATING BONE DISEASES WHICH COMPRISES SAID PROTEIN

(75) Inventors: Makoto Kakitani, Tokyo (JP); Kengo Yamawaki, Tokyo (JP)

(73) Assignee: KYOWA HAKKO KIRIN CO., LTD, Tokyo (JP)

(*) Notice: Subject to any disclaimer, the term of this patent is extended or adjusted under 35 U.S.C. 154(b) by 151 days.

(21) Appl. No.: 14/127,654

(22) PCT Filed: Jun. 21, 2012

(86) PCT No.: PCT/JP2012/065911
§ 371 (c)(1),
(2), (4) Date: Mar. 18, 2014

(87) PCT Pub. No.: WO2012/176853
PCT Pub. Date: Dec. 27, 2012

(65) Prior Publication Data
US 2014/0199305 A1    Jul. 17, 2014

(30) Foreign Application Priority Data
Jun. 21, 2011    (JP) .................... 2011-137279

(51) Int. Cl.
| A61K 38/16 | (2006.01) |
| C07K 14/00 | (2006.01) |
| C12N 15/62 | (2006.01) |
| C07K 14/435 | (2006.01) |
| C07K 14/71 | (2006.01) |
| A61K 31/711 | (2006.01) |
| A61K 38/00 | (2006.01) |

(52) U.S. Cl.
CPC ........... *C07K 14/435* (2013.01); *A61K 31/711* (2013.01); *C07K 14/71* (2013.01); *A61K 38/00* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| 2011/0237514 A1 | 9/2011 | Kakitani et al. |
| 2013/0230520 A1 | 9/2013 | Kakitani et al. |

FOREIGN PATENT DOCUMENTS

| WO | 2008-031009 A2 | 3/2008 |
| WO | 2008-061013 A2 | 5/2008 |
| WO | 2010/037041 A2 | 4/2010 |
| WO | 2010-038756 A1 | 4/2010 |

OTHER PUBLICATIONS

European Patent Office, Communication dated Dec. 3, 2014, issued in corresponding EP Patent Application No. 12802608.5.
Dougall, et al.; "RANK is essential for osteoclast and lymph node development"; Genes & Development 13, pp. 2412-2424, 1999; Cold Spring Harbor Laboratory Press; ISSN 0890-9369/99.
Young-Yun Kong; et al.; "OPGL is a key regulator of osteoclastogenesis, lymphocyte development and lymph-node organogenesis"; NATURE; vol. 397; Jan. 28, 1999; pp. 315-323.
Lars E. Theill; et al.; "RANK-L and RANK: T Cells, Bone Loss, and Mammalian Evolution"; Annu. Rev. Immunol.; 2002; vol. 20; pp. 795-823.
G. Sanna, et al.; "Jaw avascular bone necrosis associated with long-term use of bisphosphonates"; Annals of Oncology; vol. 16; pp. 1207-1208, 2005.
Toshitaka Nakamura; Current status and future prospects on therapeutic agents of osteoporosis; The Bone vol. 22 No. 3; Jun. 2008; pp. 147-151.
Seiki Wada; et al.; "Appropriate Clinical Usage of Calcitonin Escape Phenomenon and Intermittent v.s. Daily Administration of Calcitonin"; Clinical Calcium vol. 11, No. 9, 2001; pp. 1169-1175.
Wada, et al.; "Mebio"; 2008 vol. 25 No. 8; pp. 89-95.
Takashi Nakamura, et al.; "Estrogen Prevents Bone Loss via Estrogen Receptor α and Induction of Fas Ligand in Osteoclasts"; Cell; vol. 130, pp. 811-823, Sep. 7, 2007.
S. Kousteni, et al.; "Nongenotropic, Sex-Nonspecific Signaling through the Estrogen or Androgen Receptors: Dissociation from Transcriptional Activity"; Cell, vol. 104, pp. 719-730, Mar. 9, 2001.
M. Michael Cohen Jr; "Research Review, The New Bone Biology: Pathologic, Molecular, and Clinical Correlates "; American Journal of Medical Genetics Part A; vol. 140A; pp. 2646-2706; May 20, 2006.
Ayuku Fujiu., et al.; Clinical Dialysis; 2008; vol. 24 No. 9; pp. 43-50.
John T. Daugirdas; "Handbook of Dialysis—Fourth Edition"; Medical Science International; 2009; pp. 3- 11 and 448-466.
Shunji Takahashi; "Cancer—Induced bone disease (bone metastases and hyercalcemia of malignancy"; The Bone; vol. 22 No. 3; 2008; pp. 115-120.
Satoshi Soen; "Rheumatoid Arthritis"; The Bone; vol. 22 No. 3; 2008; pp. 103-107.
Akihide Nampei; "Osteoarthritis—Clinical Aspect—"; The Bone; vol. 22 No. 3; 2008; pp. 109-113.
Guidelines for prevention and treatment of osteoporosis; Minds; 2006; URL> http://mtnds.jcqhc,or.jp/n/med/4/med0046/G0000129/0016; Life Science Japan; Committee for Preparing guidelines for prevention and treatment of osteoporosis; 8 pages total.
Shigeyuki Muraki, et al.; "Factors associated with mortality following hip fracture in Japan"; J. Bone Miner Metab; 2006; vol. 24; pp. 100-104.
Nguyen D Nguyen; et al.; "Bone Loss, Weight Loss, and Weight Fluctuation Predict Mortality Risk in Elderly Men and Women"; Journal of Bone and Mineral Research; vol. 22 No. 8, Apr. 23, 2007; pp. 1147-1154.

(Continued)

*Primary Examiner* — Elizabeth C Kemmerer
(74) *Attorney, Agent, or Firm* — Sughrue Mion, PLLC

(57) ABSTRACT

The present invention provides a protein comprising a truncated form of an extracellular region protein of Frizzled 2, which has higher secretion activity than that of a known protein comprising an extralellular cysteine-rich domain of Frizzled 2 in a production cell and bone mass-increasing activity higher than or equal to that of the known protein, or DNA encoding said protein.

11 Claims, 3 Drawing Sheets

(56) References Cited

OTHER PUBLICATIONS

Kousei Yoh, et al.; "Health-related quality of life (HRQOL) in Japanese osteoporotic patients and its improvement by elcatonin treatment"; J Bone Miner Metab.; 2005; vol. 23; pp. 167-173.

A. N. A. Tosteson, et al.; "Impact of Hip and Vertebral Fractures on Quality-Adjusted Life Years"; Osteoporos Int.; 2001; vol. 12; pp. 1042-1049.

Deltagen Inc.; "NIH Initiative supporting placement of Deltagen Inc. mice into public repositories Fzd1tm1Dgen"; MGI Direct Data Submission; 2005; 1 page total.

Tatjana Milovanovic, et al.; "Expression of Wnt genes and frizzled 1 and 2 receptors in normal breast epithelium and infiltrating breast carcinoma"; International Journal of Oncology; vol. 25; 2004; pp. 1337-1342.

R F Holcombe, et al.; "Expression of Wnt ligands and Frizzled receptors in colonic mucosa and in colon carcinoma"; J Clin Pathol: Mol Pathol; 2002; vol. 55; pp. 220-226.

Marcelo A. Chacon, et al.; "Frizzled-1 Is Involved in the Neuroprotective Effect of Wnt3a Against Aβ Oligomers" Journal of Cellular Physiology; vol. 217; 2008; pp. 215-227.

Elizabeth Vincan, et al.; "Frizzled-7 receptor ectodomain expression in a colon cancer cell line induces morphological change and attenuates tumor growth"; International Society of Differentiation; 2005; vol. 73; pp. 142-153.

Philippe Merle, et al.; "Oncogenic role of the frizzled-7/β-catenin pathway in hepatocellular carcinoma"; Journal of Hepatology; vol. 43; 2005; pp. 854-862.

Caroline R. Kemp, et al. "Expression of *Frizzled5, Frizzled7*, and *Frizzled10* During Early Mouse Development and Interactions With Canonical Wnt Signaling" Development Dynamics; vol. 236; pp. 2011-2019, 2007.

Norihiko Sagara, et al.; "Molecular Cloning, Differential Expression, and Chromosomal Localization of Human *Frizzled-1, Frizzled-2*, and *Frizzled-7*"; Biochemical and Biophysical Research Communications, vol. 252, pp. 117-122 (1998).

Masuko Katoh, et al.; "Comparative integromics on FZD7 orthologs: Conserved binding sites for PU.1, SP1, CCAAT-box and TCF/LEF/SOX transcription factors within 5'-promoter region of mammalian *FZD7* orthologs"; International Journal of Molecular Medicine; vol. 19: pp. 529-533, 2007.

Alex Gregorieff, et al.: "Expression Pattern of Wnt Signaling Components in the Adult Intestine"; Gastroenterology; vol. 129; pp. 626-638; 2005.

Ken Matsumoto, et al. "Wnt9a secreted from the walls of hepatic sinusoids is essential for morphogenesis, proliferation, and glycogen accumulation of chick hepatic epithelium"; Developmental Biology; vol. 319; pp. 234-247, 2008.

Grant N. Wheeler, et al.; "Inducible gene expression in transgenic *Xenopus* embryos"; Current Biology; vol. 10 No. 14; pp. 849-852; Jun. 2000.

Hui-Chuan Huang, et al.; "The Frizzled family: receptors for multiple signal transduction pathways"; Genome Biology; vol. 5 Issue 7; Article 234; Jun. 2004; 7 pages total.

Yanshu Wang et al.; "A Large Family of Putative Transmembrane Receptors Homologous to the Product of the *Drosophila* Tissue Polarity Gene *frizzled*"; the Journal of Biological Chemistry; vol. 271 No. 8; Feb. 1996; pp. 4468-4476.

Brune Trevant, et al.; "Expression of Secreted Frizzled Related Protein 1, A Wnt Antagonist, in Brain, Kidney, and Skeleton is Dispensable for Normal Embryonic Development"; Journal of Cellular Physiology; vol. 217; pp. 113-126; 2008.

Rika Nakanishi, et al.; "Secreted Frizzled-Related Protein 4 Is a Negative Regulator of Peak BMD in SAMP6 Mice "; Journal of Bone and Mineral Research; vol. 21 No. 11; 2006; pp. 1713-1721.

Shmuel Yaccoby, et al.; "Antibody-based inhibition of DKK1 suppresses tumor-induced bone resorption and multiple myeloma growth in vivo"; Blood; vol. 109 No. 5; Mar. 2007; pp. 2106-2111.

Xiaodong Li, et al.; "Targeted Deletion of Sclerostin Gene in Mice Results in Increased Bone Formation and Bone Strength"; Journal of Bone and Mineral Research; vol. 23 No. 6; 2008; pp. 860-869.

Mikhail Semenov, et al.; "SOST Is a Ligand for LRP5/LRP6 and a Wnt Signaling Inhibitor"; Journal of Biological Chemistry; vol. 280 No. 29; Jul. 22, 2005; pp. 26770-26775.

Georges Rawadi, et al.; "Wnt signaling pathway: a new target for the treatment of osteoporosis"; Expert Opin. Ther. Targets; 2005; vol. 9 No. 5; pp. 1063-1077.

Charles Dann, et al.; "Insights into Wnt binding and signaling from the structures of two Frizzled cysteine-rich domains"; Letters to Nature; vol. 412; Jul. 5, 2001; pp. 86-90.

Piotr Masiakowski and George D. Yancopoulos, "The Wnt receptor CRD domain is also found in MuSK and related orphan receptor tyrosine kinases"; Magazine; R407; vol. 8; Issue 12, Jun. 4, 1998; 1 page total and cover page.

Keiko Tamai, et al.; "LDL-receptor-related proteins in Wnt signal transduction"; Letters to Nature; vol. 407; Sep. 28, 2000; pp. 530-535.

Satoshi Mori; Clinician; 2002; vol. 49; No. 511; pp. 621-626.

Yi Tang, et al.; "TGF-β1-induced migration of bone mesenchymal stem cells couples bone resorption with formation"; Nature Medicine; vol. 15 No. 7; Jul. 2009; pp. 757-765.

Katrien Janssens, et al.; "Mutations in gene encoding the latency-associated peptide of TGF-β1 cause Camurati-Engelmann disease"; Nature Genetics; vol. 26; Nov. 2000; pp. 273-275.

Anna Daroszewska, et al.; "Mechanisms of Disease: genetics of Paget's disease of bone and related disorders"; Nature Clinical Practice Rheumatology; vol. 2, No. 5; May 2006; pp. 270-277.

Atsushi Horiuchi; Clinician; 2000; vol. 47 No. 490; pp. 401-404.

Search Report (PCT/ISA/210) issued Aug. 21, 2012 for corresponding International Application No. PCT/JP2012/065911.

Written Opinion (PCT/ISA/237) issued Aug. 21, 2012 for corresponding International Application No. PCT/JP2012/065911.

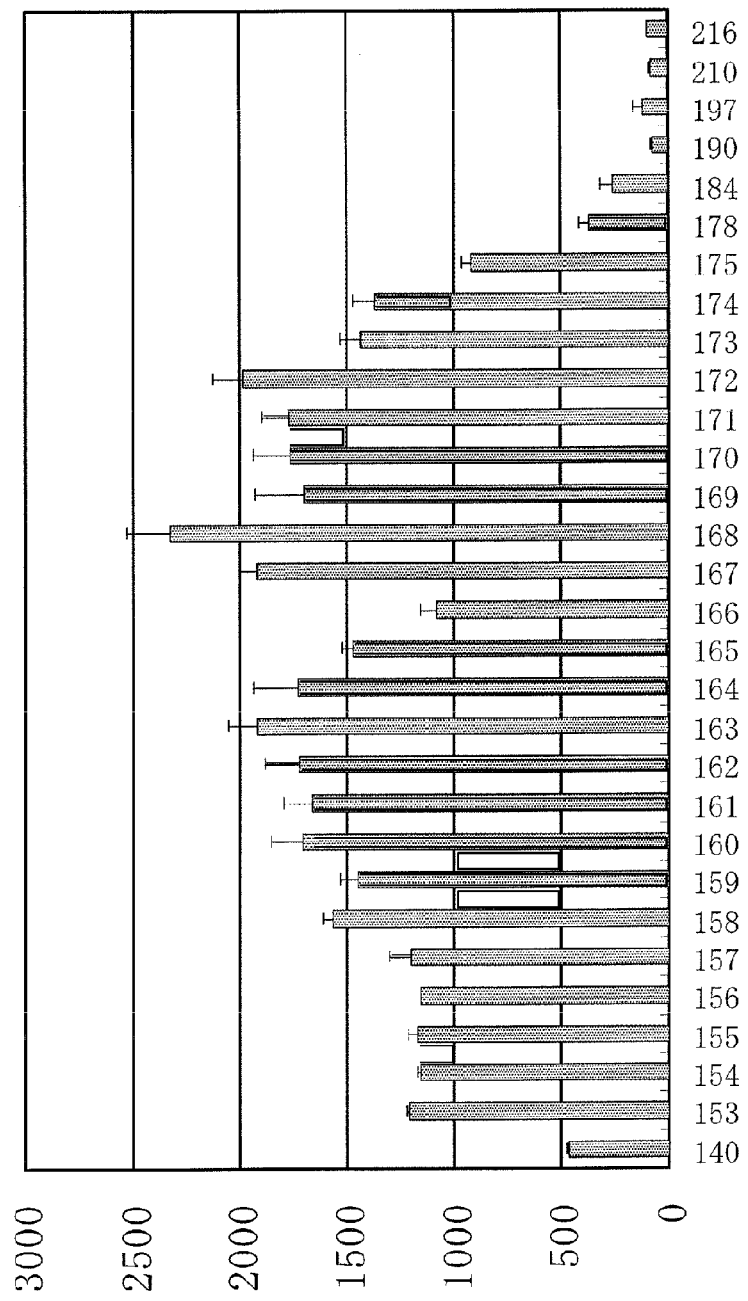

PROTEIN COMPRISING TRUNCATED FORM OF EXTRACELLULAR REGION PROTEIN OF FRIZZLED 2, AND PHARMACEUTICAL COMPOSITION FOR TREATING BONE DISEASES WHICH COMPRISES SAID PROTEIN

TECHNICAL FIELD

The present invention relates to a novel protein comprising a truncated form of an extracellular region protein of Frizzled 2 which has a high degree of secretion activity in production cells (also referred to as productivity) and/or bone mass-increasing activity when compared to a known protein comprising the extracellular cysteine-rich domain of Frizzled 2, and a pharmaceutical composition for treating bone diseases comprising the protein.

The present invention also relates to manufacturing methods of a novel protein comprising a truncated form of an extracellular region protein of Frizzle 2 which has a high degree of secretion activity in production cells and/or bone mass-increasing activity when compared to prior art proteins comprising an extracellular cysteine-rich domain of Frizzled 2, and a pharmaceutical composition containing the protein used for treatment of bone diseases.

The present invention also relates to therapeutic methods of bone disease using a novel protein comprising a truncated form of an extracellular region protein of Frizzled 2 which has a high degree of secretion activity in production cells and/or bone mass-increasing activity when compared to prior art proteins comprising an extracellular cysteine-rich domain of Frizzled 2, and a pharmaceutical composition containing the protein used for treatment of bone diseases.

These findings have been discovered based on the preparation of production cells for a protein comprising a truncated form of an extracellular region protein of Frizzled 2, and the characterization of mice to which the protein is administered.

BACKGROUND ART

A super-aging society has arrived, the number of people with osteoporosis has increased, and bone fractures resulting therefrom have come to constitute a serious issue of concern at a societal level. In particular, patients with femoral neck fractures and vertebral body fractures become bedridden, which causes significant deterioration of the quality of life thereof, and the social, medical, and economic burdens caused by care and hospital treatment have increased (Non-Patent Literatures 1 and 2).

It has also been discovered in recent years that osteoporosis is significantly associated with mortality in old age (Non Patent Literatures 3 and 4). Under such circumstances, prevention and treatment of osteoporosis have become critical objectives to be achieved.

Osteoporosis (i.e., a pathological condition where bone mass is reduced while the rate of the amount of the bone matrix to the amount of the mineralized bone matrix is held) is classified as primary osteoporosis or secondary osteoporosis. The former type is a pathological condition heretofore referred to as postmenopansal osteoporosis or senile osteoporosis. The latter type is a pathological condition caused by changes in bone metabolism resulting from other diseases, and such osteoporosis is classified based on the cause thereof, such as osteoporosis caused by endocrine, nutritional/metabolic, inflammatory, immobile, drug-induced, hematologic, congenital, or other diseases.

According to the above classification, endocrine causes include such as hyperparathyreosis, hyperthyreosis, hypogonadism, Cushing's syndrome, somatotropin deficiency, diabetes, Addison's disease, and calcitonin deficiency.

Nutritional/metabolic causes include such as chronic degenerative diseases, emaciation, serious liver diseases (primary biliary cirrhosis, in particular), gastric resection, scorbunts, malabsorption syndrome (including celiac disease), hypophosphatemia, chronic renal disease, hypercalciuria, hemochromatosis, amyloidosis, mast cell tumor, ingestion of excess sodium, insufficient calcium intake, and hypervitaminosis D or A. Inflammatory causes include such as articular rheumatism, particular bone disease (elevated bone resorption induced by proinflammatory cytokines), and sarcoidosis.

Immobility-related causes include such as systemic, bed rest, paralysis, local, and post-fracture causes. Drug-induced causes include such as with the use of steroids (steroids are extensively used for inflammatory diseases as immunosuppressive agents; examples of diseases treated with the use of steroids include collagen diseases, asthma, inflammatory bowel diseases, and in the case of organ transplantation, and bone loss is a serious side effect of such therapy), methotrexate, heparine, warfarin, anticonvulsant agents, lithium, and tamoxifen.

Blood-disease-induced causes include such as multiple myeloma, lymphoma, leukaemia, hemophilia, and chronic hemolytic diseases. Congenital causes include such as dysosteogenesis, Marfan's syndrome, Kleinfelter's syndrome, congenital erythropoetic porphyria, and cystic fibrosis.

Other disease-induced causes include such as with chronic obstructive lung diseases, hepatic failure, renal diseases, articular rheumatism, pregnancy, hyperoxemia, and HIV infection (Non-Patent Literature 5).

Among the above-mentioned diseases, bone diseases resulting from osteoarthritis, articular rheumatism, malignant tumors, or renal diseases are specifically regarded as bone diseases that impose serious influences at the societal level, in addition to primary osteoporosis. Osteoarthritis develops most often in locomotor regions. The number of patients afflicted therewith is said to be 10,000,000 in Japan, and it has been deduced that the number of patients will keep increasing as the aging of society advances. Advanced articular disorders are treated via artificial joint replacement; however, radical treatment of moderate or milder symptoms has not yet been reported (Non-Patent Literature 6).

Articular rheumatism is a chronic and progressive inflammatory disease characterized mainly by multiple arthritis. Articular synovial proliferation gradually causes infiltration of cartilage or bones in the vicinity thereof, and articular rheumatism often leads to destruction and deformation of joints. It has been reported that treatment with the use of an antirheumatic drug (methotrexate) cannot sufficiently inhibit the progress of joint destruction, and a biological agent targeting a tumor necrosis factor (TNF) α produces significant effects of inhibiting joint destruction. Thus, it is considered to be a revolutionary agent. However, increased incidence, as a side effect, of opportunistic infection, tuberculosis (extrapulmonary tuberculosis), Pneumocystispneumonia, or the like when using such agent is an issue of concern (Non-Patent Literature 7).

Major examples of bone diseases involved in malignant tumors include hypercalcemia and bone metastasis related to malignant tumors. Hypercalcemia causes loss of appetite and diuresis, and it causes dehydration and renal failure caused thereby. Bone metastasis is often observed in patients with breast cancer, prostate cancer, or lung cancer, in particular. While bone metastasis is hardly ever fatal by itself, it causes bone ache, pathologic fracture, neuroparalysis, or the like. It thus often significantly deteriorate patients' QOL, and bone metastasis control is a critical objective in clinical settings (Non-Patent Literature 8). These bone diseases related to malignant tumors are treated with the use of bisphosphonate preparations, although the problem of side effects has been pointed out.

Among bone diseases related to renal diseases, a pathological condition of bone damage caused by renal tissue damage is referred to as renal osteodystrophy. Bone disease experienced by kidney dialysis patients are mainly caused by secondary hyperparathyreosis. Because of the elevated PTH concentration caused by hyperparathyreosis and, for example, insufficient production of bone morphogenetic protein (BMP) 7, renal osteodystrophy advances. Dialysis patients often exhibit lowered reactivity of the bone with the parathyroid hormone (PTH). When the PTH concentration is chronically and significantly elevated, accordingly, fibrous ostitis (high bone turnover) develops. When the PTH concentration is maintained within a standard range, in contrast, bone aplasia (low bone turnover) develops.

When fibrous ostitis advances, collagen fibers are irregularly formed, such fibers are mineralized as non-crystalline calcium phosphate, and woven bone is then formed. This enhances bone formation, although the bone becomes easily fracturable. Basic treatment of fibrous ostitis involves inhibition of parathyroid hormone secretion, which mainly entails calcium ingestion and administration of active vitamin D.

When a patient has a chronic kidney disease (CKD) and receives dialysis treatment, in particular, various regulations, such as restrictions on food or water intake, are necessary. When secondary hyperparathyreosis advances, hypercalcemia also becomes an issue of concern. When prescribing active vitamin D, extreme caution, such as via the monitoring of renal functions (i.e., serum creatinine level) and serum calcium level, is always required.

Bone aplasia develops because of prolonged use and excessive administration of active vitamin D preparations or suppression of parathyroid hormone after parathyroidectomy (PTX). The rate of fractures associated with bone aplasia is higher than that associated with fibrous ostitis, and it induces hypercalcemia or mineralization of blood vessels or other soft tissues. Thus, adequate treatment techniques have been desired. A pathological condition of bone aplasia is low bone turnover in which bone resorption and bone formation are inhibited, and there is no established treatment technique at present (Non-Patent Literature 9).

Hyperphosphatemia or hypercalcemia caused by lowered capacity of the bone for phosphorus or calcium intake (low-turnover metabolic bone) or lowered storage capacity (high-turnover metabolic bone) is considered to be a cause of ectopic (vascular) mineralization. Cardiovascular complications account for 40% or more of the deaths of patients with chronic renal failures, and dialysis patients in particular, and arteriosclerosis involving vascular mineralization has drawn attention as a serious pathological condition. Treatment of mineralization of advanced lesions in patients with chronic renal failures remains difficult at present and the prognosis thereof is poor (Non-Patent Literature 10).

In addition to agents for treating primary osteoporosis, accordingly, development of agents that more effectively act on bone diseases resulting from osteoarthritis, articular rheumatism, malignant tumors, or renal disease and vascular mineralization resulting from bone diseases with reduced side effects has been desired.

It is considered that bone metabolism is regulated by the balance between osteoblast functions and osteoclast functions, and osteoporosis develops when the bone-destroying activity exceeds bone-building activity (Non-Patent Literature 11). In particular, secretion of the female hormone that assumes the role of protecting bones is lowered in post-menopausal women, a lowered capacity of osteoblasts for bone formation and the elevated bone resorption activity of osteoclasts are consequently observed, and it is highly likely that symptoms of osteoporosis would develop (Non-Patent Literatures 12 and 13).

In order to overcome such problems, estrogen preparations have been used; however, application thereof has been restricted due to the increased risk of thrombosis and breast cancer caused by the use of such preparations. It is also reported that use of a selective estrogen receptor modulator would increase the risk of deep vein thrombosis (Non-Patent Literature 14).

At present, calcitonin, bisphosphonate, and the like are used as agents that inhibit the bone resorption activity of osteoclasts. Calcitonin is known to bind to a calcitonin receptor expressed on the osteoclast surface to inactivate osteoclasts, and it is used for treatment of not only osteoporosis but also hypercalcemia, Paget's disease of bone, and the like in clinical settings.

However, no effects thereof on bone fracture inhibition have yet been found, and calcitonin receptor expression is reported to be down-regulated by calcitonin administration (Non-Patent Literatures 14 and 15). Bisphosphonate exhibits potent bone resorption inhibitory activity, and amino-containing bisphosphonates, such as andronate and risedronate, are major therapeutic agents for osteoporosis in Japan. Such bisphosphonate preparations inhibit farnesyl diphosphate synthase, block lipid protein prenylation, and induce inhibition of bone-resorption functions and osteoclast apoptosis (Non-Patent Literature 16).

However, the FDA warned of crises of severe skeletal, articular, or muscular pain in 2008 as problems of bisphosphonate preparations. In addition, side effects, such as jaw bone necrosis, caused by the prolonged use thereof (i.e., for 2 or 3 years or longer) after dental care have been reported (Non-Patent Literature 17).

An anti-RANK antibody has been expected as a novel osteoclastic inhibitor other than those described above. Further, application of the anti-RANK antibody as an inhibitor of articular destruction in the case of articular rheumatism or as a therapeutic agent for multiple myeloma has been expected, and clinical development thereof is in progress.

Based on a report to the effect that the RANKL/RANK pathway is important for the survival and maintenance of dendritic cells (Non-Patent Literature 18), or a report to the effect that lymph node dysplasia is caused in an RANK- or RANKL-deficient mouse (Non-Patent Literatures 19 and 20), the influence of an anti-RANK antibody preparation on the immune system has become an issue of concern.

In 2008, AMGEN reported that an increased rate of development of some infectious diseases was found through a clinical test of the anti-RANK antibody preparation (Denosumab). As a result of the clinical test of the anti-RANK antibody conducted in 2009, development of jaw bone necrosis was found to be a side effect, as in the cases of the bisphosphonate preparations.

Treatment via intermittent administration of PTH alone as an osteogenesis accelerator that activates osteoblasts has been conducted (Eli Lilly, teriparatide), but such agent is not different from other therapeutic agents, such as bisphosphonate preparations, in that activity of increasing cortical bone thickness is not very high compared with activity of increasing cancellous bone mass.

Accordingly, the effects thereof for bone fracture prevention are not considered to be very high. In relation to PTH, further, Asahi Kasei Pharma Corp. (Japan) has reported problems, such as side effects such as palpitation, tachycardia, and a lowering in blood pressure, and osteosarcoma observed in a long-term administration test to rats, unapproved continuous use thereof for 1.5 to 2 years or longer in Europe and the United States, and prohibited application thereof to cancer patients. Thus, it is impossible to use PTH for inhibition of cancer bone metastasis, treatment of cancer induced hypercalcemia (paraneoplastic humoral hypercalcemia or local osteolytic hypercalcemia caused by the parathyroid-hormone-related peptide produced by tumor cells), or other purposes.

Accordingly, development of agents that more effectively work for osteoporosis caused by the lowered capacity of osteoblasts for bone formation or elevated bone resorption activity of osteoclasts in postmenopausal women, hypercalcemia, Paget's disease of bone, inhibition of bone metastasis, inhibition of articular destruction associated with articular rheumatism, or multiple myeloma with reduced side effects has been awaited.

In addition thereto, osteohalisteresis andrachitis are known as bone diseases induced by selective inhibition of mineralization, unlike osteoporosis. A bone is formed by mineralization of a matrix layer comprising collagen or the like via hydroxyapatite deposition. Osteohalisteresis is a pathological condition in which such mineralization is blocked and osteoids increase, and it is referred to as rachitis if developed during childhood.

Symptoms include bone and joint pains, such as chiropodalgia, arthralgia, lumbago, and backache, which lead to gait impairment and to a state in which bone is easily fractured. In the case of children, developmental disorders, limb deformities such as bow-legs, pigeon breast deformity, or other symptoms are observed. Such symptoms are generally treated with the use of vitamin D, calcium preparations, and phosphorus preparations, in addition to alimentary therapy. If the level of dysfunction caused by a deformity is high, however, surgical operation is the only possible symptomatic treatment. Therefore, development of agents that are more effective on osteohalisteresis or rachitis has been awaited.

As described above, bone is tissue that is always regulated by the balance between osteoblast functions and osteoclast functions and remodeled. In order to achieve tough bone that is more resistant to fracture, accordingly, a mere increase in bone mass may not be sufficient.

In the case of hereditary diseases, such as osteopetrosis (Non-Patent Literature 21), Paget disease of bone (Non-Patent Literature 22) or Camurati-Engelmann's disease (CED) (Non-Patent Literatures 23 and 24), for example, it is known that the balance between bone formation and bone resorption becomes abnormal due to different causes, and bone strength is lowered even though bone mass is increased.

Examples of factors that determine bone strength from the viewpoint of mechanisms of materials include form-related factors, such as connectivity of cancellous bones, thickness of cortical bones, porosity, and cross-sectional moment, and qualitative factors, such as mineralization or bone fatigue, in addition to quantitative factors represented by bone density (Non-Patent Literature 25). Therefore, development of agents useful for improving bone strength, in addition to increasing bone mass, has been awaited for the purpose of treatment of primary osteoporosis and secondary osteoporosis.

In recent years, factors associated with the Wnt/LRP signal control mechanism have drawn attention as targets for drug discovery regarding a bone formation accelerator. Wnt is a secreted glycoprotein that has been lipid-modified by palmitic acid having a molecular weight of about 40,000, and 19 types thereof are considered to be present in mammalian animals. As Wnt receptors, 10 types of seven-transmembrane receptors (i.e., Frizzled receptors) and two types of single transmembrane receptors (i.e., LRP5/6 receptors) have been reported (Non-Patent Literature 26).

A region referred to as a cysteine-rich domain (CRD) containing conserved 10 cysteine residues is present in an extracellular region of the Frizzled receptor family molecule to which Wnt is considered to bind. The region from the cysteine residue located closest to the N-terminus to the cysteine residue located closest to the C-terminus of such 10 cysteine residues may be exclusively designated as a CRD (Non-Patent Literature 27), or a region comprising such 10 cysteine residues and sequences each located closer to the C- or N-terminus may be designated as a CRD (R&D systems). CRDs were reported to have homodimer structures based on crystal structural analysis using a CRD of mouse Frizzled 8 (Non-Patent Literature 28).

At least three types of Wnt signaling pathways are considered to exist: a canonical-Wnt signaling pathway; a non-canonical Wnt signaling pathway, which is a PCP (planar cell polarity) pathway mediated by a small G-binding protein; and a Ca2+ pathway mediated by a trimeric G protein. Bone-metabolism-related research on the canonlcal-Wnt signaling pathway is the most advanced, and Wnt is considered to promote bone formation (Non-Patent Literature 29). Therefore, regulation of functions of endogenous factors that inhibit this signaling pathway has been attempted in recent years for the purpose of application thereof to treatment of bone diseases.

Sclerostin was recognized as a BMP antagonist at first; however, it was reported to be a factor that would directly bind to LRP5/6 to inhibit the signaling pathway in research conducted later (Non-Patent Literature 30). A significant increase was observed in bone density in a Sclerostin-knockout mouse (Non-Patent Literature 31). At present, a Sclerostin-neutralizing antibody is undergoing phase II trials in Europe and the United States of America (AMG785, Amgen & UCB), and the future development thereof has drawn attention.

A DKK1 (Dickkopf-1)-neutralizing antibody that is known as another canonlcal-Wnt signal inhibitor was prepared, inhibition of lowered bone density was observed in an SCID mouse into which multiple myeloma (MM) cells had been transplanted (Non-Patent Literature 32), and clinical trials using a neutralizing antibody (BHQ880, Novartis) have been conducted.

sFRP (soluble frizzled-related protein) that is considered to be a Wnt decoy receptor and has high amino acid sequence homology to the Frizzled extracellular domain is considered to negatively regulate Wnt signals (Non-Patent Literature 33), and an increase in the amount of cancellous bone in the femur of an sFRP1 knockout mouse has been reported (Non-Patent Literature 34). Under such circumstances, research and development related to sFRP1 inhibitors have proceeded (Wyeth).

Frizzled 7 has been identified as a receptor that binds to a Wnt ligand and transmits signals thereof (Non-Patent Literatures 35 and 36). The amino acid sequence of the human Frizzled 7 extracellular cysteinerich domain (when a region from the cysteine residue located closest to the N-terminus to the cysteine residue located closest to the C-terminus of such 10 conserved cysteine residues is exclusively designated as a CRD) is completely identical to that of the mouse Frizzled 7 extracellular cysteine-rich domain (i.e., there is no difference between species). Involvement thereof with generation and differentiation of individual organisms (Non-Patent Literature 37) and involvement thereof with liver cell multiplication (Non-Patent Literature 38) have been reported.

Expression patterns of such molecules have been reported: an expression pattern localized in the crypt base of the mouse small intestine or large intestine (Non-Patent Literature 39); elevated expression levels in various cancer cells (Non-Patent Literature 40); expression in various tissues (the brain, eyeball, heart, kidney, liver, lung, or spermary) other than those of the spleen via expression analysis of adult mouse-derived tissues of (Non-Patent Literature 35); and expression in tissue (the lung or kidney) other than those of the brain and the liver via expression analysis of human fetal tissue and potent expression in the skeletal muscle and relatively potent expression in the heart, weak expression in the brain, the placenta, and the kidney; and no expression in the lung, the liver, the pancreas, the spleen, the thymic gland, the prostate, the testicle, the ovary, the small intestine, or the large intestine via expression analysis of adult human-derived tissue (Non-Patent Literature 41).

An extracellular cysteine-rich domain that is a soluble receptor of the Frizzled receptor is considered to bind to Wnt and inhibit functions thereof. It is reported by an in vitro experimentation system that a fusion product of the Frizzled 7 extracellular cysteine-rich domain (comprising a region from the cysteine residue located closest to the N-terminus to the cysteine residue located closest to the C-terminus of the conserved 10 cysteine residues and sequences each located closer to the C- or N-terminus) and Fc (R & D Systems) inhibits stabilization of cytoplasmic β-catenin by Wnt3a (Non-Patent Literature 42).

Since the expression level of Frizzled 7 is elevated in cancer cells, it has drawn attention as a target molecule for tumor treatment (Patent Literature 2, Non-Patent Literature 43). Regarding colon cancer cells into which a vector that expresses a Frizzled 7 extracellular domain has been introduced, for example, growth thereof was inhibited to a greater extent in a xenograft tumor cell transplantation model compared with colon cancer cells into which a control vector had been introduced (Non-Patent Literature 44). This suggests the possibility that Frizzled 7 would be a target of drug discovery for tumor treatment.

As described above, 10 types of Frizzled family molecules have been reported, and Frizzled 1 and Frizzled 2 have been reported as molecules having particularly high primary sequence homology with Frizzled 7 in the extracellular cysteine-rich domain (when a region from the cysteine residue located closest to the N-terminus to the cysteine residue located closest to the C-terminus of the conserved 10 cysteine residues is exclusively designated as a CRD; Non-Patent Literature 22).

The amino acid homologies of Frizzled 7 in the cysteine rich domain (when a region from the cysteine residue located closest to the N-terminus to the cysteine residue located closest to the C-terminus of the conserved 10 cysteine residues is exclusively designated as a CRD) of such molecule to Frizzled 1 and Frizzled 2 are 91% and 93% respectively in humans and mice. That is, such amino acid sequence homology is very high.

As with the case of Frizzled 7, Frizzled 1 and Frizzled 2 do not show differences between mouse-derived and human-derived amino acid sequences in the cysteine rich domain (when a region from the cysteine residue located closest to the N-terminus to the cysteine residue located closest to the C-terminus of the conserved 10 cysteine residues is exclusively designated as a CRD); i.e., such sequences are 100% consistent with each other.

As with Frizzled 7, it is reported that both Frizzled 1 and Frizzled 2 interact with Wnt and Frizzled 1 interacts with Wnt3a to protect the hippocampal neuron from being destroyed by amyloid β peptide (Non-Patent Literature 45).

In addition, regarding Frizzled 1 expression patterns, potent expression in the heart, the placenta, the lung, the kidney, the pancreas, the prostate, and the ovary observed via expression analysis of adult human derived tissue and potent expression in the lung and the kidney observed via expression analysis of fetus-derived tissue have been reported (Non-Patent Literature 41).

Since the expression levels of both Frizzled 1 and Frizzled 2 are elevated in the case of colon cancer or breast cancer, the correlation thereof with canceration is suggested, and they have drawn attention as target molecules for tumor treatment (Patent Literature 1, Non-Patent Literatures 46 and 47). Further, it was reported that Frizzled 1 would not cause any changes in the phenotype of the Frizzled 1 gene-disrupted mouse (Non-Patent Literature 48).

In super-aging society, bone diseases involved in osteoporosis, arthritis deformans, rheumatoid arthritis and malignant tumors and treatment of these bone diseases is increasingly considered as socially important issue, and medicaments for treating bone diseases are vigorously researched and developed.

Kakitani and co-workers have found that a protein containing an extracellular cysteine-rich domain derived from Frizzled 1, Frizzled 2 or Frizzled 7 specifically promotes an increase in bone mass and bone strength (Patent Literature 3). However, there still remains a need for more improvement of secretion activity in production cells (productivity) and bone mass-increasing activity.

CITATION LIST

Patent Literature

[Patent Literature 1] WO 2008/061013
[Patent Literature 2] WO 2008/031009
[Patent Literature 3] WO 2010/038756

Non-Patent Literature

[Non-Patent Literature 1] Tosteson, A. N., et al., Osteoporos Int., 12, 1042-1049 (2001)
[Non-Patent Literature 2] Yoh, K., et al., J. Bone Miner. Metab., 23, 167-173 (2005)
[Non-Patent Literature 3] Nguyen, N. D., et al., J. Bone Miner. Res., 22, 1147-1154 (2007)
[Non-Patent Literature 4] Muraki, S., et al., J. Bone Miner. Metab., 24, 100-104 (2006)
[Non-Patent Literature 5] Committee for preparing guidelines for prevention and treatment of osteoporosis, Guidelines for prevention and treatment of osteoporosis, 2006, Life Science (Japan)(2006)
[Non-Patent Literature 6] Nampei, A. & Hashimoto, J., The Bone, 22, 3, 109-113 (2008)
[Non-Patent Literature 7] Soen, S., The Bone, 22, 3, 103-107 (2008)

[Non-Patent Literature 8] Takahashi, S., The Bone, 22, 3, 115-120 (2008)

[Non-Patent Literature 9] Daugirdas, J. T., et al., Clinical dialysis handbook 4rd edition, Medical Science International (Japan)(2009)

[Non-Patent Literature 10] Ayuko Fujiu, et al., Clinical dialysis, 24, 43-50, Japan Medical Center (Japan)(2008)

[Non-Patent Literature 11] Cohen, M. M. Jr., American J. Med. Genetics, Part A, 140A, 2646-2706 (2006)

[Non-Patent Literature 12] Kousteni, S., et al., Cell, 104, 719-730 (2001)

[Non-Patent Literature 13] Nakamura, T., et al., Cell, 130, 811-823 (2007)

[Non-Patent Literature 14] Wada, S., et al., Mebio, 25, 8, 89-95 (2008)

[Non-Patent Literature 15] Wada, S.& Yasuda, S., Clin. Calcium, 11, 9, 1169-1175 (2001)

[Non-Patent Literature 16] Nakamura, T., The Bone, 22, 3, 147-151 (2008)

[Non-Patent Literature 17] Sanna, G., et al., Ann. Oncol., 16, 1207-1208 (2005)

[Non-Patent Literature 18] Theill, L. E., et al., Ann. Rev. Immunol., 20, 795-823 (2002)

[Non-Patent Literature 19] Kong, Y. Y., et al., Nature, 397, 315-323 (1999)

[Non-Patent Literature 20] Dougall, W. C., et al., Genes Dev., 13, 2412-2424 (1999)

[Non-Patent Literature 21] Atsushi Horiuchi, CLINICIAN, 47, 401-404 (2000)

[Non-Patent Literature 22] Daroszewska, A., & Ralston, S. H., Nature Clinical Practice Rheumatology, 2, 270-277 (2006)

[Non-Patent Literature 23] Janssens, K., et al., Nature Genetics, 26, 273-275 (2000)

[Non-Patent Literature 24] Tang, Y., et al., Nature Medicine, 15, 757-765 (2009)

[Non-Patent Literature 25] Satoshi Mori, CLINICIAN, 49, 621-626 (2002)

[Non-Patent Literature 26] Tamai, K., et al., Nature, 407, 530-535 (2000)

[Non-Patent Literature 27] Masiakowski, P., & Yancopoulos, G D., Curr. Biol. 8, R407 (1998)

[Non-Patent Literature 28] Dann, C. E., et al., Nature, 412, 86-90 (2001)

[Non-Patent Literature 29] Rawadi, G & Roman-Roman, S., Expert Opin. Ther. Targets, 9, 5, 1063-1077 (2005)

[Non-Patent Literature 30] Semenov, M., et al., J. B. C., 280, 29, 26770-26775 (2005)

[Non-Patent Literature 31] Li, X., et al., J. Bone Miner. Res., 23, 860-869 (2008)

[Non-Patent Literature 32] Yaccoby, S., Blood., 109, 2106-2111 (2007)

[Non-Patent Literature 33] Nakanishi, R., et al., J. Bone Miner. Res., 21, 1713-1721 (2006)

[Non-Patent Literature 34] Trevant, B., et al., J. Cell. Physiol. 217, 113-126 (2008)

[Non-Patent Literature 35] Wang, Y., et al., J. B. C., 271, 8, 4468-4476 (1996)

[Non-Patent Literature 36] Huang, H-C., & Klein, P. S., Genome Biology, 5, 234, 1-7 (2004)

[Non-Patent Literature 37] Wheeler, G. N., Current Biology, 10, 849-852 (2000)

[Non-Patent Literature 38] Matsumoto, K., et al., Dev. Biol., 319, 2, 234-247 (2008)

[Non-Patent Literature 39] Gregorieff, A., et al., Gastroenterology, 129, 626-638 (2005)

[Non-Patent Literature 40] Katoh, M. & Katoh, M., Int. J. Mol. Med., 19, 529-533 (2007)

[Non-Patent Literature 41] Sagara, N., et al., B. B. R. C., 252, 117-122 (1998)

[Non-Patent Literature 42] Kemp, C. R., et al., Dev. Dynamics, 236, 2011-2019 (2007)

[Non-Patent Literature 43] Merle, P., et al., J. Hepatol., 43, 5, 854-862 (2005)

[Non-Patent Literature 44] Vincan, E., et al., Differentiation, 73, 142-153 (2005)

[Non-Patent Literature 45] Chacon, M. A., et al., J. Cell Physiol., 217, 215-227 (2008)

[Non-Patent Literature 46] Holcombe, R. F., et al., Mol. Pathol., 55, 220-226 (2002)

[Non-Patent Literature 47] Milovanovic, T., et al., Int. J. Oncology, 25, 1337-1342 (2004)

[Non-Patent Literature 48] Deltagen, Inc., "NIH initiative supporting placement of Deltagen, Inc. mice into public repositories" MGI Direct Data Submission 2005 (http://www.informatics.jax.org/javawi2/servlet/WIFetch?page-alleleDetail&key=40116)

DISCLOSURE OF INVENTION

Problems to be Solved by the Invention

The present invention has been developed to solve above-mentioned problems. A major objective of the present invention is to provide a protein comprising a truncated form of an extracellular region protein derived from Frizzled 2 which has a high degree of secretion activity in production cells, and/or excellent bone mass-increasing activity, and a pharmaceutical composition containing the protein.

Means for Solving the Problems

Surprisingly, the inventors have found that secretion activity in production cells is dramatically increased using a protein comprising an extracellular region protein of Frizzled 2, in particular a truncated form of the extracellular region protein comprising minimal region sequence of a cysteine-rich domain represented by SEQ ID NO:102 and having 141 to 175 amino acids in length (hereinafter, it is also referred to as a protein comprising a truncated form of an extracellular region protein of Frizzled 2).

More particularly, the inventors have found that secretion activity in production cells of a fusion protein is dramatically increased wherein the protein comprising a truncated form of an extracellular region protein of Frizzled 2 is a fusion protein of the truncated form of the extracellular region protein and a human Fc protein.

Further, the inventors have found for the first time that the protein comprising a truncated form of an extracellular region protein of Frizzled 2 has bone mass-increasing activity greater than or at least equal to proteins comprising an extracellular cysteine-rich domain of Frizzled 2 as disclosed in Patent Literature 3.

Based on these findings, it is demonstrated that a protein comprising a truncated form of an extracellular region protein of Frizzled 2, and a pharmaceutical composition for treating bone diseases comprising the protein can be efficiently obtained.

That is, the present invention is as follows.

1. A protein comprising the minimal region sequence of cysteine-rich domain (CRD) represented by SEQ ID NO:102 and having 141 to 175 amino acids in length.

2. The protein according to item 1 above, wherein 14 to 48 amino acids are added to the C-terminal of the minimal region sequence of cysteine-rich domain represented by SEQ ID NO:102.
3. The protein according to item 2 above, wherein 26 to 48 amino acids are added to the C-terminal of the minimal region sequence of cysteine-rich domain represented by SEQ ID NO:102.
4. The protein according to item 3 above, wherein 32, 38, 44, or 48 amino acids are added to C-terminal of the minimal region sequence of cysteine-rich domain represented by SEQ ID NO:102.
5. The protein according to any one of items 1 to 4 above, wherein amino acids comprising at least the amino acids from V at position 128 to L at position 141 in the amino acid sequence represented by SEQ ID NO:1 are added to the C-terminal of the minimal region sequence of cysteine-rich domain represented by SEQ ID NO:102.
6. The protein according to item 5 above, wherein amino acids having any length selected from the amino acids from T at position 142 to P at position 175 in the amino acid sequence represented by SEQ ID NO:1 are additionally added after L at position 141 of the amino acid sequence represented by SEQ ID NO:1.
7. The protein according to any one of items 1 to 6 above, wherein 1 to 15 amino acids are added to the N-terminal of the minimal region sequence of cysteine-rich domain represented by SEQ ID NO:102.
8. The protein according to item 7 above, wherein the amino acids added to the N-terminal of the minimal region sequence of cysteine-rich domain represented by SEQ ID NO:102 are amino acids having any length selected from the amino acids from Q at position 1 to F at position 15 in the amino acid sequence represented by SEQ ID NO:1.
9. A protein comprising amino acids from the amino acid Q at position 1 of the N-terminal to any one amino acid of A at position 153, G at position 154, G at position 155, T at position 156, P at position 157, G at position 158, G at position 159, P at position 160, G at position 161, G at position 162, G at position 163, G at position 164, A at position 165, P at position 166, P at position 167, R at position 168, Y at position 169, A at position 170, T at position 171, L at position 172, E at position 173, H at position 174, or P at position 175 of the amino acid sequence represented by SEQ ID NO:1.
10. The protein according to any one of items 1 to 9 above, wherein the protein is chemically modified.
11. The protein according to item 10 above, wherein the protein is chemically modified by binding to one or more polyethylene glycol molecules.
12. The protein according to item 10 above, wherein the protein is chemically modified by binding to a sugar chain.
13. The protein according to any one of items 1 to 12 above, wherein the protein is a recombinant protein.
14. A fusion protein of the protein according to any one of items 1 to 13 above and a mammal-derived immunoglobulin Fc protein or a variant of the mammal-derived immunoglobulin Fc protein.
15. The fusion protein according to item 14 above, wherein the mammal-derived immunoglobulin Fc protein consists of the amino acid sequence represented by SEQ ID NO:3.
16. The fusion protein comprising the amino acid sequence represented by any one of SEQ ID NOs:72 to 94.
17. A pharmaceutical composition for treating bone diseases comprising the fusion protein according to any one of items 14 to 16 above.
18. DNA encoding the protein according to any one of items 1 to 13 above or the fusion protein according to any one of items 14 to 16.
19. The DNA according to item 18, wherein nucleotide sequence encoding the mammal-derived immunoglobulin Fc protein is the nucleotide sequence represented by SEQ ID NO:4.
20. DNA consisting the nucleotide sequence represented by any one of SEQ ID NOs:42 to 64.
21. A pharmaceutical composition for treating bone diseases comprising the DNA according to any one of items 18 to 20 above.
22. The pharmaceutical composition for treating bone diseases according to item 17 or 21 above, wherein the bone diseases are diseases involving decrease in at least one selected from bone mass, bone density and bone strength.
23. A method for treating bone diseases comprising administrating to a mammal the pharmaceutical composition for treating bone diseases according to item 17, 21 or 22 above.
24. The method according to item 23 above, wherein the mammal is a human being.
25. The method according to item 23 or 24 above, wherein the bone diseases are diseases involving decrease in at least one selected from bone mass, bone density and bone strength.
26. The method according to any one of items 23 to 25 above, wherein the pharmaceutical composition for treating bone diseases is simultaneously or sequentially administrated in combination with other therapeutic drugs for treating bone diseases.

Effect of Invention

A protein comprising a truncated form of an extracellular region protein of Frizzled 2 of the present invention has a high degree of secretion activity in production cells. Also, the protein comprising a truncated form of an extracellular region protein of Frizzled 2 of the present invention has bone mass-increasing activity greater than or equal to proteins comprising an extracellular cysteine-rich domain of Frizzled 2 as disclosed in Patent Literature 3.

Thus, according to the present invention, a protein comprising a truncated form of an extracellular region protein derived from Frizzled 2 which has improved secretion activity in production cells and/or bone mass-increasing activity can be efficiently obtained. Furthermore, by using said protein, diseases involving a reduction in bone mass, bone density and/or bone strength, for example osteoporosis, arthritis deformans, rheumatoid arthritis, bone diseases resulting from malignant tumors, and various related bone diseases and disorders can be treated without causing side effects.

BRIEF DESCRIPTION OF THE DRAWINGS

FIG. 3 shows concentrations of hFZD2(140)-hFcm, hFZD2(153)-hFcm to hFZD2(175)-hFcm, hFZD2(178)-hFcm, hFZD2(184)-hFcm, hFZD2(190)-hFcm, hFZD2 (197)-hFcm, hFZD2(210)-hFcm, and hFZD2(216)-hFcm in culture supernatants. The vertical axis represents a concentration in culture supernatants (ng/mL). The horizontal axis represents hFZD2(X)-hFcm types by X values.

EMBODIMENTS FOR CARRYING OUT THE INVENTION

Figure 1:
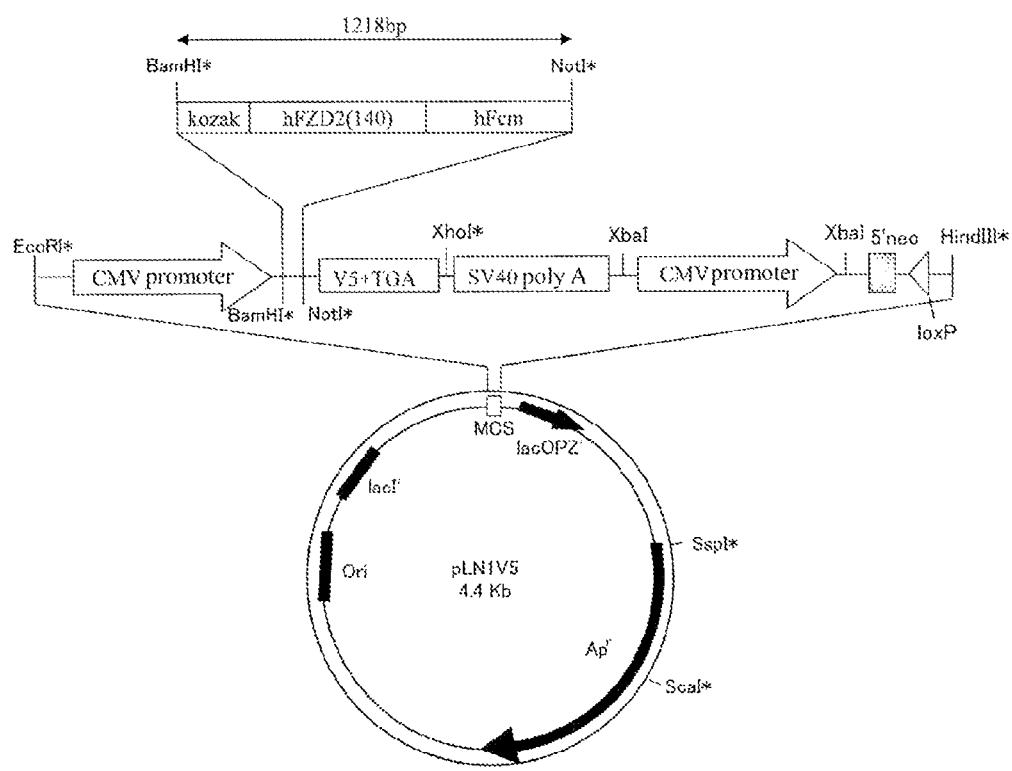
FIG. 1 shows the recombinant expression vector hFZD2 (140)-hFcm. * represents unique sites of restriction enzymes.

Hereinafter, the present invention will be described in detail.

20 amino acids in amino acid sequences shown in the disclosure excluding the sequence lists may be abbreviated as one-letter codes. That is, glycine (Gly) is G, alanine (Ala) is A, valine (Val) is V, leucine (Leu) is L, isoleucine (Ile) is I, phenylalanine (Phe) is F, tyrosine (Tyr) is Y, tryptophane (Trp) is W, serine (Ser) is S, treonine (Thr) is T, cysteine (Cys) is C, methionine (Met) is M, aspartic acid (Asp) is D, glutamic acid (Glu) is E, asparagine (Asn) is N, glutamine (Gln) is Q, lysine (Lys) is K, arginine (Arg) is R, histidine (His) is H, and proline (Pro) is P.

The present invention provides a protein comprising a truncated form of an extracellular region protein derived from a Frizzled 2 receptor from mammals, as mentioned above, and a pharmaceutical composition for treatment of bone diseases containing a vector comprising DNA encoding said protein as an active ingredient.

<Extracellular Region Protein of Frizzled Receptor>

A Frizzled receptor of the present invention is mammalian animal-derived Frizzled 2. Frizzled receptors have an extracellular region protein, and the extracellular region protein has an extracellular cysteine-rich domain. The Frizzled receptors have particularly high identity of extracellular cysteine-rich domains (hereinafter, it is also referred to as "CRD") among ten types of Frizzled receptors whose ligands are Wnt.

In human and mouse, as measured by an amino acid identity from N-terminal first cysteine residue to C-terminal tenth cysteine residue of CRDs of Frizzled receptors, CRD of Frizzled 7 and CRD of Frizzled 2 exhibit 93% identity. Amino acid sequences in the region have the same sequences between human and mouse, and are highly conserved between the species.

Information on amino acid and nucleotide sequences of Frizzled 2 is available from NCBI (USA).

Frizzled 2 (also referred to as "FZD2") is isolated from, for example, human, mouse, rat, or *Xenopus*, and sequence information is open to the public. In the present invention, the origin of the Frizzled 2 protein or a nucleic acid encoding the same is not limited, and it is preferably derived from, for example, a mammalian animal, such as a primate including a human and a rodent including mouse.

Sequence information of human- or mouse-derived Frizzled 2 is registered under, for example, Accession Number: NM 001466. 1, NM 001466.2, or NP 001457.1 in the case of human Frizzled 2, or Accession Number: NM 020510.1, NM 020510.2, NP 065256.1 in the case of mouse FZD2, with the GenBank.

Amino acid sequence of extracellular region protein of human Frizzled 2 is as follows:

Amino acid sequence of extracellular region protein of human Frizzled 2 (SEQ ID NO:1):

QFHGEKGISIPDHGFCQPISIPLCTDIAYNQTIMPNLLGHTNQEDAGLEV

HQFYPLVKVQCSPELRFFLCSMYAPVCTVLEQAIPPCRSICERARQGC

EALMNKFGFQWPERLRCEHFPRHGAEQICVGQNHSEDGAPALLTTAP

PPGLQPGAGGTPGGPGGGGAPPRYATLEHPFHCPRVLKVPSYLSYKFL

GERDCAAPCEPARPDGSMFFSQEETRFAR

The moiety from the 16th amino acid C from N-terminal to the 127th amino acid C from N-terminal corresponds to the sequence from the first cysteine residue on N-terminal side to the tenth cysteine residue on C-terminal side, which represents minimal region sequence of an extracellular cysteine-rich domain (hereinafter, it is also referred to as CRD) (SEQ ID NO:102). Also, at least minimal region sequence of CRD is the same sequence between human and mouse.

SEQ ID NO: 102:
CQPISIPLCTDIAYNQTIMPNLLGHTNQEDAGLEVHQFYPLVKVQCSPEL

RFFLCSMYAPVCTVLEQAIPPCRSICERARQGCEALMNKFGFQWPERL

RCEHFPRHGAEQIC

In the present invention, "an extracellular cysteine-rich domain (CRD)" is a protein which comprises at least amino acid sequences from the first cysteine residue on N-terminal to the tenth cysteine residue in an extracellular region protein of a Frizzled receptor selected from the group consisting of Frizzled 2s derived from mammals and has ability to increase bone mass in mammals.

In this context, "comprise at least" as used herein means that the extracellular cysteine-rich domain may be composed of a minimal region sequence of the cysteine-rich domain (minimal CRD sequence) spanning from the first cysteine residue on N-terminal side to the tenth cysteine residue in an extracellular region protein of a Frizzled receptor, or alternatively may have any foreign sequence added to N-terminal and/or C-terminal of the minimal CRD sequence as long as the sequence has an ability to increase bone mass.

Also, for Frizzled 2, the minimal region sequence of the cysteine-rich domain (minimal CRD sequence) may include amino acid sequence represented by SEQ ID NO:102. In this context, "foreign sequence" may include, for example, a sequence derived from any foreign protein unrelated to the extracellular region protein of the Frizzled receptor, an artificial sequence, or a sequence derived from a portion of the extracellular region protein of a foreign Frizzled receptor other than the minimal CRD sequence.

Alternatively, the extracellular cysteine-rich domain according to the present invention is a protein which comprises an amino acid sequence comprising at least the amino acid sequence spanning from the first cysteine residue on the N-terminal side to the tenth cystein residue in the extracellular region protein of the Frizzled receptor selected from the group consisting of mammalian animal-derived Frizzled 2 and has ability to increase bone mass, bone density and/or bone strength in mammals.

In this context, "comprises at least" as used herein means that the minimal sequence consists of the amino acid sequence spanning the first cystein residue on the N-terminal side to the tenth cysteine residue in the extracellular region protein of the Frizzled receptor, and a sequence derived from the extracellular region protein of the Frizzled receptor of the same species may be adequately extended and comprised at the N-terminus and/or C-terminus of the minimal sequence.

Thus, the extracellular cysteine-rich domain can comprise any amino acid sequence spanning from the aforementioned minimal CRD sequence to the maximal CRD sequence of the extracellular region protein of Frizzled receptor.

<Truncated Form of Extracellular Region Protein of Frizzled Receptor>

In the present invention, "a truncated form of an extracellular region protein of a Frizzled receptor" means a protein comprising at least the first cystein residue on the N-terminal side to the tenth cysteine residue in the extracellular region protein (minimal region sequence of cysteine-rich domain) of an extracellular region protein of Frizzled 2 derived from mammals and having a portion of amino acids of an extracellular region protein of the Frizzled receptor.

In the present invention, a truncated form of an extracellular region protein of Frizzled 2 means a protein comprising the minimal region sequence of cysteine-rich domain represented by SEQ ID NO:102 and having 141 to 175 amino acids in length. The total length of a truncated form of an extracellular region protein of Frizzled 2 has 141 to 175 amino acids, preferably 153 to 175 amino acids.

More preferably, a truncated form of an extracellular region protein of Frizzled 2 is a protein wherein preferably 14 to 48 amino acids, more preferably 26 to 48 amino acids are added to C-terminal of the minimal region sequence of cysteine-rich domain represented by SEQ ID NO:102.

More preferably, a truncated form of an extracellular region protein of Frizzled 2 is any one of said proteins wherein 32, 38, 44 or 48 amino acids are added to C-terminal of the minimal region sequence of cysteine-rich domain represented by SEQ ID NO:102.

Furthermore preferably, a truncated form of an extracellular region protein of Frizzled 2 is any one of said proteins wherein amino acids comprising at least the amino acids from V at position 128 to L at position 141 in the amino acid sequence represented by SEQ ID NO:1 are added to C-terminal of the minimal region sequence of cysteine-rich domain represented by SEQ ID NO:102.

Furthermore preferably, a truncated form of an extracellular region protein of Frizzled 2 is any one of said proteins wherein amino acids of any length selected from the amino acids from T at position 142 to P at position 175 in the amino acid sequence represented by SEQ ID NO:1 are additionally added to C-terminal of the minimal region sequence of cysteine-rich domain represented by SEQ ID NO:102 after L at position 141 in the amino acid sequence represented by SEQ ID NO:1

In this context, "amino acids of any length selected from the amino acids from T at position 142 to P at position 175 in the amino acid sequence represented by SEQ ID NO:1 are added", for example specifically means that any contiguous amino acids selected from the amino acids from T at position 142 to P at position 175 in the amino acid sequence represented by SEQ ID NO:1 are added.

Furthermore preferably, a truncated form of an extracellular region protein of Frizzled 2 is any one of said proteins wherein 1 to 15 amino acids are additionally added to N-terminal of the minimal region sequence of cysteine-rich domain represented by SEQ ID NO:102.

Furthermore preferably, a truncated form of an extracellular region protein of Frizzled 2 is any one of said proteins wherein amino acids of any length selected from the amino acids from Q at position 1 to F at position 15 in the amino acid sequence represented by SEQ ID NO:1 are additionally added to N-terminal of the minimal region sequence of cysteine-rich domain represented by SEQ ID NO:102.

In this context, "amino acids of any length selected from the amino acids from Q at position 1 to F at position 15 in the amino acid sequence represented by SEQ ID NO:1 are added", for example specifically means that any contiguous amino acids selected from the amino acids from Q at position 1 to F at position 15 in the amino acid sequence represented by SEQ ID NO:1 are added.

Furthermore preferably, a truncated form of an extracellular region protein of Frizzled 2 is a protein comprising amino acids from the amino acid Q at position 1 of N-terminal to any one amino acid of A at position 153, G at position 154, G at position 155, T at position 156, P at position 157, G at position 158, G at position 159, P at position 160, G at position 161, G at position 162, G at position 163, G at position 164, A at position 165, P at position 166, P at position 167, R at position 168, Y at position 169, A at position 170, T at position 171, L at position 172, E at position 173, H at position 174, or P at position 175 of the amino acid sequence represented by SEQ ID NO:1.

Furthermore preferably, a truncated form of an extracellular region protein of Frizzled 2 is a protein comprising amino acids from the amino acid Q at position 1 of N-terminal to any one amino acid of G at position 158, G at position 159, P at position 160, G at position 161, G at position 162, G at position 163, G at position 164, A at position 165, P at position 167, R at position 168, Y at position 169, A at position 170, T at position 171, L at position 172, E at position 173, or H at position 174 of the amino acid sequence represented by SEQ ID NO:1.

More preferably, a truncated form of an extracellular region protein of Frizzled 2 is a protein comprising amino acids from the amino acid Q at position 1 of N-terminal to any one amino acid of G at position 158, P at position 160, G at position 161, G at position 162, G at position 163, G at position 164, P at position 167, R at position 168, Y at position 169, A at position 170, T at position 171, or L at position 172 of the amino acid sequence represented by SEQ ID NO:1.

Most preferably, a truncated form of an extracellular region protein of Frizzled 2 is a protein comprising amino acids from the amino acid Q at position 1 of N-terminal to the amino acid R at position 168 of the amino acid sequence represented by SEQ ID NO:1.

Surprisingly, the foregoing proteins comprising truncated forms of an extracellular region protein of Frizzled 2 have improved secretion activity in production cells or equivalent activity compared to known proteins comprising an extracellular cysteine-rich domain of Frizzled 2 (for example, those disclosed in WO 2010/038756 (Patent Literature 3)), as well as bone mass-increasing activity greater than or at least equal to these known proteins.

Particularly, when using the protein comprising amino acids from the amino acid Q at position 1 of N-terminal to any one amino acid of A at position 153, G at position 154, G at position 155, T at position 156, P at position 157, G at position 158, G at position 159, P at position 160, G at position 161, G at position 162, G at position 163, G at position 164, A at position 165, P at position 166, P at position 167, R at position 168, Y at position 169, A at position 170, T at position 171, L at position 172, E at position 173, H at position 174, or P at position 175 of the amino acid sequence represented by SEQ ID NO:1 as a truncated form of an extracellular region protein of Frizzled 2, it was demonstrated that the protein comprising any one of these truncated forms has dramatically improved secretion activity in production cells compared to known proteins comprising an extracellular cysteine-rich domain of Frizzled 2 (for example, those disclosed in WO 2010/038756 (Patent Literature 3)), and/or bone mass-increasing activity greater than or equal to these known proteins.

Further, when using the protein comprising amino acids from the amino acid Q at position 1 of N-terminal to any one amino acid of G at position 158, G at position 159, P at position 160, G at position 161, G at position 162, G at position 163, G at position 164, A at position 165, P at position 167, R at position 168, Y at position 169, A at position 170, T at position 171, L at position 172, E at position 173, or H at position 174 of the amino acid sequence represented by SEQ ID NO:1 as a truncated form of an extracellular region protein of Frizzled 2, it is desirable for dramatically improved secretion activity in production cells and/or bone mass-increasing activity.

Further, when using the protein comprising amino acids from the amino acid Q at position 1 of N-terminal to any one amino acid of G at position 158, P at position 160, G at position 161, G at position 162, G at position 163, G at position 164, P at position 167, Rat position 168, Y at position 169, A at position 170, T at position 171, or L at position 172 of the amino acid sequence represented by SEQ ID NO:1 as a truncated form of an extracellular region protein of Frizzled 2, it was demonstrated that the protein comprising any one of these truncated forms has dramatically improved secretion activity in production cells compared to known proteins comprising an extracellular cysteine-rich domain of Frizzled 2 (for example, those disclosed in WO 2010/038756 (Patent Literature 3)), and/or bone mass-increasing activity greater than or equal to these known proteins.

It is most preferred to use the protein comprising amino acids from the amino acid Q at position 1 of N-terminal to the amino acid R at position 168 of the amino acid sequence represented by SEQ ID NO:1 as a truncated form of an extracellular region protein of Frizzled 2.

In the present invention, "production cells" may include, but not limited to, bacteria such as genus *Escherichia* such as *Escherichia coli*, genus *Bacillus* such as *Bacillus subtilis* or genus *Pseudomonas* such as *Pseudomonas putida*; yeasts such as genus *Saccharomyces* such as *Saccharomyces cerevisiae* or *Schizosaccharomyces pombe*, genus *Candida* or genus *Pichia*; animal cells such as CHO, COS, HEK293, NIH3T3 or NS0; insect cells such as 519 or Sf21; or plant cells. Any cells may be used as long as it can secret or produce proteins of the present invention.

In the present invention, "improved secretion activity" means at least having an higher amount of expression in production cells compared to known proteins comprising an extracellular cysteine-rich domain of Frizzled 2 disclosed in WO 2010/038756 (Patent Literature 3)

In the present invention, "an increase in bone mass" means at least an increase in bone volume/tissue volume. The bone volume/tissue volume refers to the total volume of trabeculars in total tissue volume. An increase in bone volume/tissue volume refers to an increase in bone density.

Also, "an increase in bone mass" may involve an increase in trabecular thickness, an increase in the trabecular number, and/or a decrease in trabecular separation in addition to an increase in bone volume/tissue volume. Herein, the trabecular thickness refers to an average of trabecular thickness, the trabecular number is the trabecular number per unit length, and the trabecular separation is a distance between adjacent trabeculars.

In the present invention, mammals includes primates, livestock animals, rodents, ungulates, pet animals or the like, but not limited thereto. Preferred mammals are human and mouse. Mouse is important in that it has the same sequence as those derived from human in amino acid sequence of its extracellular cysteine-rich domain (CRD), in particular minimal CRD sequence from the first cystein residue on the N-terminal side to the tenth cysteine residue. More preferred mammal is human.

<Mutant of Truncated Form of Extracellular Region Protein>

Mutants of truncated forms of the extracellular region protein of the present invention may include any of natural mutants and artificial mutants, and refer to proteins comprising one or more (preferably one or several) amino acid substitution(s), deletion(s) or addition(s) in the amino acid sequence of the extracellular region protein, or otherwise comprising amino acid sequence which has 80% or more, preferably 85% or more, more preferably 90% or more, for example 93% or more, 95% or more, 97% or more, 98% or more or 99% or more identity to the amino acid sequence of the extracellular region protein, and having ability to improve secretion activity in production cells and increase bone mass.

For example, the mutants comprises one or more (preferably one or several) amino acid substitution(s), deletion(s) or addition(s) in amino acid sequence represented by SEQ ID NO:102 or SEQ ID NO:1, or otherwise comprising amino acid sequence which has 80% or more, preferably 85% or more, more preferably 90% or more, for example 93% or more, 95% or more, 97% or more, 98% or more or 99% or more identity to the subject amino acid sequence, and have ability to improve secretion activity in production cells and increase bone mass.

As used herein, the term "several" represents usually an arbitrary integer from 2 to 10. Preferably, the term "several" represents an arbitrary integer between 2 to 5.

As used herein, the term "identity" means the degree of matching between sequences in the alignment of two amino acid sequences (or nucleotide sequences) when aligning said two sequences such that the number of identical amino acid residues (or the number of nucleotides) becomes maximum. Specifically, it is represented as the percentage (%) of the number of identical amino acid residues (or the number of identical nucleotides) to the total number of amino acid residues (or the total number of nucleotides). When gaps are introduced as in FASTA, the number of gaps is added to the total number of amino acid residues (or the total number of nucleotides).

Proteins having 80% or more, preferably 85% or more sequence identity may be searched using a sequence identity search program such as BLAST or FASTA in sequence database available from NCBI (USA) or EMBL (Europe) (Altschul, S. F. et al., (1990) J. Mol. Biol. 15:403-410; Karlin, S, and Altschul S. F. (1990) Proc. Natl. Acad. Sci. USA 87:2264-2268; and the like).

In BLAST, sequences are divided into words having a fixed length, similar segments are searched in the words, local alignment is performed by extending these segments in both directions until largest similarity is obtained, and finally these segments are combined to perform final alignment.

In FASTA, identical contiguous segments in sequences are rapidly searched, local alignment is performed based on high similarity in these segments, and finally these segments are combined to perform final alignment taking account of gaps.

When a mutation is introduced into the extracellular cysteine-rich domain of the present invention, it is preferable that amino acid residues other than 10 cysteine residues in the sequence spanning the first cystein residue on the N-terminal side to the tenth cysteine residue on the C-terminal side of the extracellular region protein of the Frizzled receptor (minimal CRD sequence) be exclusively subjected to a mutation of substitution, deletion, or addition, natural disulfide bonds be not destructed, and a natural confoimation be substantially maintained.

If a natural disulfide bond(s) in the extracellular cysteine-rich domain is destructed and an inherent conformation is altered, the protein domain may disadvantageously lose or significantly reduce the bone mass, bone density and/or bone strength or greatly reduce the ability.

To introduce mutagenesis, when sequence of the extracellular cysteine-rich domain is known, site-directed mutagenesis using PCR with primers synthesized based on the sequence (including complementary mutant sequence) is preferably used (Kunkel et al., Proc. Natl. Acad. Sci. USA, 1985, 82:488-492; F. M. Ausubel et al., Short Protocols in Molecular Biology, 1995, John Wiley & Sons; J. Sambrook et al., Molecular Cloning: A Laboratory Manual, 2nd ed., 1989, Cold Spring Harbor Laboratory Press; and the like). Commercially available mutagenesis introduction kits (such as those made by Takara Shuzo Co., Ltd.) may also be used according to manufacturer's instruction.

Briefly, the method of Kunkel comprises using a plasmid containing DNA encoding the extracellular cysteinerich domain as a template, annealing a primer having a phosphorylated 5' terminus with T4 DNA polynucleotide kinase (including a complementary mutant sequence) to the template, synthesizing DNA, ligating the terminuses with the aid of T4 DNA ligase, and purifying DNA containing mutation of interest.

In the present invention, the mutation includes a substitution, a deletion, an addition, an insertion, or combinations thereof. Substitution may be conservative or non-conservative. Conservative substitution is preferable in order to substantially refrain from altering the conformation of a protein of the extracellular cysteine-rich domain. refers to substitution across amino acids having similar structural properties (e.g., a branch state or aromaticity), electric properties (e.g., acidic or basic properties), and chemical and physical properties (e.g., polar or hydrophobic properties).

Branched amino acids include valine, leucine and isoleucine. Aromatic amino acids include tyrosine, tryptophane, phenylalanine and histidine. Acidic amino acids include glutamic acid and aspartic acid.

Basic amino acids include lysine, arginine and histidine. Polar amino acids include serine, treonine, glutamine, asparagine, tyrosine, cysteine, glycine, proline and the like. Hydrophobic amino acids include alanine, valine, leucine, isoleucine, methionine and the like.

Deletion involves loss of one or a plurality of amino acid residues. Addition involves binding of one or a plurality of amino acid residues to the protein N- or C-terminus. Insertion involves binding of one or a plurality of amino acid residues to the inside of a protein.

Among these, deletion and insertion can be performed, provided that a protein conformation of the extracellular cysteine-rich domain is not substantially changed. Thus, the number of amino acid residues that can be subjected to deletion or insertion is preferably limited to about 1 to 5.

<Protein Comprising Truncated Form of Extracellular Region Protein or Mutant Thereof>

As discussed above, one of active ingredients used in a pharmaceutical composition of the present invention is a protein comprising a truncated form of an extracellular region protein of mammal-derived Frizzled 2 which has improved secretion activity in production cells and bone mass-increasing activity, or a mutant thereof having 85% or more sequence identity to the truncated form which has also improved secretion activity in production cells and bone mass-increasing activity.

In the present invention, "a truncated form of an extracellular region protein of mammal-derived Frizzled 2" means all of truncated forms of extracellular region protein listed above.

In the present invention, the expression "comprising" means that foreign peptides, polypeptides or proteins may be bound or fused to N-terminal or C-terminal of the above truncated from of an extracellular domain or mutant thereof, via an appropriate peptide linker (for example, 1 to 20 amino acids), if necessary. Preferred examples of such foreign proteins may include mammal-derived immunoglobulin Fc proteins or variants thereof.

However, if such foreign proteins are administrated in vivo, a rejection reaction may occur. Therefore, to avoid such a rejection reaction as much as possible, it is preferred to use proteins inherent to mammals subjected to administration as a foreign protein.

When considering application to human, a preferred Fc protein is a human immunoglobulin Fc proteins. Also, as classes or subclasses of immunoglobulin, but not limited to, for example any of IgG, IgD, IgE, IgM, IgA, IgG1, IgG2, IgG2a, IgG2b, IgG2c, IgG3, IgG4, IgA1 or IgA2 may be used, but when applying to human, it is preferred to use a class or subclass of a human immunoglobulin.

Fc proteins can improve stability of an extracellular cysteine-rich domain or a mutant thereof in vivo. In such a case, however, biological activity, such as antibody dependent cellular cytotoxicity (ADCC) and/or complement dependent cytotoxicity (CDC), of the Fc protein is preferably lowered in advance in order to avoid the influence of such biological activity in vivo. To this end, it is preferred to introduce variations to suppress, reduce or eliminate the above-mentioned bioactivities.

As such variation, there may be any amino acid substitutions to reduce ADCC and/or CDC activity, by substituting for example 1 to 10, preferably 1 to 5, and more preferably 1 to 3 amino acid residues in amino acid sequence of a mammal-derived Fc protein. Specifically, substitutions exemplified in Example 1 below may be included.

A preferred Fc protein is a human IgG1 Fc variant comprising the amino acid sequence represented by SEQ ID NO:3. The Fc proteins may be bound to either one of N-terminal or C-terminal of an extracellular cysteine-rich domain or a mutant thereof, and it is preferred to be bound at C-terminal.

In the present invention, a preferred protein is a fusion protein of a truncated form of an extracellular region protein of Frizzled 2 and a human Fc protein.

In the present invention, a preferred protein is a protein comprising a fusion of a truncated form of an extracellular region protein of Frizzled 2 and a human Fc protein, wherein a fusion protein of a truncated form of an extracellular region protein of Frizzled 2 comprising amino acids from the amino acid Q at position 1 of N-terminal to any one amino acid of A at position 153, G at position 154, G at position 155, T at position 156, P at position 157, G at position 158, G at position 159, P at position 160, G at position 161, G at position 162, G at position 163, G at position 164, A at position 165, P at position 166, P at position 167, R at position 168, Y at position 169, A at position 170, T at position 171, L at position 172, E at position 173, H at position 174, or P at position 175 of the amino acid sequence represented by SEQ ID NO:1 and a human Fc protein.

A more preferred protein is a protein comprising a fusion of a truncated form of an extracellular region protein of Frizzled 2 and a human Fc protein, wherein a fusion protein of a truncated form of an extracellular region protein of Frizzled 2 comprising amino acids from the amino acid Q at position 1 of N-terminal to any one amino acid of G at position 158, G at position 159, P at position 160, G at position 161, G at position 162, G at position 163, G at position 164, A at position 165, P at position 167, R at position 168, Y at position 169, A at position 170, T at position 171, L at position 172, E at position 173, or H at position 174 of the amino acid sequence represented by SEQ ID NO:1 and a human Fc protein.

An even more preferred protein is a protein comprising a fusion of a truncated form of an extracellular region protein of Frizzled 2 and a human Fc protein, wherein a fusion protein of a truncated form of an extracellular region protein of Frizzled 2 comprising amino acids from the amino acid Q at position 1 of N-terminal to any one amino acid of G at position 158, P at position 160, G at position 161, G at position 162, G at position 163, G at position 164, P at position 167, R at position 168, Y at position 169, A at position 170, T at position 171, or L at position 172 of the amino acid sequence represented by SEQ ID NO:1 and a human Fc protein.

A most preferred protein is a protein comprising a fusion of a truncated form of an extracellular region protein of Frizzled 2 and a human Fc protein, wherein a fusion protein of a truncated form of an extracellular region protein of Frizzled 2 comprising amino acids from the amino acid Q at position 1 of N-terminal to the amino acid R at position 168 in the amino acid sequence represented by SEQ ID NO:1 and a human Fc protein.

More particularly, a fusion protein of a truncated form of an extracellular region protein of Frizzled 2 and a human Fc protein is a protein comprising amino acids represented by any one of SEQ ID NOs:72 to 94.

More preferably, a fusion protein of a truncated form of an extracellular region protein of Frizzled 2 and a human Fc protein is a protein comprising amino acids represented by any one of SEQ ID NOs:77 to 84 and 86 to 93.

More preferably, a fusion protein of a truncated form of an extracellular region protein of Frizzled 2 and a human Fc protein is a protein comprising amino acids represented by any one of SEQ ID NOs:77, 79 to 83 and 86 to 91. Most preferably, a fusion protein of a truncated form of an extracellular region protein of Frizzled 2 and a human Fc protein is a protein comprising the amino acids represented by SEQ ID NO:87.

Truncated forms of an extracellular region protein of a fusion protein, which comprise amino acid sequence represented by any one of SEQ ID NOs:72 to 94 are derived from the extracellular region protein of Frizzled 2. The amino acid sequence for each truncated form may comprise variations as described in the above section <Mutant of truncated form of extracellular region protein> as long as the protein has ability to increase bone mass.

Surprisingly, the foregoing fusion proteins comprising truncated forms of an extracellular region protein of Frizzled 2 have improved secretion activity in production cells or equivalent activity compared to known fusion proteins comprising an extracellular cysteine-rich domain of Frizzled 2 (for example, those disclosed in WO 2010/038756 (Patent Literature 3)), as well as bone mass-increasing activity greater than or at least equal to these known proteins.

For a fusion protein comprising a truncated form of an extracellular region protein of Frizzled 2, particularly, when using the protein comprising amino acids from the amino acid Q at position 1 of N-terminal to any one amino acid of A at position 153, G at position 154, G at position 155, T at position 156, P at position 157, G at position 158, G at position 159, P at position 160, G at position 161, G at position 162, G at position 163, G at position 164, A at position 165, P at position 166, P at position 167, R at position 168, Y at position 169, A at position 170, T at position 171, L at position 172, E at position 173, H at position 174, or P at position 175 of the amino acid sequence represented by SEQ ID NO:1 as the truncated form of an extracellular region protein of Frizzled 2, it was demonstrated that a fusion protein comprising any one of these truncated forms has dramatically improved secretion activity in production cells compared to known fusion proteins comprising an extracellular cysteine-rich domain of Frizzled 2 (for example, those disclosed in WO 2010/038756 (Patent Literature 3)), and/or bone mass-increasing activity greater than or equal to these known proteins.

Further, for the fusion protein, when using the protein comprising amino acids from the amino acid Q at position 1 of N-terminal to any one amino acid of G at position 158, G at position 159, P at position 160, G at position 161, G at position 162, G at position 163, G at position 164, A at position 165, P at position 167, R at position 168, Y at position 169, A at position 170, T at position 171, L at position 172, E at position 173, or H at position 174 of the amino acid sequence represented by SEQ ID NO:1, it is desirable for dramatically improved secretion activity in production cells, and/or bone mass-increasing activity.

Further, when using the protein comprising amino acids from Q at position 1 of N-terminal to any one amino acid of G at position 158, P at position 160, G at position 161, G at position 162, G at position 163, G at position 164, P at position 167, R at position 168, Y at position 169, A at position 170, T at position 171, or L at position 172 of the amino acid sequence represented by SEQ ID NO:1 in the fusion protein, it was demonstrated that a fusion protein comprising any one of these truncated forms has dramatically improved secretion activity in production cells compared to known fusion proteins comprising an extracellular cysteine-rich domain of Frizzled 2 (for example, those disclosed in WO 2010/038756 (Patent Literature 3)), as well as bone mass-increasing activity greater than or equal to these known proteins.

Most preferably, a fusion protein is a fusion of the truncated form of an extracellular region protein of Frizzled 2 comprising amino acids from the amino acid Q at position 1 of N-terminal to the amino acid R at position 168 of the amino acid sequence represented by SEQ ID NO:1 and a human Fc protein.

Further, as shown in Examples, it was demonstrated that a fusion protein comprising any one of the amino acid sequences represented by SEQ ID NOs:72 to 94 has surprising effects as described above.

Even more preferably, a fusion protein of a truncated form of an extracellular region protein of Frizzled 2 and a human Fc protein is a protein comprising any one of the amino acid sequences represented by SEQ ID NOs:77 to 84 and 86 to 93.

Even more preferably, a fusion protein of a truncated form of an extracellular region protein of Frizzled 2 and a human Fc protein is a protein comprising any one of the amino acid sequences represented by SEQ ID NOs:77, 79 to 83 and 86 to 91. Most preferably, a fusion protein of a truncated form of an extracellular region protein of Frizzled 2 and a human Fc protein is a protein comprising the amino acid sequence represented by SEQ ID NO:87.

In the present invention, "production cells" may include, but not limited to, bacteria of the genus *Escherichia* such as *E. coli*, the genus *Bacillus* such as *Bacillus subtilis*, and the genus *Pseudomonas* such as *Pseudomonas putida*; yeast of the genus *Saccharomyces* such as *Saccharomyces cerevisae* and *Schizosaccharomyces pombe*, the genus *Candida*, and the genus *Pichia*; animal cells, such as CHO, COS, HEK293, NIH3T3, and NS0; insect cells, such as Sf9 and Sf21; and plant cells. Any cells may be used as long as it can secret or produce proteins of the present invention.

In the present invention, "improved secretion activity" means that at least an amount of expression in production cells is higher than those of known fusion proteins comprising an extracellular cysteine-rich domain of Frizzled 2 disclosed in WO 2010/038756 (Patent Literature 3).

In the present invention, "an increase in bone mass" involves at least an increase in bone volume/tissue volume.

In the present invention, a protein comprising the truncated form of extracellular region protein or a mutant thereof may be not bound or fused to foreign peptides, polypeptides or proteins. That is, the protein of the present invention may be a fragment comprising the aforementioned extracellular region protein, as a fragment of the above-mentioned extracellular region protein of Frizzled 2 receptor. Such a fragment may comprise variations as described in the above Section <Mutant of truncated form of extracellular region protein> as long as it has ability to increase bone mass, bone density and/or bone strength.

A protein comprising the truncated form of extracellular region protein or a mutant thereof of the present invention may be produced by gene recombination technique known in the art. In a brief explanation, the protein may be produced by preparing DNA encoding the protein of the present invention, constructing an expression vector containing the DNA, transforming or transfecting prokaryotic or eukaryotic cells with the vector, and recovering a recombined target protein from a culture solution of the cells.

The resulting protein may be purified by using common purification methods including ammonium sulfate precipitation, organic solvent precipitation, dialysis, electrophoresis, chromatofocusing, gel filtration chromatography, ion exchange chromatography, affinity chromatography or HPLC, or any combination thereof.

The DNA and the vector mentioned above are as described in the above <Nucleic acid and vector> and Examples below. Gene recombination techniques described in, for example, F. M. Ausubel et al., Short Protocols in Molecular Biology, 1995 or John Wiley & Sons, J. Sambrook et al., Molecular Cloning: A Laboratory Manual, 2nd ed., 1989, Cold Spring Harbor Laboratory Press can be applied to the present invention.

In the present invention, a protein comprising the truncated form of extracellular region protein or a mutant thereof may be chemically modified.

Examples of such chemical modification may include, but not limited to, glycosylation, pegylation (PEGylation), acetylation, amidation, phosphorylation or the like. Glycosylation and pegylation may be particularly preferred.

"Pegylation" refers to binding of one or a plurality of polyethylene glycol (PEG) molecules to, for example, an amino acid residue, such as an N-terminal amino group of a protein or a ε-amino group of lysine (Lys). In general, a PEG molecule is bound to a free amino group of an amino acid.

An average molecular weight of PEG can be in the range of, but not limited to, about 3,000 to about 50,000. PEG can be bound to a protein by introducing an active group, such as a carboxyl, formyl(aldehyde), N-hydroxysuccinimide ester, amino, thiol, or maleimide group, to a terminus of PEG and allowing such group to react with a group of a protein, such as an amino, carboxyl, thiol, or hydroxyl group.

"Glycosylation (sugar chain binding)" refers to binding of a carbohydrate chain (i.e., a sugar chain) to an asparagine, serine, or threonine residue of a protein. In general, glycosylation takes place upon recognition of an Asn-X-Thr/Ser sequence (wherein X represents an amino acid residue other than Pro). When an amino acid sequence of the protein is modified so as to have such sequence, a sugar chain can be introduced into a site that is different from that of a naturally-occurring protein.

In general, a nucleic acid encoding a recombinant protein is expressed in an eukaryotic cell (e.g., an yeast, animal, or plant cell) via genetic recombination to cause glycosylation of a recombinant protein. In the present invention, a sugar chain structure is not particularly limited, and it is considered to differ depending on a type of a cell selected for expression. When used for a human, a human-derived cell, an yeast cell capable of synthesizing a human sugar chain, a Chinese hamster ovary (CHO) cell, or the like can be used.

It is preferable that acetylation or amidation be mainly carried out at the protein N- or C-terminus. Such reaction can be carried out with the use of, for example, an alcohol, such as aliphatic alcohol or fatty acid, or a carboxylic acid. The number of carbon atoms in the alkyl moiety is, for example, about 1 to 20; however, conditions in terms of water-solubility and avirulence need to be satisfied.

<Nucleic Acid and Vector>

As an active ingredient of a composition of the present invention, vectors comprising nucleic acids encoding a protein comprising the truncated forms of extracellular region protein and mutants thereof are also included.

In the present invention, "nucleic acid" includes both DNA and RNA. DNA includes genomic DNA or cDNA, and RNA includes mRNA.

With respect to the truncated form of extracellular region protein, the mutant thereof and the protein comprising the same, including the fusion protein with Fc protein, are as described in the above sections of <Truncated form of extracellular region protein of Frizzled receptor>, <Mutant of truncated form of extracellular region protein> and <Protein comprising truncated form or mutant thereof of extracellular region protein>, and all descriptions made in such sections are employed herein. Accordingly, "nucleic acid" used in the present invention encompasses the nucleic acid encoding a protein comprising the extracellular cysteine-rich domain or a mutant thereof specifically described above.

Specifically, DNAs include DNAs encoding amino acid sequence comprising CRD minimal sequence (SEQ ID NO:102) comprising at least from N-terminal the first cysteine residue to C-terminal the tenth cysteine residue in amino acid sequence of the extracellular region protein (SEQ ID NO:1) of human Frizzled 2.

In view of DNAs expression in an eukaryotic cell and extracellular secretion of the expression product, it is preferable that a nucleotide sequence encoding a signal sequence be further included. Examples of signal sequences include a signal sequence derived from a Frizzled receptor protein, a signal sequence derived from human CD33, a signal sequence derived from human serum albumin, and a signal sequence derived from human preprotrypsin.

More specifically, DNAs of the present invention may include the following sequences.

```
DNA encoding Human Frizzled 2 extracellular
region protein (SEQ ID NO: 2):
CAGTTCCACGGGGAGAAGGGCATCTCCATCCCGGACCACGGCTTCTGCC

AGCCCATCTCCATCCCGCTGTGCACGGACATCGCCTACAACCAGACCAT

CATGCCCAACCTTCTGGGCACACGAACCAGGAGGACGCAGGCCTAGAG

GTGCACCAGTTCTATCCGCTGGTGAAGGTGCAGTGCTCGCCCGAACTGC

GCTTCTTCCTGTGCTCCATGTACGCACCCGTGTGCACCGTGCTGGAACA

GGCCATCCCGCCGTGCCGCTCTATCTGTGAGCGCGCGCGCCAGGGCTGC

GAAGCCCTCATGAACAAGTTCGGTTTTCAGTGGCCCGAGCGCCTGCGCT

GCGAGCACTTCCCGCGCCACGGCGCCGAGCAGATCTGCGTCGGCCAGAA

CCACTCCGAGGACGGAGCTCCCGCGCTACTCACCACCGCGCCGCCGCCG

GGACTGCAGCCGGGTGCCGGGGGCACCCCGGGTGGCCCGGGCGGCGGCG

GCGCTCCCCGCGCTACGCCACGCTGGAGCACCCCTTCCACTGCCCGCG

CGTCCTCAAGGTGCCATCCTATCTCAGCTACAAGTTTCTGGGCGAGCGT

GATTGTGCTGCGCCCTGCGAACCTGCGCGGCCCGATGGTTCCATGTTCT

TCTCACAGGAGGAGACGCGTTTCGCGCGC
```

In the present invention, a DNA includes a DNA encoding a fusion protein of a protein comprising the truncated form of extracellular region protein of Frizzled receptor or a mutant thereof and a foreign protein as defined above. Preferred example of a foreign protein may include an immunoglobulin Fc protein derived from mammals, and a human Fc protein is particularly preferred. A variation may preferably be introduced into the protein to reduce or eliminate bioactivity thereof (in particular, ADCC and CDC).

For example, nucleotide sequence encoding a variant human IgG1-derived Fc protein is shown in SEQ ID NO:4. Further, preferred sequences as nucleotide sequence encoding a fusion proteins of the variant human IgG1-derived Fc protein and truncated forms of the extracellular region protein of human Frizzled 2 receptor are shown in SEQ ID NOs:42 to 64.

Nucleotide sequence encoding the amino acids of cysteine-rich domain (CRD) (minimal region sequence of CRD) from N-terminal the first cysteine residue to the tenth cysteine residue of the extracellular region protein of human Frizzled 2 is as follows:

```
SEQ ID NO: 103 (Minimal region sequence of CRD of
human Frizzled 2):
TGCCAGCCCATCTCCATCCCGCTGTGCACGGACATCGCCTACAACCAGA

CCATCATGCCCAACCTTCTGGGCCACACGAACCAGGAGGACGCAGGCCT

AGAGGTGCACCAGTTCTATCCGCTGGTGAAGGTGCAGTGCTCGCCCGAA

CTGCGCTTCTTCCTGTGCTCCATGTACGCACCCGTGTGCACCGTGCTGG

AACAGGCCATCCCGCCGTGCCGCTCTATCTGTGAGCGCGCGCGCCAGGG
```

-continued
```
CTGCGAAGCCCTCATGAACAAGTTCGGTTTTCAGTGGCCCGAGCGCCTG

CGCTGCGAGCACTTCCCGCGCCACGGCGCCGAGCAGATCTGC
```

The above nucleotide sequences encoding fusion proteins may additionally include nucleotide sequences encoding signal sequences. Examples of signal sequences may include signal sequences derived from human proteins such as human Frizzled 2, signal sequences derived from human CD33, signal sequences derived from human serum albumin, signal sequences derived from human preprotrypsin or the like.

Homologs of nucleic acids encoding the proteins can be obtained from cDNA libraries prepared from cells or tissues that are known to express genes derived from mammalian animals other than humans via well-known techniques involving the use of primers or probes prepared based on cDNAs synthesized from mRNAs encoding the human derived Frizzled 2 genes. Examples of such techniques include PCR and hybridization (e.g., Southern or Northern hybridization).

PCR stands for a polymerase chain reaction, which involves about 25 to 40 cycles of a reaction cycle comprising a denaturing process for dissociating double-stranded DNA into single-stranded DNA (about 94° C. to 96° C. for about 30 seconds to 1 minute), an annealing process for binding a primer to template single-stranded DNA (about 55° C. to 68° C. for about 30 seconds to 1 minute), and an extension process for extending a DNA strand (about 72° C. for about 30 seconds to 1 minute).

Also, a pre-heating process can be carried out at about 94° C. to 95° C. for about 5 to 12 minutes prior to the denaturing process and another extension reaction can be carried out at 72° C. for about 7 to 15 minutes after the final cycle of the extension process. PCR is carried out using a commercially available thermal cycler in a PCR buffer containing, for example, thermostable DNA polymerase (e.g., AmpliTaq Gold® (Applied Biosystems)), $MgCl_2$, and dNTP (e.g., dATP, dGTP, dCTP, or dTTP) in the presence of sense and antisense primers (size: about 17 to 30 bases, preferably 20 to 25 bases) and template DNA. Amplified DNA can be separated and purified via agarose gel electrophoresis (ethidium bromide staining).

Hybridization is a technique comprising forming a double strand with an about 20 to 100 bases or longer label probe and detecting a target nucleic acid. In order to enhance selectivity, hybridization can be generally carried out under stringent conditions.

Under stringent conditions, for example, hybridiztion is carried out in the presence of about 1 to 5×SSC at room temperature to about 40° C., and washing is then carried out in the presence of about 0.1 to 1×SSC and 0.1% SDS at about 45° C. to 65° C. The term "1×SSC" used herein refers to a solution comprising 150 mM NaCl and 15 mM Na-citrate (pH 7.0). Under such conditions, nucleic acids having sequence identity of 80% or higher, and preferably 85% or higher, can be detected.

The DNA is inserted into a vector, and the resulting vector is used for the production of a protein as an active ingredient of the pharmaceutical composition of the present invention, or such vector is formulated into and used for a pharmaceutical composition.

Examples of such a vector may include plasmid, phage or virus vectors. Examples of plasmid may include, but not limited to, *Escherichia coli*-derived plasmid (such as pRSET, pTZ19R, pBR322, pBR325, pUC118 or pUC119),

*Bacillus subtilis*-derived plasmid (such as pUB110 or pTP5), yeast-derived plasmid (such as YEp13, YEp24 or YCp50), Ti plasmid and the like.

Examples of phage may include λ phage and the like. Examples of virus vectors may include animal virus vectors, such as retrovirus, vaccinia virus, lentivirus, adenovirus, and adeno-associated virus vectors, and insect virus vectors, such as a baculovirus vector.

Such vector may comprise a polylinker or a multicloning site to introduce a target DNA, and also may comprise several control elements to express the target DNA. Examples of control elements may include promoters, enhancers, poly A addition signals, replication origins, selective markers, liposome binding sequences, terminators or the like.

Examples of selection markers include drug-resistant genes (e.g., neomycin-resistant genes, ampicillin-resistant genes, kanamycin-resistant genes, and puromycin-resistant genes) and auxotrophic complementary genes (e.g., dihydrofolate reductase (DHFR) genes, HIS3 genes, LEU2 genes, and URA3 genes).

Promoters occasionally vary depending on host cells. Examples of host cells include, but are not limited to: bacteria of the genus *Escherichia* such as *E. coli*, the genus *Bacillus* such as *Bacillus subtilis*, and the genus *Pseudomonas* such as *Pseudomonas putida*; yeast of the genus *Saccharomyces* such as *Saccharomyces cerevisae* and *Schizosaccharomyces pombe*, the genus *Candida*, and the genus *Pichia*; animal cells, such as CHO, COS, HEK293, NIH3T3, and NS0; insect cells, such as Sf9 and Sf21; plant cells and the like.

When bacterial host cells such as *E. coli* cells are used, examples of promoters include trp promoters, lac promoters, and PL or PR promoters.

When yeast hosts are used, examples of promoters include gall promoters, gal 10 promoters, heat shock protein promoters, MFα1 promoters, PHO5 promoters, PGK promoters, GAP promoters, ADH promoters, AOX1 promoters and the like.

When animal host cells are used, examples of promoters include SRα promoter, SV40 promoter, LTR promoter, CMV promoter, human CMV early gene promoter, adenovirus late promoter, vaccinia virus 7.5K promoter, metallothionein promoter, polyhedrin promoter or the like.

When plant host cells are used, examples of promoter include CaMV promoter, TMV promoter or the like.

Examples of methods for transformation or transfection include electroporation, the spheroplast method, the lithium acetate method, the calcium phosphate method, the *Agrobacterium* method, the virus infection method, the liposome method, microinjection, the gene gun, lipofection and the like.

The transformed host cells are cultured under the conditions that are suitable for types of bacteria, yeast, animal cells, or plant cells, and target proteins are recovered from the cells or the culture solution.

Microorganisms are cultured with the use of a medium containing carbon sources, nitrogen sources, inorganic salts, and the like assimilable by microorganisms. Examples of carbon sources that can be used include carbohydrates, such as glucose, fructose, sucrose, starch and the like, organic acids, such as acetic acid, propionic acid and the like, and alcohols, such as ethanol, propanol and the like.

Examples of nitrogen sources that can be used include ammonium salts of inorganic acids or organic acids, such as ammonia, ammonium chloride, ammonium sulfate, ammonium acetate, and ammonium phosphate, peptone, meat extract, corn steep liquor and the like.

Examples of inorganic substances that can be used include monopotassium phosphate, dipotassium phosphate, magnesium phosphate, magnesium sulfate, sodium chloride, ferrous sulfate, manganese sulfate, copper sulfate, calcium carbonate and the like.

Animal cells may be cultured by using DMEM, RPMI1640 medium or the like as base medium which is supplemented with substances such as bovine fetus serum (FCS) and the like.

A target protein can be recovered by common methods used in protein purification as described above, including ammonium sulfate precipitation, organic solvent precipitation, dialysis, electrophoresis, chromatofocusing, gel filtration chromatography, ion exchange chromatography, affinity chromatography, HPLC and the like.

When a vector is used for a therapeutic purpose, a vector that is not incorporated into the subject's genome and is a virus or non-virus vector capable of infecting cells but is unreplicable is preferable. Examples of such vector include an adeno-associated virus vector and an adenovirus vector. These vectors may contain a promoter, an enhancer, a polyadenylation site, a selection marker, a reporter gene and the like.

Examples of virus vectors are vectors as listed in J. Virol. 67:5911-5921 (1993), Human Gene Therapy 5:717-729 (1994), Gene Therapy 1:51-58 (1994), Human Gene Therapy 5:793-801 (1994) or Gene Therapy 1:165-169 (1994); or improved vectors thereof.

Further, examples of nonvirus vectors include human artificial chromosome vectors that are composed of a chromosome fragment comprising human chromosome-derived ceturomere and telomere. Examples of human chromosome fragments include, but are not particularly limited to, a human chromosome 14 fragment and a human chromosome 21 fragment (e.g., JP Patent Publication (saihyo) No. 2004-031385 A and JP Patent Publication (kokai) No. 2007-295860 A).

The above-defined DNA is inserted into such the vector, and the DNA-inserted vector is administrated to a bone portion of a subject. Alternatively, the vector is introduced into a bone tissue or a cell obtained from a subject, and the bone tissue or cell is returned to the subject.

<Production Method of Protein Comprising Truncated Form of Extracellular Region Protein of Frizzled 2>

The present invention provides a method of producing a protein comprising a truncated form of an extracellular region protein of Frizzled 2. Specifically, the protein comprising a truncated form of an extracellular region protein of Frizzled 2 can be produced by using the above-mentioned DNA, vector, selective marker, promoter, host cell, transformant cell culture of microbes (including culture of animal cells), recover of target protein and the like, as well as methods known in the art.

<Pharmaceutical Composition>

Also, the present invention provides a composition for treating a bone disease comprising, as an active ingredient, a protein comprising a truncated form or a mutant thereof of an extracellular region protein of Frizzled 2 receptor as described above or a vector containing DNA encoding said protein.

Also, the present invention provides a method for treating a bone disease comprising administrating the above-mentioned composition for treating a bone disease to mammals.

In the present invention, the bone disease includes a disease involving a decrease in bone mass, bone density, and/or bone strength., for example osteoporosis, arthritis deformans, rheumatoid arthritis, malignant tumors, hypercalcemia, Paget disease of bone, marble disease, Camurati-Engelmann's disease, arthropathy, primary hyperthyroidism, osteopenia, osteoporosis, osteomalacia, rickets, bone diseases due to traumatic fracture or fatigue fracture, and related various bone diseases or disorders.

Examples of the malignant tumor includes osteoclastoma, osteosarcoma or multiple myeloma. Bone pain in multiple myeloma may be primarily exhibited in spinal cord and rib, and may be exacerbated due to exercise. If pain is sustained in the same site, pathologic fracture might occur. If there is a lesion in spine, spinal cord compression may be caused.

In multiple myeloma, IL-6 is released by proliferated tumor cells. IL-6 has been known as an osteoclast activating factor (OAF). As bone is absorbed and destroyed by IL-6-activated osteoclasts, X-ray photograph of bone suffering from multiple myeloma shows holes in bone (Punching image: "punched-out" resorptive lesions). Also, a concentration of calcium in blood due to bone destruction is increased, and hypercalcemia and various symptoms attributed to the hypercalcemia occur.

Osteoporosis includes primary osteoporosis and secondary osteoporosis. Examples of primary osteoporosis may include postmenopausal osteoporosis or age-related osteoporosis. Examples of secondary osteoporosis may include endocrinic (such as hyperparathyroidism, hyperthyroidism, hypogonadism, Cushing's syndrome, growth hormone deficiency, diabetes mellitus, Addison's disease and calcitonin deficiency); nutritional/metabolic (such as chronic wasting diseases, emaciation, severe hepatic diseases (particularly primary inflammatory liver cirrhosis), gastrectomy, scurvy, malabsorption syndrome (including celiac disease), hypophosphatemia, chronic renal diseases, idiopathic hypercalciuria, hemochromatosis, amyloidosis, mastocytoma, excessive sodium intake, calcium deficiency and D, A-hypervitaminosis); inflammatory (such as rheumatoid arthritis, periarticular osteoporosis (bone resorption enhancement by inflammatory cytokines) and sarcoidosis); immotile (such as systemic, bed ridden, paralysis, topical and postfracture disorders); drug-induced diseases (such as steroids (Immunosuppressive drugs which are widely used in inflammatory diseases; Diseases treated with steroids include collagen disease, asthma, ulcerative colitis and organ transplantation. Bone loss is a severe side effect due to this therapy), methotrexate, heparin, warfarin, anticonvulsants, lithium and tamoxifen); hematologic (such as multiple myeloma, lymphoma, leukemia, hemophilia and chronic hemolytic diseases); congenital (such as osteogenesis imperfecta, Marfan syndrome, Klinefelter's syndrome, congenital erythropoietic porphyria and cystic fibrosis); and other causative diseases (such as chronic obstructive pulmonary diseases, hepatic diseases, renal diseases, rheumatoid arthritis, pregnancy, hyperoxia and HIV infection).

Also, in the present invention, the bone disease includes a bone disease caused due to inhibition of only a calcification process such as rickets.

According to the present invention, a composition for treating a bone disease acts, specifically on bone portions, to increase bone mass, bone density and/or bone strength, when it is administered to mammals with a bone disease, preferably the mammals with a disease involving the decrease of bone mass, bone density and/or bone strength. The composition at least enables increase in the cancellous bone and thickening and proliferation of the diaphysis. Thus, as the composition for treating bone diseases of the present invention is specific to bone portions, it has a surprising advantage that it causes no or little side effect on other tissues.

EXAMPLES

Example 1

1-1. Production of hFZD2-hFcm

For a fusion protein of a truncated form of human Frizzled 2 extracellular region protein and a human IgG1Fc variant (hereinafter, hFZD2-hFcm), fusion proteins were produced using truncated forms having different amino acid length of the extracellular region protein and the human IgG1Fc variant.

Specifically, total 31 truncated forms of Frizzled 2 extracellular region protein were produced with respect to the truncated form of human Frizzled 2 extracellular region protein, and each of these truncated forms had amino acids from the amino acid at position 1 of N-terminal to any one of amino acids at positions 140, 153, 154, 155, 156, 157, 158, 159, 160, 161, 162, 163, 164, 165, 166, 167, 168, 169, 170, 171, 172, 173, 174, 175, 178, 184, 190, 197, 210, 216 or 222 of Frizzled 2 extracellular region protein represented by SEQ ID NO:1.

Hereinafter, fusion proteins of truncated forms of human Frizzled 2 extracellular region protein, which have each of amino acid lengths listed above, and the human IgG1Fc variant are designated as hFZD2(X)-hFcm, and a length of amino acids is denoted in parentheses.

```
SEQ ID NO: 1 (Amino acid sequence of human Frizzled
2 extracellular region protein):
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVPSYLSYKFLGERDCAAPCEPARPDGSMFFSQEETRFAR SEQ ID NO: 2 (Nucleotide sequence of DNA encoding
human Frizzled 2 extracellular region protein):
CAGTTCCACGGGGAGAAGGGCATCTCCATCCCGGACCACGGCTTCTGCCAGCCCA
TCTCCATCCCGCTGTGCACGGACATCGCCTACAACCAGACCATCATGCCCAACCTT
CTGGGCCACACGAACCAGGAGGACGCAGGCCTAGAGGTGCACCAGTTCTATCCG
CTGGTGAAGGTGCAGTGCTCGCCCGAACTGCGCTTCTTCCTGTGCTCCATGTACGC
ACCCGTGTGCACCGTGCTGGAACAGGCCATCCCGCCGTGCCGCTCTATCTGTGAG
CGCGCGCGCCAGGGCTGCGAAGCCCTCATGAACAAGTTCGGTTTTCAGTGGCCCG
AGCGCCTGCGCTGCGAGCACTTCCCGCGCCACGGCGCCGAGCAGATCTGCGTCG
GCCAGAACCACTCCGAGGACGGAGCTCCCGCGCTACTCACCACCGCGCCGCCGC
CGGGACTGCAGCCGGGTGCCGGGGGCACCCCGGGTGGCCCGGGCGGCGGCGGC
GCTCCCCCGCGCTACGCCACGCTGGAGCACCCCTTCCACTGCCCGCGCGTCCTCA
```

-continued
```
AGGTGCCATCCTATCTCAGCTACAAGTTTCTGGGCGAGCGTGATTGTGCTGCGCCC
TGCGAACCTGCGCGGCCCGATGGTTCCATGTTCTTCTCACAGGAGGAGACGCGTT
TCGCGCGC SEQ ID NO: 3 (Amino acid sequence of human IgG1Fc variant):
AEPRSSDKTHTCPPCPAPEAEGAPSVFLFPPKPKDTLMISRTPEVTCVVVDVSHEDPEV
KFNWYVDGVEVHNAKTKPREEQYNSTYRVVSVLTVLHQDWLNGKEYKCAVSNKA
LPASIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSL
SPGK SEQ ID NO: 4 (Nucleotide sequence of DNA encoding human
IgG1Fc variant):
GCCGAGCCTAGGTCTTCAGACAAAACTCACACATGCCCACCGTGCCCAGCACCTG
AAGCCGAGGGGGCCCCGTCAGTCTTCCTCTTCCCCCCAAAACCCAAGGACACCCT
CATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCA
AGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCGCCGTCTC
CAACAAAGCCCTCCCAGCCTCCATCGAGAAAACCATCTCCAAAGCCAAAGGGCA
GCCCCGAGAACCACAGGTGTACACCCTGCCCCCATCCCGGGATGAGCTGACCAAG
AACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAG
CAGGTGGCAGCAGGGGAACGTCTTCTCATGCTCCGTGATGCATGAGGCTCTGCAC
AACCACTACACGCAGAAGAGCCTCTCCCTGTCTCCGGGTAAATGA
```

1-1-1. Construction of pLN1V5 Vector

Sense oligo DNA (V5S) having the BamHI, NheI, and SalI sites at the 5' terminus and the XhoI site at the 3' terminus (a V5 tag and a stop codon) and corresponding antisense oligo DNA (V5AS) were synthesized.

```
V5S:
                                        (SEQ ID NO: 5)
GATCCGCTAGCGTCGACGGTAAGCCTATCCCTAACCCTCTCCTCGGTCTC
GATTCTACGTGAC

V5AS:
                                        (SEQ ID NO: 6)
TCGAGTCACGTAGAATCGAGACCGAGGAGAGGGTTAGGGATAGGCTTACC
GTCGACGCTAGCG
```

Oligo DNA synthesized above was introduced into the BamHI-XhoI site on the pLN1 vector described in the report of Kakeda et al. (Gene Ther., 12, 852-856, 2005) to construct the pLN1V5 vector.

1-1-2. Synthesis of hFZD2(140)-hFcm DNA Fragment

```
BHI-kozak-hFZD2-F:
                                        (SEQ ID NO: 7)
CGGGATCCACC ATGCGGCCCCGCAGCGCCC hFc-NotI-Rv:
                                        (SEQ ID NO: 8)
ATAGTTTAGCGGCCGCTCATTTACCCGGAGACAGG
```

A reaction solution was prepared using Prime STAR HS DNA Polymerase (Takara Bio Inc., Japan) in accordance with the instructions, 10 pmol each primers shown in SEQ ID NOs: 7 and 8 and hFZD2(140)-hFcm (SEQ ID NO: 9) as a template were added to 50 µl of the reaction solution, the resultant was incubated at 98° C. for 1 minute, an amplification cycle of 98° C. for 10 seconds, 62° C. for 5 seconds, and 72° C. for 1 minutes was repeated 30 times, and the resulting 1218-bp amplified fragment was separated and recovered with 0.8% gel. The amplified fragment was recovered from the gel using the QIAquick Gel Extraction Kit (Qiagen, Japan) in accordance with the instructions.

1-1-3. Construction of hFZD2(140)-hFcm Recombinant Expression Vector

The PCR-amplified fragment recovered in Example 1-1-2 was digested with the BamHI and NotI restriction enzymes (Roche Diagnostics, K. K., Japan), and the resultant was separated and recovered with 0.8% agarose gel. The enzyme-treated fragment was recovered from the gel using the QIAquick Gel Extraction Extraction Kit (Qiagen, Japan) in accordance with the instructions. A vector was prepared by adding NotI site to pLN1V5 vector from Example 1-1-1. The enzyme treated fragment was introduced into BamHI•NotI site of the above vector to construct the hFZD2 (140)-hFcm recombinant expression vector (FIG. 1).

A polynucleotide sequence (1,191 bp, SEQ ID NO:9) comprising a region from the initiation codon to the termination codon of hFZD2(140)-hFcm recombinant cDNA and the amino acid sequence (396 amino acids, SEQ ID NO:10) comprising a signal sequence of hFZD2(140)-hFcm encoded by the cDNA are shown below.

```
SEQ ID NO: 9:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGCGCCGA
GCAGATCTGCGTCGGCCAGAACCACTCCGAGGACGGAGCTCCCGCGCTAGCCGA
GCCTAGGTCTTCAGACAAAACTCACACATGCCCACCGTGCCCAGCACCTGAAGCC
GAGGGGGCCCCGTCAGTCTTCCTCTTCCCCCCAAAACCCAAGGACACCCTCATGA
TCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGAC
```

-continued
AAAGCCGCGGGAGGAGCAGTACAACAGCACGTACCGTGTGGTCAGCGTCCTCAC
CGTCCTGCACCAGGACTGGCTGAATGGCAAGGAGTACAAGTGCGCCGTCTCCAAC
AAAGCCCTCCCAGCCTCCATCGAGAAAACCATCTCCAAAGCCAAAGGGCAGCCC
CGAGAACCACAGGTGTACACCCTGCCCCCATCCCGGGATGAGCTGACCAAGAACC
AGGTCAGCCTGACCTGCCTGGTCAAAGGCTTCTATCCCAGCGACATCGCCGTGGA
GTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACC
ACTACACGCAGAAGAGCCTCTCCCTGTCTCCGGGTAAATGA SEQ ID NO: 10:
MRPRSALPRLLLPLLLLPAAGPAQFHGEKGISIPDHGFCQPISIPLCTDIAYNQTIMPNL
LGHTNQEDAGLEVHQFYPLVKVQCSPELRFFLCSMYAPVCTVLEQAIPPCRSICERAR
QGCEALMNKFGFQWPERLRCEHFPRHGAEQICVGQNHSEDGAPALAEPRSSDKTHT
CPPCPAPEAEGAPSVFLFPPKPKDTLMISRTPEVTCVVVDVSHEDPEVKFNWYVDGV
EVHNAKTKPREEQYNSTYRVVSVLTVLHQDWLNGKEYKCAVSNKALPASIEKTISKA
KGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK 1-1-4. Synthesis of hFZD2(X)-hFcm (X=153-175, 178, 184, 190, 197, 210, 216, 222) DNA Fragments hFZD2-t(153)-AvrII-R:
(SEQ ID NO: 11)
CGCCTAGGCTCGGCGCCACCCGGGGTGCCC hFZD2-t(154)-AvrII-R:
(SEQ ID NO: 12)
CGCCTAGGCTCGGCCCCGGCACCCGGCTGC hFZD2-t(155)-AvrII-R:
(SEQ ID NO: 13)
CGCCTAGGCTCGGCGCCCCCGGCACCCGGC hFZD2-t(156)-AvrII-R:
(SEQ ID NO: 14)
CGCCTAGGCTCGGCGGTGCCCCCGGCACCC hFZD2-t(157)-AvrII-R:
(SEQ ID NO: 15)
CGCCTAGGCTCGGCCGGGGTGCCCCCGGCA hFZD2-t(158)-AvrII-R:
(SEQ ID NO: 16)
CGCCTAGGCTCGGCACCCGGGGTGCCCCCG hFZD2-t(159)-AvrII-R:
(SEQ ID NO: 17)
CGCCTAGGCTCGGCGCCACCCGGGGTGCCC hFZD2-t(160)-AvrII-R:
(SEQ ID NO: 18)
CGCCTAGGCTCGGCCGGGCCACCCGGGGTG hFZD2-t(161)-AvrII-R:
(SEQ ID NO: 19)
CGCCTAGGCTCGGCGCCCGGGCCACCCGGG hFZD2-t(162)-AvrII-R:
(SEQ ID NO: 20)
CGCCTAGGCTCGGCGCCGCCCGGGCCACCC hFZD2-t(163)-AvrII-R:
(SEQ ID NO: 21)
CGCCTAGGCTCGGCGCCGCCGCCCGGGCCA hFZD2-t(164)-AvrII-R:
(SEQ ID NO: 22)
CGCCTAGGCTCGGCGCCGCCGCCGCCCGGG hFZD2-t(165)-AvrII-R:
(SEQ ID NO: 23)
CGCCTAGGCTCGGCAGCGCCGCCGCCGCCC hFZD2-t(166)-AvrII-R:
(SEQ ID NO: 24)
CGCCTAGGCTCGGCGGGAGCGCCGCCGCCG hFZD2-t(167)-AvrII-R:
(SEQ ID NO: 25)
CGCCTAGGCTCGGCCGGGGGAGCGCCGCCG hFZD2-t(168)-AvrII-R:
(SEQ ID NO: 26)
CGCCTAGGCTCGGCGCGCGGGGGAGCGCCG hFZD2-t(169)-AvrII-R:
(SEQ ID NO: 27)
CGCCTAGGCTCGGCGTAGCGCGGGGGAGCG hFZD2-t(170)-AvrII-R:
(SEQ ID NO: 28)
CGCCTAGGCTCGGCGGCGTAGCGCGGGGGA hFZD2-t(171)-AvrII-R:
(SEQ ID NO: 29)
CGCCTAGGCTCGGCCGTGGCGTAGCGCGGG hFZD2-t(172)-AvrII-R:
(SEQ ID NO: 30)
CGCCTAGGCTCGGCCAGCGTGGCGTAGCGC hFZD2-t(173)-AvrII-R:
(SEQ ID NO: 31)
CGCCTAGGCTCGGCCTCCAGCGTGGCGTAG hFZD2-t(174)-AvrII-R:
(SEQ ID NO: 32)
CGCCTAGGCTCGGCGTGCTCCAGCGTGGCG hFZD2-t(175)-AvrII-R:
(SEQ ID NO: 33)
CGCCTAGGCTCGGCGGGGTGCTCCAGCGTG hFZD2-t(178)-AvrII-R:
(SEQ ID NO: 34)
CGCCTAGGCTCGGCGCAGTGGAAGGGGTGC hFZD2-t(184)-AvrII-R:
(SEQ ID NO: 35)
CGCCTAGGCTCGGCCACCTTGAGGACGCGC hFZD2-t(190)-AvrII-R:
(SEQ ID NO: 36)
CGCCTAGGCTCGGCGTAGCTGAGATAGGAT hFZD2-t(197)-AvrII-R:
(SEQ ID NO: 37)
CGCCTAGGCTCGGCATCACGCTCGCCCAGA hFZD2-t(210)-AvrII-R:
(SEQ ID NO: 38)
CGCCTAGGCTCGGCGGAACCATCGGGCCGC hFZD2-t(216)-AvrII-R:
(SEQ ID NO: 39)
CGCCTAGGCTCGGCCTCCTGTGAGAAGAAC hFZD2-t(222)-AvrII-R:
(SEQ ID NO: 40)
CGCCTAGGCTCGGCGCGCGCGAAACGCGTC A reaction solution was prepared using Prime STAR HS DNA Polymerase (TAKARA BIO INC., Japan) in accordance with the instructions, 10 pmol each primers shown in SEQ ID NO:7 as a Fw primer and SEQ ID NOs:11 to 40 as a Rv primer and hFZD2 (SEQ ID NO:41) as a template were added to 50 μl of the reaction solution, the resultant was incubated at 98° C. for 1 minute, an amplification cycle of 98° C. for 10 seconds, 62° C. for 5 seconds, and 72° C. for 1 minutes was repeated 30 times, and the resulting 553-760 bp amplified fragment was separated and recovered with 0.8% gel. The amplified fragment (hFZD2(X)-hFcm) was recovered from the gel using the QIAquick Gel Extraction Kit (Qiagen, Japan) in accordance with the instructions.

SEQ ID NO: 41:
ATGCGGCCCCGCAGCGCCCTGCCCCGCCTGCTGCTGCCGCTGCTGCTGCTGCCCG

CCGCCGGGCCGGCCCAGTTCCACGGGGAGAAGGGCATCTCCATCCCGGACCACG

GCTTCTGCCAGCCCATCTCCATCCCGCTGTGCACGGACATCGCCTACAACCAGACC

ATCATGCCCAACCTTCTGGGCCACACGAACCAGGAGGACGCAGGCCTAGAGGTG

CACCAGTTCTATCCGCTGGTGAAGGTGCAGTGCTCGCCCGAACTGCGCTTCTTCCT

GTGCTCCATGTACGCACCCGTGTGCACCGTGCTGGAACAGGCCATCCCGCCGTGC

CGCTCTATCTGTGAGCGCGCGCGCCAGGGCTGCGAAGCCCTCATGAACAAGTTCG

GTTTTCAGTGGCCCGAGCGCCTGCGCTGCGAGCACTTCCCGCGCCACGGCGCCGA

GCAGATCTGCGTCGGCCAGAACCACTCCGAGGACGGAGCTCCCGCGCTACTCACC

ACCGCGCCGCCGCCGGGACTGCAGCCGGGTGCCGGGGGCACCCCGGGTGGCCCG

GGCGGCGGCGGCGCTCCCCCGCGCTACGCCACGCTGGAGCACCCCTTCCACTGCC

CGCGCGTCCTCAAGGTGCCATCCTATCTCAGCTACAAGTTTCTGGGCGAGCGTGAT

TGTGCTGCGCCCTGCGAACCTGCGCGGCCCGATGGTTCCATGTTCTTCTCACAGG

AGGAGACGCGTTTCGCGCGCCTCTGGATCCTCACCTGGTCGGTGCTGTGCTGCGC

TTCCACCTTCTTCACTGTCACCACGTACTTGGTAGACATGCAGCGCTTCCGCTACC

CAGAGCGGCCTATCATTTTTCTGTCGGGCTGCTACACCATGGTGTCGGTGGCCTAC

ATCGCGGGCTTCGTGCTCCAGGAGCGCGTGGTGTGCAACGAGCGCTTCTCCGAGG

ACGGTTACCGCACGGTGGTGCAGGGCACCAAGAAGGAGGGCTGCACCATCCTCT

TCATGATGCTCTACTTCTTCAGCATGGCCAGCTCCATCTGGTGGGTCATCCTGTCGC

TCACCTGGTTCCTGGCAGCCGGCATGAAGTGGGGCCACGAGGCCATCGAGGCCA

ACTCTCAGTACTTCCACCTGGCCGCCTGGGCCGTGCCGGCCGTCAAGACCATCAC

CATCCTGGCCATGGGCCAGATCGACGGCGACCTGCTGAGCGGCGTGTGCTTCGTA

GGCCTCAACAGCCTGGACCCGCTGCGGGGCTTCGTGCTAGCGCCGCTCTTCGTGT

ACCTGTTCATCGGCACGTCCTTCCTCCTGGCCGGCTTCGTGTCGCTCTTCCGCATC

CGCACCATCATGAAGCACGACGGCACCAAGACCGAAAAGCTGGAGCGGCTCATG

GTGCGCATCGGCGTCTTCTCCGTGCTCTACACAGTGCCCGCCACCATCGTCATCGC

TTGCTACTTCTACGAGCAGGCCTTCCGCGAGCACTGGGAGCGCTCGTGGGTGAGC

CAGCACTGCAAGAGCCTGGCCATCCCGTGCCCGGCGCACTACACGCCGCGCATGT

CGCCCGACTTCACGGTCTACATGATCAAATACCTCATGACGCTCATCGTGGGCATC

ACGTCGGGCTTCTGGATCTGGTCGGGCAAGACGCTGCACTCGTGGAGGAAGTTCTACAC

TCGCCTCACCAACAGCCGACACGGTGAGACCACCGTGTGA

Figure 2:
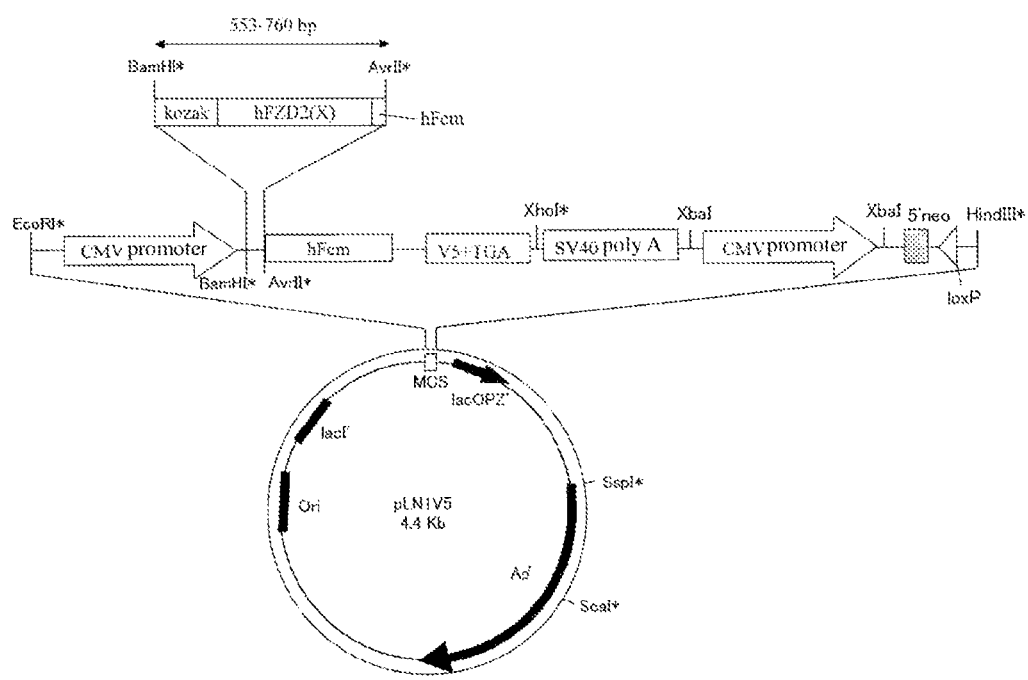
FIG. 2 shows the recombinant expression vector hFZD2 (X)-hFcm. X is any one of 153-175, 178, 184, 190, 197, 210, 216 and 222. * represents unique sites of restriction enzymes.

1-1-5. Construction of hFZD2(X)-hFcm (X=153-175, 178, 184, 190, 197, 210, 216, 222) Recombinant Expression Vectors Each of the PCR-amplified fragment recovered in Example 1-1-4 was digested with the BamHI and AvrII restriction enzymes (Roche Diagnostics, K. K., Japan), and the resultant was separated and recovered with 0.8% agarose gel. The enzyme-treated fragment was recovered from the gel using the QIAquick Gel Extraction Extraction Kit (Qiagen, Japan) in accordance with the instructions. A vector was prepared by digesting hFZD2(140)-hFcm recombinant expression vector from Example 1-1-3 with BamHI and AvrII. The enzyme treated fragments were introduced to BamHI•AvrII site of the above vector to construct recombinant expression vectors (FIG. 2).

A polynucleotide sequence (1, 230-1437 bp, SEQ ID NO:42-71) comprising a region from the initiation codon to the termination codon of hFZD2(X)-hFcm recombinant cDNA and the amino acid sequence (409-478 amino acids, SEQ ID NO:72-101) comprising a signal sequence of hFZD2(140)-hFcm encoded by the cDNA are shown below.

In these polynucleotide sequences, 69 bases from N-terminal represent signal sequence, capital letters represent the truncated form of hFZD2 extracellular region, and small letters represents human IgG1Fc variant portions. Also, in amino acid sequence, 233 amino acids from C-terminal represent human IgG1Fc variant portions, and sequence toward N-terminal therefrom represents the truncated form of hFZD2 extracellular region protein. Also, amino acid sequence does not comprise signal sequence.

```
SEQ ID NO: 42 [Polynucleotide sequence of hFZD2(153)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCgccgagcctaggtcttcagacaa
aactcacacatgcccaccgtgcccagcacctgaagccgaggggcccgtcagtctt
cctcttcccccaaaacccaaggacaccctcatgatctcccggacccctgaggtcac
atgcgtggtggtggacgtgagccacgaagaccctgaggtcaagttcaactggtacgt
ggacggcgtggaggtgcataatgccaagacaaagccgcgggaggagcagtacaacag
cacgtaccgtgtggtcagcgtcctcaccgtcctgcaccaggactggctgaatggcaa
ggagtacaagtgcgccgtctccaacaaagcccctcccagcctccatcgagaaaaccat
ctccaaagccaaagggcagccccgagaaccacaggtgtacaccctgcccccatcccg
ggatgagctgaccaagaaccaggtcagcctgacctgcctggtcaaaggcttctatcc
cagcgacatcgccgtggagtgggagagcaatgggcagccggagaacaactacaagac
cacgcctcccgtgctggactccgacggctccttcttcctctacagcaagctcaccgt
ggacaagagcaggtggcagcaggggaacgtcttctcatgctccgtgatgcatgaggc
tctgcacaaccactacacgcagaagagcctctccctgtctccgggtaaatga SEQ ID NO: 43 [Polynucleotide sequence of hFZD2(154)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGgccgagcctaggtcttcagac
aaaactcacacatgcccaccgtgcccagcacctgaagccgaggggcccgtcagtc
ttcctcttcccccaaaacccaaggacaccctcatgatctcccggacccctgaggtc
acatgcgtggtggtggacgtgagccacgaagaccctgaggtcaagttcaactggtac
gtggacggcgtggaggtgcataatgccaagacaaagccgcgggaggagcagtacaac
agcacgtaccgtgtggtcagcgtcctcaccgtcctgcaccaggactggctgaatggc
aaggagtacaagtgcgccgtctccaacaaagcccctcccagcctccatcgagaaaacc
atctccaaagccaaagggcagccccgagaaccacaggtgtacaccctgcccccatcc
cgggatgagctgaccaagaaccaggtcagcctgacctgcctggtcaaaggcttctat
cccagcgacatcgccgtggagtgggagagcaatgggcagccggagaacaactacaag
accacgcctcccgtgctggactccgacggctccttcttcctctacagcaagctcacc
gtggacaagagcaggtggcagcaggggaacgtcttctcatgctccgtgatgcatgag
gctctgcacaaccactacacgcagaagagcctctccctgtctccgggtaaatga SEQ ID NO: 44 [Polynucleotide sequence of hFZD2(155)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCgccgagcctaggtcttca
gacaaaactcacacatgcccaccgtgcccagcacctgaagccgaggggcccccgtca
gtcttcctcttcccccaaaacccaaggacaccctcatgatctcccggacccctgag
``` gtcacatgcgtggtggtggacgtgagccacgaagaccctgaggtcaagttcaactgg
tacgtggacggcgtggaggtgcataatgccaagacaaagccgcgggaggagcagtac
aacagcacgtaccgtgtggtcagcgtcctcaccgtcctgcaccaggactggctgaat
ggcaaggagtacaagtgcgccgtctccaacaaagccctcccagcctccatcgagaaa
accatctccaaagccaaagggcagccccgagaaccacaggtgtacaccctgccccca
tcccgggatgagctgaccaagaaccaggtcagcctgacctgcctggtcaaaggcttc
tatcccagcgacatcgccgtggagtgggagagcaatgggcagccggagaacaactac
aagaccacgcctcccgtgctggactccgacggctccttcttcctctacagcaagctc
accgtggacaagagcaggtggcagcaggggaacgtcttctcatgctccgtgatgcat
gaggctctgcacaaccactacacgcagaagagcctctccctgtctccgggtaaatga SEQ ID NO: 45 [Polynucleotide sequence of hFZD2(156)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCgccgagcctaggtct
tcagacaaaactcacacatgcccaccgtgcccagcacctgaagccgaggggcccccg
tcagtcttcctcttccccccaaaacccaaggacaccctcatgatctcccggacccct
gaggtcacatgcgtggtggtggacgtgagccacgaagaccctgaggtcaagttcaac
tggtacgtggacggcgtggaggtgcataatgccaagacaaagccgcgggaggagcag
tacaacagcacgtaccgtgtggtcagcgtcctcaccgtcctgcaccaggactggctg
aatggcaaggagtacaagtgcgccgtctccaacaaagccctcccagcctccatcgag
aaaaccatctccaaagccaaagggcagccccgagaaccacaggtgtacaccctgccc
ccatcccgggatgagctgaccaagaaccaggtcagcctgacctgcctggtcaaaggc
ttctatcccagcgacatcgccgtggagtgggagagcaatgggcagccggagaacaac
tacaagaccacgcctcccgtgctggactccgacggctccttcttcctctacagcaag
ctcaccgtggacaagagcaggtggcagcaggggaacgtcttctcatgctccgtgatg
catgaggctctgcacaaccactacacgcagaagagcctctccctgtctccgggtaaa
tga SEQ ID NO: 46 [Polynucleotide sequence of hFZD2(157)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGgccgagcctagg
tcttcagacaaaactcacacatgcccaccgtgcccagcacctgaagccgaggggcc
ccgtcagtcttcctcttccccccaaaacccaaggacaccctcatgatctcccggacc
cctgaggtcacatgcgtggtggtggacgtgagccacgaagaccctgaggtcaagttc
aactggtacgtggacggcgtggaggtgcataatgccaagacaaagccgcgggaggag
cagtacaacagcacgtaccgtgtggtcagcgtcctcaccgtcctgcaccaggactgg
ctgaatggcaaggagtacaagtgcgccgtctccaacaaagccctcccagcctccatc
gagaaaaccatctccaaagccaaagggcagccccgagaaccacaggtgtacaccctg
cccccatcccgggatgagctgaccaagaaccaggtcagcctgacctgcctggtcaaa
ggcttctatcccagcgacatcgccgtggagtgggagagcaatgggcagccggagaac
aactacaagaccacgcctcccgtgctggactccgacggctccttcttcctctacagc
aagctcaccgtggacaagagcaggtggcagcaggggaacgtcttctcatgctccgtg
atgcatgaggctctgcacaaccactacacgcagaagagcctctccctgtctccgggt
aaatga SEQ ID NO: 47 [Polynucleotide sequence of hFZD2(158)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTgccgagcct
aggtcttcagacaaaactcacacatgcccaccgtgcccagcacctgaagccgagggg
gccccgtcagtcttcctcttccccccaaaacccaaggacaccctcatgatctcccgg
acccctgaggtcacatgcgtggtggtggacgtgagccacgaagaccctgaggtcaag
ttcaactggtacgtggacggcgtggaggtgcataatgccaagacaaagccgcgggag
gagcagtacaacagcacgtaccgtgtggtcagcgtcctcaccgtcctgcaccaggac
tggctgaatggcaaggagtacaagtgcgccgtctccaacaaagccctcccagcctcc
atcgagaaaaccatctccaaagccaaagggcagccccgagaaccacaggtgtacacc
ctgcccccatcccgggatgagctgaccaagaaccaggtcagcctgacctgcctggtc
aaaggcttctatcccagcgacatcgccgtggagtgggagagcaatgggcagccggag -continued aacaactacaagaccacgcctcccgtgctggactccgacggctccttcttcctctac
agcaagctcaccgtggacaagagcaggtggcagcaggggaacgtcttctcatgctcc
gtgatgcatgaggctctgcacaaccactacacgcagaagagcctctccctgtctccg
ggtaaatga SEQ ID NO: 48 [Polynucleotide sequence of hFZD2(159)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCgccg
agcctaggtcttcagacaaaactcacacatgcccaccgtgcccagcacctgaagccg
aggggggccccgtcagtcttcctcttccccccaaaacccaaggacaccctcatgatct
cccggacccctgaggtcacatgcgtggtggtggacgtgagccacgaagaccctgagg
tcaagttcaactggtacgtggacggcgtggaggtgcataatgccaagacaaagccgc
gggaggagcagtacaacagcacgtaccgtgtggtcagcgtcctcaccgtcctgcacc
aggactggctgaatggcaaggagtacaagtgcgccgtctccaacaaagccctcccag
cctccatcgagaaaaccatctccaaagccaaagggcagccccgagaaccacaggtgt
acaccctgcccccatcccgggatgagctgaccaagaaccaggtcagcctgacctgcc
tggtcaaaggcttctatcccagcgacatcgccgtggagtgggagagcaatgggcagc
cggagaacaactacaagaccacgcctcccgtgctggactccgacggctccttcttcc
tctacagcaagctcaccgtggacaagagcaggtggcagcaggggaacgtcttctcat
gctccgtgatgcatgaggctctgcacaaccactacacgcagaagagcctctccctgt
ctccgggtaaatga SEQ ID NO: 49 [Polynucleotide sequence of hFZD2(160)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
gccgagcctaggtcttcagacaaaactcacacatgcccaccgtgcccagcacctgaa
gccgaggggccccgtcagtcttcctcttccccccaaaacccaaggacaccctcatg
atctcccggacccctgaggtcacatgcgtggtggtggacgtgagccacgaagaccctga
ggtcaagttcaactggtacgtggacggcgtggaggtgcataatgccaagacaaagccg
cgggaggagcagtacaacagcacgtaccgtgtggtcagcgtcctcaccgtcctgcacc
aggactggctgaatggcaaggagtacaagtgcgccgtctccaacaaagccctccca
gcctccatcgagaaaaccatctccaaagccaaagggcagccccgagaaccacaggtgt
acaccctgcccccatcccgggatgagctgaccaagaaccaggtcagcctgacctgcc
tggtcaaaggcttctatcccagcgacatcgccgtggagtgggagagcaatgggcagc
cggagaacaactacaagaccacgcctcccgtgctggactccgacggctccttcttcc
tctacagcaagctcaccgtggacaagagcaggtggcagcaggggaacgtcttctcat
gctccgtgatgcatgaggctctgcacaaccactacacgcagaagagcctctccctgt
ctccgggtaaatga SEQ ID NO: 50 [Polynucleotide sequence of hFZD2(161)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCgccgagcctaggtcttcagacaaaactcacacatgcccaccgtgcccagcacct
gaagccgaggggccccgtcagtcttcctcttccccccaaaacccaaggacaccctc
atgatctcccggacccctgaggtcacatgcgtggtggtggacgtgagccacgaagac
cctgaggtcaagttcaactggtacgtggacggcgtggaggtgcataatgccaagacaa
agccgcgggaggagcagtacaacagcacgtaccgtgtggtcagcgtcctcaccgtcct
gcaccaggactggctgaatggcaaggagtacaagtgcgccgtctccaacaaagccctc
ccagcctccatcgagaaaaccatctccaaagccaaagggcagccccgagaaccacagg
tgtacaccctgcccccatcccgggatgagctgaccaagaaccaggtcagcctgacctg
cctggtcaaaggcttctatcccagcgacatcgccgtggagtgggagagcaatgggcag
ccggagaacaactacaagaccacgcctcccgtgctggactccgacggctccttcttcc
tctacagcaagctcaccgtggacaagagcaggtggcagcaggggaacgtcttctcatg
ctccgtgatgcatgaggctctgcacaaccactacacgcagaagagcctctccctgtct
ccgggtaaatga SEQ ID NO: 51 [Polynucleotide sequence of hFZD2(162)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCgccgagcctaggtcttcagacaaaactcacacatgcccaccgtgcccagca
cctgaagccgagggggcccgtcagtcttcctcttccccccaaaacccaaggacacc
ctcatgatctcccggacccctgaggtcacatgcgtggtggtggacgtgagccacga
agaccctgaggtcaagttcaactggtacgtggacggcgtggaggtgcataatgccaa
gacaaagccgcgggaggagcagtacaacagcacgtaccgtgtggtcagcgtcctca
ccgtcctgcaccaggactggctgaatggcaaggagtacaagtgcgccgtctccaacaaa
gccctcccagcctccatcgagaaaaccatctccaaagccaaagggcagccccgagaa
ccacaggtgtacaccctgcccccatcccgggatgagctgaccaagaaccaggtcagc
ctgacctgcctggtcaaaggcttctatcccagcgacatcgccgtggagtgggagagca
atgggcagccggagaacaactacaagaccacgcctcccgtgctggactccgacggctc
cttcttcctctacagcaagctcaccgtggacaagagcaggtggcagcaggggaacgtc
ttctcatgctccgtgatgcatgaggctctgcacaaccactacacgcagaagagcctct
ccctgtctccgggtaaatga SEQ ID NO: 52 [Polynucleotide sequence of hFZD2(163)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCgccgagcctaggtcttcagacaaaactcacacatgcccaccgtgcccag
cacctgaagccgagggggcccgtcagtcttcctcttccccccaaaacccaaggacac
cctcatgatctcccggacccctgaggtcacatgcgtggtggtggacgtgagccacga
agaccctgaggtcaagttcaactggtacgtggacggcgtggaggtgcataatgccaa
gacaaagccgcgggaggagcagtacaacagcacgtaccgtgtggtcagcgtcctcacc
gtcctgcaccaggactggctgaatggcaaggagtacaagtgcgccgtctccaacaaag
ccctcccagcctccatcgagaaaaccatctccaaagccaaagggcagccccgagaacc
acaggtgtacaccctgcccccatcccgggatgagctgaccaagaaccaggtcagcctg
acctgcctggtcaaaggcttctatcccagcgacatcgccgtggagtgggagagcaatg
ggcagccggagaacaactacaagaccacgcctcccgtgctggactccgacggctcctt
cttcctctacagcaagctcaccgtggacaagagcaggtggcagcaggggaacgtcttc
tcatgctccgtgatgcatgaggctctgcacaaccactacacgcagaagagcctctccc
tgtctccgggtaaatga SEQ ID NO: 53 [Polynucleotide sequence of hFZD2(164)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCgccgagcctaggtcttcagacaaaactcacacatgcccaccgtgc
ccagcacctgaagccgagggggcccgtcagtcttcctcttccccccaaaacccaag
gacaccctcatgatctcccggacccctgaggtcacatgcgtggtggtggacgtgagc
cacgaagaccctgaggtcaagttcaactggtacgtggacggcgtggaggtgcataat
gccaagacaaagccgcgggaggagcagtacaacagcacgtaccgtgtggtcagcgtc
ctcaccgtcctgcaccaggactggctgaatggcaaggagtacaagtgcgccgtctcca
acaaagccctcccagcctccatcgagaaaaccatctccaaagccaaagggcagcccg
agaaccacaggtgtacaccctgcccccatcccgggatgagctgaccaagaaccaggtc
agcctgacctgcctggtcaaaggcttctatcccagcgacatcgccgtggagtgggaga
gcaatgggcagccggagaacaactacaagaccacgcctcccgtgctggactccgacgg
ctccttcttcctctacagcaagctcaccgtggacaagagcaggtggcagcaggggaac
gtcttctcatgctccgtgatgcatgaggctctgcacaaccactacacgcagaagagcc
tctccctgtctccgggtaaatga SEQ ID NO: 54 [Polynucleotide sequence of hFZD2(165)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT -continued
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTgccgagcctaggtcttcagacaaaactcacacatgcccaccgtgcccagcacctgaagccga
gggggcccgtcagtcttcctcttcccccaaaacccaaggacaccctcatgatctcccggacccctgaggtcacatgcgtggtggtg
gacgtgagccacgaagaccctgaggtcaagttcaactggtacgtggacggcgtggaggtgcataatgccaagacaaagccgcggg
aggagcagtacaacagcacgtaccgtgtggtcagcgtcctcaccgtcctgcaccaggactggctgaatggcaaggagtacaagtgc
gccgtctccaacaaagcccteccagcctccatcgagaaaaccatctccaaagccaaagggcagccccgagaaccacaggtgtacac
cctgcccccatcccgggatgagctgaccaagaaccaggtcagcctgacctgcctggtcaaaggcttctatcccagcgacatcgccgt
ggagtgggagagcaatgggcagccggagaacaactacaagaccacgcctcccgtgctggactccgacggctccttcttcctctaca
gcaagctcaccgtggacaagagcaggtggcagcaggggaacgtcttctcatgctccgtgatgcatgaggctctgcacaaccactaca
cgcagaagagcctctccctgtctccgggtaaatga SEQ ID NO: 55 [Polynucleotide sequence of hFZD2(166)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCgccgagcctaggtcttcagacaaaactcacacatgcccaccgtgcccagcacctgaag
ccgagggggcccgtcagtcttcctcttcccccaaaacccaaggacaccctcatgatctcccggacccctgaggtcacatgcgtggt
ggtggacgtgagccacgaagaccctgaggtcaagttcaactggtacgtggacggcgtggaggtgcataatgccaagacaaagccg
cgggaggagcagtacaacagcacgtaccgtgtggtcagcgtcctcaccgtcctgcaccaggactggctgaatggcaaggagtacaa
gtgcgccgtctccaacaaagcccteccagcctccatcgagaaaaccatctccaaagccaaagggcagccccgagaaccacaggtgt
acaccctgcccccatcccgggatgagctgaccaagaaccaggtcagcctgacctgcctggtcaaaggcttctatcccagcgacatcg
ccgtggagtgggagagcaatgggcagccggagaacaactacaagaccacgcctcccgtgctggactccgacggctccttcttcctct
acagcaagctcaccgtggacaagagcaggtggcagcaggggaacgtcttctcatgctccgtgatgcatgaggctctgcacaaccact
acacgcagaagagcctctccctgtctccgggtaaatga SEQ ID NO: 56 [Polynucleotide sequence of hFZD2(167)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGgccgagcctaggtcttcagacaaaactcacacatgcccaccgtgcccagcacc
tgaagccgagggggcccgtcagtcttcctcttcccccaaaacccaaggacaccctcatgatctcccggacccctgaggtcacatg
cgtggtggtggacgtgagccacgaagaccctgaggtcaagttcaactggtacgtggacggcgtggaggtgcataatgccaagacaa
agccgcgggaggagcagtacaacagcacgtaccgtgtggtcagcgtcctcaccgtcctgcaccaggactggctgaatggcaagga
gtacaagtgcgccgtctccaacaaagcccteccagcctccatcgagaaaaccatctccaaagccaaagggcagccccgagaaccac
aggtgtacaccctgcccccatcccgggatgagctgaccaagaaccaggtcagcctgacctgcctggtcaaaggcttctatcccagcg
acatcgccgtggagtgggagagcaatgggcagccggagaacaactacaagaccacgcctcccgtgctggactccgacggctcctt
cttcctctacagcaagctcaccgtggacaagagcaggtggcagcaggggaacgtcttctcatgctccgtgatgcatgaggctctgcac
aaccactacacgcagaagagcctctccctgtctccgggtaaatga SEQ ID NO: 57 [Polynucleotide sequence of hFZD2(168)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCgccgagcctaggtcttcagacaaaactcacacatgcccaccgtgccca
gcacctgaagccgagggggcccgtcagtcttcctcttcccccaaaacccaaggacaccctcatgatctcccggacccctgaggtc
acatgcgtggtggtggacgtgagccacgaagaccctgaggtcaagttcaactggtacgtggacggcgtggaggtgcataatgccaa
gacaaagccgcgggaggagcagtacaacagcacgtaccgtgtggtcagcgtcctcaccgtcctgcaccaggactggctgaatggc
aaggagtacaagtgcgccgtctccaacaaagcccteccagcctccatcgagaaaaccatctccaaagccaaagggcagccccgag
aaccacaggtgtacaccctgcccccatcccgggatgagctgaccaagaaccaggtcagcctgacctgcctggtcaaaggcttctatc
ccagcgacatcgccgtggagtgggagagcaatgggcagccggagaacaactacaagaccacgcctcccgtgctggactccgacg
gctccttcttcctctacagcaagctcaccgtggacaagagcaggtggcagcaggggaacgtcttctcatgctccgtgatgcatgaggct
ctgcacaaccactacacgcagaagagcctctccctgtctccgggtaaatga SEQ ID NO: 58 [Polynucleotide sequence of hFZD2(169)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGAC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCGGGTGGCCCG
GGCGGCGGCGGCGCTCCCCGCGCTACgccgagcctaggtcttcagacaaaactcacacatgcccaccgtg
cccagcacctgaagccgagggggcccgtcagtcttcctcttcccccaaaacccaaggacaccctcatgatctcccggacccctga
ggtcacatgcgtggtggtggacgtgagccacgaagaccctgaggtcaagttcaactggtacgtggacggcgtggaggtgcataatg
ccaagacaaagccgcgggaggagcagtacaacagcacgtaccgtgtggtcagcgtcctcaccgtcctgcaccaggactggctgaat
ggcaaggagtacaagtgcgccgtctccaacaaagcctcccagcctccatcgagaaaaccatctccaaagccaaagggcagcccc
gagaaccacaggtgtacaccctgcccccatcccgggatgagctgaccaagaaccaggtcagcctgacctgcctggtcaaaggcttct
atcccagcgacatcgccgtggagtgggagagcaatgggcagccggagaacaactacaagaccacgcctcccgtgctggactccga
cggctccttcttcctctacagcaagctcaccgtggacaagagcaggtggcagcaggggaacgtcttctcatgctccgtgatgcatgag
gctctgcacaaccactacacgcagaagagcctctccctgtctccgggtaaatga SEQ ID NO: 59 [Polynucleotide sequence of hFZD2(170)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCGGGTGGCCCG
GGCGGCGGCGGCGCTCCCCGCGCTACGCCgccgagcctaggtcttcagacaaaactcacacatgccca
ccgtgcccagcacctgaagccgagggggcccgtcagtcttcctcttcccccaaaacccaaggacaccctcatgatctcccggacc
cctgaggtcacatgcgtggtggtggacgtgagccacgaagaccctgaggtcaagttcaactggtacgtggacggcgtggaggtgca
taatgccaagacaaagccgcgggaggagcagtacaacagcacgtaccgtgtggtcagcgtcctcaccgtcctgcaccaggactggc
tgaatggcaaggagtacaagtgcgccgtctccaacaaagcctcccagcctccatcgagaaaaccatctccaaagccaaagggcag
ccccgagaaccacaggtgtacaccctgcccccatcccgggatgagctgaccaagaaccaggtcagcctgacctgcctggtcaaagg
cttctatcccagcgacatcgccgtggagtgggagagcaatgggcagccggagaacaactacaagaccacgcctcccgtgctggact
ccgacggctccttcttcctctacagcaagctcaccgtggacaagagcaggtggcagcaggggaacgtcttctcatgctccgtgatgca
tgaggctctgcacaaccactacacgcagaagagcctctccctgtctccgggtaaatga SEQ ID NO: 60 [Polynucleotide sequence of hFZD2(171)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCGGGTGGCCCG
GGCGGCGGCGGCGCTCCCCGCGCTACGCCACGgccgagcctaggtcttcagacaaaactcacacatg
cccaccgtgcccagcacctgaagccgagggggcccgtcagtcttcctcttcccccaaaacccaaggacaccctcatgatctcccg
gacccctgaggtcacatgcgtggtggtggacgtgagccacgaagaccctgaggtcaagttcaactggtacgtggacggcgtggagg
tgcataatgccaagacaaagccgcgggaggagcagtacaacagcacgtaccgtgtggtcagcgtcctcaccgtcctgcaccaggac
tggctgaatggcaaggagtacaagtgcgccgtctccaacaaagcctcccagcctccatcgagaaaaccatctccaaagccaaagg
gcagccccgagaaccacaggtgtacaccctgcccccatcccgggatgagctgaccaagaaccaggtcagcctgacctgcctggtca
aaggcttctatcccagcgacatcgccgtggagtgggagagcaatgggcagccggagaacaactacaagaccacgcctcccgtgct
ggactccgacggctccttcttcctctacagcaagctcaccgtggacaagagcaggtggcagcaggggaacgtcttctcatgctccgtg
atgcatgaggctctgcacaaccactacacgcagaagagcctctccctgtctccgggtaaatga SEQ ID NO: 61 [Polynucleotide sequence of hFZD2(172)-hFcm]:
ATGCGGCCCCGCAGCGCCCTGCCCCGCCTGCTGCTGCCGCTGCTGCTGCTGCCCG
CCGCCGGGCCGGCCCAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCGGGTGGCCCG
GGCGGCGGCGGCGCTCCCCGCGCTACGCCACGCTGgccgagcctaggtcttcagacaaaactcac
acatgcccaccgtgcccagcacctgaagccgagggggcccgtcagtcttcctcttcccccaaaacccaaggacaccctcatgatc
tcccggacccctgaggtcacatgcgtggtggtggacgtgagccacgaagaccctgaggtcaagttcaactggtacgtggacggcgt
ggaggtgcataatgccaagacaaagccgcgggaggagcagtacaacagcacgtaccgtgtggtcagcgtcctcaccgtcctgcac
caggactggctgaatggcaaggagtacaagtgcgccgtctccaacaaagcctcccagcctccatcgagaaaaccatctccaaagc
caaagggcagccccgagaaccacaggtgtacaccctgcccccatcccgggatgagctgaccaagaaccaggtcagcctgacctgc
ctggtcaaaggcttctatcccagcgacatcgccgtggagtgggagagcaatgggcagccggagaacaactacaagaccacgcctcc -continued cgtgctggactccgacggctccttcttcctctacagcaagctcaccgtggacaagagcaggtggcagcaggggaacgtcttctcatgc
tccgtgatgcatgaggctctgcacaaccactacacgcagaagagcctctccctgtctccgggtaaatga SEQ ID NO: 62 [Polynucleotide sequence of hFZD2(173)-hFcm]:
<u>ATGCGGCCCCGCCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGgccgagcctaggtcttcagacaaaa
ctcacacatgcccaccgtgcccagcacctgaagccgaggggccccgtcagtcttcctcttccccccaaaacccaaggacaccctca
tgatctcccggacccctgaggtcacatgcgtggtggtggacgtgagccacgaagaccctgaggtcaagttcaactggtacgtggacg
gcgtggaggtgcataatgccaagacaaagccgcgggaggagcagtacaacagcacgtaccgtgtggtcagcgtcctcaccgtcctg
caccaggactggctgaatggcaaggagtacaagtgcgccgtctccaacaaagcccctcccagcctccatcgagaaaaccatctccaa
agccaaaggggcagccccgagaaccacaggtgtacaccctgccccatcccgggatgagctgaccaagaaccaggtcagcctgac
ctgcctggtcaaaggcttctatcccagcgacatcgccgtggagtgggagagcaatgggcagccggagaacaactacaagaccacg
cctcccgtgctggactccgacggctccttcttcctctacagcaagctcaccgtggacaagagcaggtggcagcaggggaacgtcttct
catgctccgtgatgcatgaggctctgcacaaccactacacgcagaagagcctctccctgtctccgggtaaatga SEQ ID NO: 63 [Polynucleotide sequence of hFZD2(174)-hFcm]:
<u>ATGCGGCCCCGCCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACgccgagcctaggtcttcaga
caaaactcacacatgcccaccgtgcccagcacctgaagccgaggggccccgtcagtcttcctcttccccccaaaacccaaggaca
ccctcatgatctcccggacccctgaggtcacatgcgtggtggtggacgtgagccacgaagaccctgaggtcaagttcaactggtacgt
ggacggcgtggaggtgcataatgccaagacaaagccgcgggaggagcagtacaacagcacgtaccgtgtggtcagcgtcctcacc
gtcctgcaccaggactggctgaatggcaaggagtacaagtgcgccgtctccaacaaagcccctcccagcctccatcgagaaaaccatc
tccaaagccaaagggcagccccgagaaccacaggtgtacaccctgccccatcccgggatgagctgaccaagaaccaggtcagcc
tgacctgcctggtcaaaggcttctatcccagcgacatcgccgtggagtgggagagcaatgggcagccggagaacaactacaagacc
acgcctcccgtgctggactccgacggctccttcttcctctacagcaagctcaccgtggacaagagcaggtggcagcaggggaacgtc
ttctcatgctccgtgatgcatgaggctctgcacaaccactacacgcagaagagcctctccctgtctccgggtaaatga SEQ ID NO: 64 [Polynucleotide sequence of hFZD2(175)-hFcm]:
<u>ATGCGGCCCCGCCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCgccgagcctaggtctt
cagacaaaactcacacatgcccaccgtgcccagcacctgaagccgaggggccccgtcagtcttcctcttccccccaaaacccaag
gacaccctcatgatctcccggacccctgaggtcacatgcgtggtggtggacgtgagccacgaagaccctgaggtcaagttcaactgg
tacgtggacggcgtggaggtgcataatgccaagacaaagccgcgggaggagcagtacaacagcacgtaccgtgtggtcagcgtcc
tcaccgtcctgcaccaggactggctgaatggcaaggagtacaagtgcgccgtctccaacaaagcccctcccagcctccatcgagaaa
accatctccaaagccaaagggcagccccgagaaccacaggtgtacaccctgccccatcccgggatgagctgaccaagaaccaggt
cagcctgacctgcctggtcaaaggcttctatcccagcgacatcgccgtggagtgggagagcaatgggcagccggagaacaactaca
agaccacgcctcccgtgctggactccgacggctccttcttcctctacagcaagctcaccgtggacaagagcaggtggcagcagggg
aacgtcttctcatgctccgtgatgcatgaggctctgcacaaccactacacgcagaagagcctctccctgtctccgggtaaatga SEQ ID NO: 65 [Polynucleotide sequence of hFZD2(178)-hFcm]:
<u>ATGCGGCCCCGCCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCg
ccgagcctaggtcttcagacaaaactcacacatgcccaccgtgcccagcacctgaagccgaggggccccgtcagtcttcctcttcc
ccccaaaacccaaggacaccctcatgatctcccggacccctgaggtcacatgcgtggtggtggacgtgagccacgaagaccctgag
gtcaagttcaactggtacgtggacggcgtggaggtgcataatgccaagacaaagccgcgggaggagcagtacaacagcacgtacc -continued gtgtggtcagcgtcctcaccgtcctgcaccaggactggctgaatggcaaggagtacaagtgcgccgtctccaacaaagccctcccag
cctccatcgagaaaaccatctccaaagccaaagggcagccccgagaaccacaggtgtacaccctgccccatcccgggatgagctg
accaagaaccaggtcagcctgacctgcctggtcaaaggcttctatcccagcgacatcgccgtggagtgggagagcaatgggcagcc
ggagaacaactacaagaccacgcctcccgtgctggactccgacggctccttcttcctctacagcaagctcaccgtggacaagagcag
gtggcagcaggggaacgtcttctcatgctccgtgatgcatgaggctctgcacaaccactacacgcagaagagcctctccctgtctccg
ggtaaatga SEQ ID NO: 66 [Polynucleotide sequence of hFZD2(184)-hFcm]:
<u>ATGCGGCCCCGCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCC
CGCGCGTCCTCAAGGTGgccgagcctaggtcttcagacaaaactcacacatgcccaccgtgcccagcacctgaagcc
gagggggcccgtcagtcttcctcttccccccaaaacccaaggacaccctcatgatctcccggacccctgaggtcacatgcgtggtg
gtggacgtgagccacgaagaccctgaggtcaagttcaactggtacgtggacggcgtggatgcataatgccaagacaaagccgc
gggaggagcagtacaacagcacgtaccgtgtggtcagcgtcctcaccgtcctgcaccaggactggctgaatggcaaggagtacaag
tgcgccgtctccaacaaagccctcccagcctccatcgagaaaaccatctccaaagccaaagggcagccccgagaaccacaggtgta
caccctgccccatcccgggatgagctgaccaagaaccaggtcagcctgacctgcctggtcaaaggcttctatcccagcgacatcgc
cgtggagtgggagagcaatgggcagccggagaacaactacaagaccacgcctcccgtgctggactccgacggctccttcttcctcta
cagcaagctcaccgtggacaagagcaggtggcagcaggggaacgtcttctcatgctccgtgatgcatgaggctctgcacaaccacta
cacgcagaagagcctctccctgtctccgggtaaatga SEQ ID NO: 67 [Polynucleotide sequence of hFZD2(190)-hFcm]:
<u>ATGCGGCCCCGCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCC
CGCGCGTCCTCAAGGTGCCATCCTATCTCAGCTACgccgagcctaggtcttcagacaaaactcacaca
tgcccaccgtgcccagcacctgaagcgagggggcccgtcagtcttcctcttccccccaaaacccaaggacaccctcatgatctcc
cggacccctgaggtcacatgcgtggtggtggacgtgagccacgaagaccctgaggtcaagttcaactggtacgtggacggcgtgga
ggtgcataatgccaagacaaagccgcgggaggagcagtacaacagcacgtaccgtgtggtcagcgtcctcaccgtcctgcaccag
gactggctgaatggcaaggagtacaagtgcgccgtctccaacaaagccctcccagcctccatcgagaaaaccatctccaaagccaa
agggcagccccgagaaccacaggtcagcctgacctgcctggtcaaaggcttctatcccagcgacatcgccgtggagtgggagagcaatgggcagccggagaacaactacaagaccacgcctcccgt
gctggactccgacggctccttcttcctctacagcaagctcaccgtggacaagagcaggtggcagcaggggaacgtcttctcatgctcc
gtgatgcatgaggctctgcacaaccactacacgcagaagagcctctccctgtctccgggtaaatga SEQ ID NO: 68 [Polynucleotide sequence of hFZD2(197)-hFcm]:
<u>ATGCGGCCCCGCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCC
CGCGCGTCCTCAAGGTGCCATCCTATCTCAGCTACAAGTTTCTGGGCGAGCGTGAT
gccgagcctaggtcttcagacaaaactcacacatgcccaccgtgcccagcacctgaagccgagggggcccgtcagtcttcctcttc
ccccccaaaacccaaggacaccctcatgatctcccggacccctgaggtcacatgcgtggtggtggacgtgagccacgaagaccctga
ggtcaagttcaactggtacgtggacggcgtggaggtgcataatgccaagacaaagccgcgggaggagcagtacaacagcacgtac
cgtgtggtcagcgtcctcaccgtcctgcaccaggactggctgaatggcaaggagtacaagtgcgccgtctccaacaaagccctccca
gcctccatcgagaaaaccatctccaaagccaaagggcagccccgagaaccacaggtgtacaccctgccccatcccgggatgagct
gaccaagaaccaggtcagcctgacctgcctggtcaaaggcttctatcccagcgacatcgccgtggagtgggagagcaatgggcagc
cggagaacaactacaagaccacgcctcccgtgctggactccgacggctccttcttcctctacagcaagctcaccgtggacaagagca
ggtggcagcaggggaacgtcttctcatgctccgtgatgcatgaggctctgcacaaccactacacgcagaagagcctctccctgtctcc
gggtaaatga SEQ ID NO: 69 [Polynucleotide sequence of hFZD2(210)-hFcm]:
<u>ATGCGGCCCCGCAGCGCCCTGCCCCGCCTGCTGCTGCCGCTGCTGCTGCTGCCCG</u>
<u>CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC -continued
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCC
CGCGCGTCCTCAAGGTGCCATCCTATCTCAGCTACAAGTTTCTGGGCGAGCGTGAT
TGTGCTGCGCCCTGCGAACCTGCGCGGCCCGATGGTTCCgccgagcctaggtcttcagacaaaac
tcacacatgcccaccgtgcccagcacctgaagccgagggggcccgtcagtcttcctcttccccccaaaacccaaggacaccctcat
gatctcccggacccctgaggtcacatgcgtggtggtggacgtgagccacgaagaccctgaggtcaagttcaactggtacgtggacg
gcgtggaggtgcataatgccaagacaaagccgcgggaggagcagtacaacagcacgtaccgtgtggtcagcgtcctcaccgtcctg
caccaggactggctgaatggcaaggagtacaagtgcgccgtctccaacaaagcccatcccagcctccatcgagaaaaccatctccaa
agccaaagggcagccccgagaaccacaggtgtacaccctgcccccatcccgggatgagctgaccaagaaccaggtcagcctgac
ctgcctggtcaaaggcttctatcccagcgacatcgccgtggagtgggagagcaatgggcagccggagaacaactacaagaccacg
cctcccgtgctggactccgacggctccttcttcctctacagcaagctcaccgtggacaagagcaggtggcagcaggggaacgtcttct
catgctccgtgatgcatgaggctctgcacaaccactacacgcagaagagcctctccctgtctccgggtaaatga SEQ ID NO: 70 [Polynucleotide sequence of hFZD2(216)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCC
CGCGCGTCCTCAAGGTGCCATCCTATCTCAGCTACAAGTTTCTGGGCGAGCGTGAT
TGTGCTGCGCCCTGCGAACCTGCGCGGCCCGATGGTTCCATGTTCTTCTCACAGG
AGgccgagcctaggtcttcagacaaaactcacacatgcccaccgtgcccagcacctgaagccgagggggcccgtcagtcttcct
cttccccccaaaacccaaggacaccctcatgatctcccggacccctgaggtcacatgcgtggtggtggacgtgagccacgaagacc
ctgaggtcaagttcaactggtacgtggacggcgtggaggtgcataatgccaagacaaagccgcgggaggagcagtacaacagcac
gtaccgtgtggtcagcgtcctcaccgtcctgcaccaggactggctgaatggcaaggagtacaagtgcgccgtctccaacaaagccct
cccagcctccatcgagaaaaccatctccaaagccaaagggcagccccgagaaccacaggtgtacaccctgcccccatcccgggat
gagctgaccaagaaccaggtcagcctgacctgcctggtcaaaggcttctatcccagcgacatcgccgtggagtgggagagcaatgg
gcagccggagaacaactacaagaccacgcctcccgtgctggactccgacggctccttcttcctctacagcaagctcaccgtggacaa
gagcaggtggcagcaggggaacgtcttctcatgctccgtgatgcatgaggctctgcacaaccactacacgcagaagagcctctccct
gtctccgggtaaatga SEQ ID NO: 71 [Polynucleotide sequence of hFZD2(222)-hFcm]:
<u>ATGCGGCCCCGCAGCGCCCTGCCCCGCCTGCTGCTGCCGCTGCTGCTGCTGCCCG
CCGCCGGGCCGGCC</u>CAGTTCCACGGGGAGAAGGGCATCTCCATCCCGGACCACG
GCTTCTGCCAGCCCATCTCCATCCCGCTGTGCACGGACATCGCCTACAACCAGACC
ATCATGCCCAACCTTCTGGGCCACACGAACCAGGAGGACGCAGGCCTAGAGGTG
CACCAGTTCTATCCGCTGGTGAAGGTGCAGTGCTCGCCCGAACTGCGCTTCTTCCT
GTGCTCCATGTACGCACCCGTGTGCACCGTGCTGGAACAGGCCATCCCGCCGTGC
CGCTCTATCTGTGAGCGCGCGCGCCAGGGCTGCGAAGCCCTCATGAACAAGTTCG
GTTTTCAGTGGCCCGAGCGCCTGCGCTGCGAGCACTTCCCGCGCCACGGCGCCGA
GCAGATCTGCGTCGGCCAGAACCACTCCGAGGACGGAGCTCCCGCGCTACTCACC
ACCGCGCCGCCGCCGGGACTGCAGCCGGGTGCCGGGGGCACCCCGGGTGGCCCG
GGCGGCGGCGGCGCTCCCCCGCGCTACGCCACGCTGGAGCACCCCTTCCACTGCC
CGCGCGTCCTCAAGGTGCCATCCTATCTCAGCTACAAGTTTCTGGGCGAGCGTGAT
TGTGCTGCGCCCTGCGAACCTGCGCGGCCCGATGGTTCCATGTTCTTCTCACAGG
AGGAGACGCGTTTCGCGCGCgccgagcctaggtcttcagacaaaactcacacatgcccaccgtgcccagcacctg
aagccgagggggcccgtcagtcttcctcttccccccaaaacccaaggacaccctcatgatctcccggacccctgaggtcacatgcg
tggtggtggacgtgagccacgaagaccctgaggtcaagttcaactggtacgtggacggcgtggaggtgcataatgccaagacaaag
ccgcgggaggagcagtacaacagcacgtaccgtgtggtcagcgtcctcaccgtcctgcaccaggactggctgaatggcaaggagta
caagtgcgccgtctccaacaaagcccatcccagcctccatcgagaaaaccatctccaaagccaaagggcagccccgagaaccacag
gtgtacaccctgcccccatcccgggatgagctgaccaagaaccaggtcagcctgacctgcctggtcaaaggcttctatcccagcgac
atcgccgtggagtgggagagcaatgggcagccggagaacaactacaagaccacgcctcccgtgctggactccgacggctccttctt
cctctacagcaagctcaccgtggacaagagcaggtggcagcaggggaacgtcttctcatgctccgtgatgcatgaggctctgcacaa
ccactacacgcagaagagcctctccctgtctccgggtaaatga SEQ ID NO: 72 [Amino acid sequence of hFZD2(153)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAAEPRSSDKTHTCPPCPAPEAEG
APSVFLFPPKPKDTLMISRTPEVTCVVVDVSHEDPEVKFNWYVDGVEVHNAKTKPRE
EQYNSTYRVVSVLTVLHQDWLNGKEYKCAVSNKALPASIEKTISKAKGQPREPQVYT
LPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK SEQ ID NO: 73 [Amino acid sequence of hFZD2(154)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGAEPRSSDKTHTCPPCPAPEAE
GAPSVFLFPPKPKDTLMISRTPEVTCVVVDVSHEDPEVKFNWYVDGVEVHNAKTKP
REEQYNSTYRVVSVLTVLHQDWLNGKEYKCAVSNKALPASIEKTISKAKGQPREPQV
YTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK SEQ ID NO: 74 [Amino acid sequence of hFZD2(155)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGAEPRSSDKTHTCPPCPAPEA
EGAPSVFLFPPKPKDTLMISRTPEVTCVVVDVSHEDPEVKFNWYVDGVEVHNAKTK
PREEQYNSTYRVVSVLTVLHQDWLNGKEYKCAVSNKALPASIEKTISKAKGQPREPQ
VYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGK SEQ ID NO: 75 [Amino acid sequence of hFZD2(156)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTAEPRSSDKTHTCPPCPAPE
AEGAPSVFLFPPKPKDTLMISRTPEVTCVVVDVSHEDPEVKFNWYVDGVEVHNAKT
KPREEQYNSTYRVVSVLTVLHQDWLNGKEYKCAVSNKALPASIEKTISKAKGQPREP
QVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK SEQ ID NO: 76 [Amino acid sequence of hFZD2(157)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPAEPRSSDKTHTCPPCPAPE
AEGAPSVFLFPPKPKDTLMISRTPEVTCVVVDVSHEDPEVKFNWYVDGVEVHNAKT
KPREEQYNSTYRVVSVLTVLHQDWLNGKEYKCAVSNKALPASIEKTISKAKGQPREP
QVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK SEQ ID NO: 77 [Amino acid sequence of hFZD2(158)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGAEPRSSDKTHTCPPCPA
PEAEGAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPASIEKTISKAKGQPR
EPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID NO: 78 [Amino acid sequence of hFZD2(159)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGAEPRSSDKTHTCPPCP
APEAEGAPSVFLFPPKPKDTLMISRTPEVTCVVVDVSHEDPEVKFNWYVDGVEVHN
AKTKPREEQYNSTYRVVSVLTVLHQDWLNGKEYKCAVSNKALPASIEKTISKAKGQ
REPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 79 [Amino acid sequence of hFZD2(160)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPAEPRSSDKTHTCPPC
PAPEAEGAPSVFLFPPKPKDTLMISRTPEVTCVVVDVSHEDPEVKFNWYVDGVEVHN
AKTKPREEQYNSTYRVVSVLTVLHQDWLNGKEYKCAVSNKALPASIEKTISKAKGQP
REPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 80 [Amino acid sequence of hFZD2(161)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPAEPRSSDKTHTCPP
CPAPEAEGAPSVFLFPPKPKDTLMISRTPEVTCVVVDVSHEDPEVKFNWYVDGVEVH
NAKTKPREEQYNSTYRVVSVLTVLHQDWLNGKEYKCAVSNKALPASIEKTISKAKGQ
PREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 81 [Amino acid sequence of hFZD2(162)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGAEPRSSDKTHTCP
PCPAPEAEGAPSVFLFPPKPKDTLMISRTPEVTCVVVDVSHEDPEVKFNWYVDGVEV
HNAKTKPREEQYNSTYRVVSVLTVLHQDWLNGKEYKCAVSNKALPASIEKTISKAKG
QPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK SEQ ID NO: 82 [Amino acid sequence of hFZD2(163)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGAEPRSSDKTHT
CPPCPAPEAEGAPSVFLFPPKPKDTLMISRTPEVTCVVVDVSHEDPEVKFNWYVDGV
EVHNAKTKPREEQYNSTYRVVSVLTVLHQDWLNGKEYKCAVSNKALPASIEKTISKA
KGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK -continued SEQ ID NO: 83 [Amino acid sequence of hFZD2(164)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAEPRSSDKTH
TCPPCPAPEAEGAPSVFLFPPKPKDTLMISRTPEVTCVVVDVSHEDPEVKFNWYVDG
VEVHNAKTKPREEQYNSTYRVVSVLTVLHQDWLNGKEYKCAVSNKALPASIEKTISK
AKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK SEQ ID NO: 84 [Amino acid sequence of hFZD2(165)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAAEPRSSDKT
HTCPPCPAPEAEGAPSVFLFPPKPKDTLMISRTPEVTCVVVDVSHEDPEVKFNWYVD
GVEVHNAKTKPREEQYNSTYRVVSVLTVLHQDWLNGKEYKCAVSNKALPASIEKTIS
KAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID NO: 85 [Amino acid sequence of hFZD2(166)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPAEPRSSDKT
HTCPPCPAPEAEGAPSVFLFPPKPKDTLMISRTPEVTCVVVDVSHEDPEVKFNWYVD
GVEVHNAKTKPREEQYNSTYRVVSVLTVLHQDWLNGKEYKCAVSNKALPASIEKTIS
KAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID NO: 86 [Amino acid sequence of hFZD2(167)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPAEPRSSDK
THTCPPCPAPEAEGAPSVFLFPPKPKDTLMISRTPEVTCVVVDVSHEDPEVKFNWYVD
GVEVHNAKTKPREEQYNSTYRVVSVLTVLHQDWLNGKEYKCAVSNKALPASIEKTIS
KAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID NO: 87 [Amino acid sequence of hFZD2(168)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRAEPRSSD
KTHTCPPCPAPEAEGAPSVFLFPPKPKDTLMISRTPEVTCVVVDVSHEDPEVKFNWYV
DGVEVHNAKTKPREEQYNSTYRVVSVLTVLHQDWLNGKEYKCAVSNKALPASIEKTI
SKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK SEQ ID NO: 88 [Amino acid sequence of hFZD2(169)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGAPPRYAEPRSS
DKTHTCPPCPAPEAEGAPSVFLFPPKPKDTLMISRTPEVTCVVVDVSHEDPEVKFNWY
VDGVEVHNAKTKPREEQYNSTYRVVSVLTVLHQDWLNGKEYKCAVSNKALPASIEK
TISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK SEQ ID NO: 89 [Amino acid sequence of hFZD2(170)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYAAEPRS
SDKTHTCPPCPAPEAEGAPSVFLFPPKPKDTLMISRTPEVTCVVVDVSHEDPEVKFNW
YVDGVEVHNAKTKPREEQYNSTYRVVSVLTVLHQDWLNGKEYKCAVSNKALPASIE
KTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK SEQ ID NO: 90 [Amino acid sequence of hFZD2(171)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATAEPR
SSDKTHTCPPCPAPEAEGAPSVFLFPPKPKDTLMISRTPEVTCVVVDVSHEDPEVKFN
WYVDGVEVHNAKTKPREEQYNSTYRVVSVLTVLHQDWLNGKEYKCAVSNKALPAS
IEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK SEQ ID NO: 91 [Amino acid sequence of hFZD2(172)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLAEP
RSSDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCAVSNKALPA
SIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK SEQ ID NO: 92 [Amino acid sequence of hFZD2(173)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEAE
PRSSDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCAVSNKALPA
SIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK SEQ ID NO: 93 [Amino acid sequence of hFZD2(174)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHA
EPRSSDKTHTCPPCPAPEAEGAPSVFLFPPKPKDTLMISRTPEVTCVVVDVSHEDPEVK
FNWYVDGVEVHNAKTKPREEQYNSTYRVVSVLTVLHQDWLNGKEYKCAVSNKALP
ASIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSP
GK SEQ ID NO: 94 [Amino acid sequence of hFZD2(175)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
AEPRSSDKTHTCPPCPAPEAEGAPSVFLFPPKPKDTLMISRTPEVTCVVVDVSHEDPEV
KFNWYVDGVEVHNAKTKPREEQYNSTYRVVSVLTVLHQDWLNGKEYKCAVSNKA
LPASIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSL
SPGK SEQ ID NO: 95 [Amino acid sequence of hFZD2(178)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCAEPRSSDKTHTCPPCPAPEAEGAPSVFLFPPKPKDTLMISRTPEVTCVVVDVSHED
PEVKFNWYVDGVEVHNAKTKPREEQYNSTYRVVSVLTVLHQDWLNGKEYKCAVSN
KALPASIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKS
LSLSPGK SEQ ID NO: 96 [Amino acid sequence of hFZD2(184)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVAEPRSSDKTHTCPPCPAPEAEGAPSVFLFPPKPKDTLMISRTPEVTCVVV
DVSHEDPEVKFNWYVDGVEVHNAKTKPREEQYNSTYRVVSVLTVLHQDWLNGKEY
KCAVSNKALPASIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHN
HYTQKSLSLSPGK SEQ ID NO: 97 [Amino acid sequence of hFZD2(190)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVPSYLSYAEPRSSDKTHTCPPCPAPEAEGAPSVFLFPPKPKDTLMISRTPE
VTCVVVDVSHEDPEVKFNWYVDGVEVHNAKTKPREEQYNSTYRVVSVLTVLHQDW
LNGKEYKCAVSNKALPASIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVM
HEALHNHYTQKSLSLSPGK SEQ ID NO: 98 [Amino acid sequence of hFZD2(197)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVPSYLSYKFLGERDAEPRSSDKTHTCPPCPAPEAEGAPSVFLFPPKPKDTL
MISRTPEVTCVVVDVSHEDPEVKFNWYVDGVEVHNAKTKPREEQYNSTYRVVSVLT
VLHQDWLNGKEYKCAVSNKALPASIEKTISKAKGQPREPQVYTLPPSRDELTKNQVS
LTCLVKGFYPSDIAVEWESNGQPENNYKTTPPVLDSDGSFFLYSKLTVDKSRWQQGN
VFSCSVMHEALHNHYTQKSLSLSPGK SEQ ID NO: 99 [Amino acid sequence of hFZD2(210)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVPSYLSYKFLGERDCAAPCEPARPDGSAEPRSSDKTHTCPPCPAPEAEGA
PSVFLFPPKPKDTLMISRTPEVTCVVVDVSHEDPEVKFNWYVDGVEVHNAKTKPREE
QYNSTYRVVSVLTVLHQDWLNGKEYKCAVSNKALPASIEKTISKAKGQPREPQVYTL
PPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK -continued
SEQ ID NO: 100 [Amino acid sequence of hFZD2(216)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVPSYLSYKFLGERDCAAPCEPARPDGSMFFSQEAEPRSSDKTHTCPPCPA
PEAEGAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPASIEKTISKAKGQPR
EPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID NO: 101 [Amino acid sequence of hFZD2(222)-hFcm]:
QFHGEKGISIPDHGFCQPISIPLCTDIAYNQTIMPNLLGHTNQEDAGLEVHQFYPLVKV
QCSPELRFFLCSMYAPVCTVLEQAIPPCRSICERARQGCEALMNKFGFQWPERLRCEH
FPRHGAEQICVGQNHSEDGAPALLTTAPPPGLQPGAGGTPGGPGGGGAPPRYATLEHP
FHCPRVLKVPSYLSYKFLGERDCAAPCEPARPDGSMFFSQEETRFARAEPRSSDKTHT
CPPCPAPEAEGAPSVFLFPPKPKDTLMISRTPEVTCVVVDVSHEDPEVKFNWYVDGV
EVHNAKTKPREEQYNSTYRVVSVLTVLHQDWLNGKEYKCAVSNKALPASIEKTISKA
KGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK Example 2

2-1. Transient Expression of hFZD2(X)-hFcm of SEQ ID NOs. 72-101 using hFZD2(X)-hFcm Recombinant Expression Vectors (X=140, 153-175, 178, 184, 190, 197, 210, 216, 222)

2-1-1. Preparation of Expression Vector Used for Gene Introduction

The hFZD2(X)-hFcm recombinant expression vectors obtained in Examples 1-1-3 and 1-1-5 were introduced into *Escherichia coli* DH5α, and DNAs were prepared from the transformants using a plasmid purification kit (Qiagen plasmid Maxi kit, QIAGEN K.K., Japan).

2-1-2. Introduction of Vectors into Culture Cells, Secretion and Expression

FreeStyle 293F cells (Invitrogen Japan K. K.) are cultured in FreeStyle 293 expression medium (Invitrogen Japan K. K.) at 37° C. in the presence of 5% CO2 at 125 rpm to reach a cell density of 2×105 to 3×106 cells/ml. When culture was conducted using 1 liter of medium, a solution comprising 35 ml of the Opti-MEM I reduced serum medium (Invitrogen Japan K. K.) added to 1 mg of the expression vector and a solution comprising 33.7 ml of the Opti-MEM I reduced serum medium added to 1.3 ml of the 293 fectin transfection reagent (Invitrogen Japan K. K.) were prepared, and the resulting solutions were incubated at room temperature for 5 minutes. These solutions were mixed with each other after incubation, and the resultant was incubated at room temperature for an additional about 25 minutes. Thereafter, the expression vector treated in the manner described above was added to a medium containing 1×10$^9$ cells/1 of FreeStyle 293F cells, and culture was conducted for 3 days.

2-1-3. Secretion Analysis of Culture Supernatant

To determine concentrations of fusion proteins of truncated forms of hFZD2 extracellular region protein and hFc variants by ELISA method, some of culture supernatant from Example 2-1-2 was recovered at Day 2. Test samples and a standard solution (in-house purified hFZD2(140)-hFcm recombinant) were added to a 96-well plate (Maxi Soap, Dow Corning Corporation) to which anti-human IgGs (γ-Chain Specific, available from Sigma Aldrich, Product No. I3382) were immobilized. Then, the plate was incubated at room temperature for 1 hour, and washed three times using T-PBS(−). Then, peroxidase-conjugated goat anti-human IgGs (Fc fragment) (available from Sigma Aldrich, Product No. A0170) were added thereto, and incubated at room temperature for 1 hour.

Then, the plate was washed four times using T-PBS(−), and color was developed using SUMILON peroxidase coloring kit (available from Sumitomo Bakelite Co., Ltd., Product No. ML-1120T). Absorbance was measured at 450 nm to determine the concentrations in the culture supernatant.

In this experiment, a concentration of hFZD2(140)-hFcm in the culture supernatant was 467.3±3.1 ng/mL. In contrast, concentrations of hFZD2(153)-hFcm to hFZD2(175)-hFcm in the culture supernatant were 1207.4±13.8, 1153.7±17.3, 1166.5±43.9, 1153.7±0.0, 1194.5±108.7, 1567.9±46.6, 1449.2±83.1, 1707.5±150.7, 1664.5±130.7, 1719.3±167.4, 1921.5±135.3, 1727.8±206.8, 1473.5±48.7, 1076.7±72.6, 1919.1±81.1, 2324.0±206.4, 1698.4±231.1, 1768.4±166.8, 1771.6±127.5, 1987.1±142.5, 1433.0±93.4, 1369.4±98.5, and 915.3±48.5 ng/mL, respectively. Also, concentrations of hFZD2(178)-hFcm, hFZD2(184)-hFcm, hFZD2(190)-hFcm, hFZD2(197)-hFcm, hFZD2(210)-hFcm and hFZD2 (216)-hFcm in the culture supernatant were 1370.1±44.6, 258.1±58.6, 75.3±5.3, 115.6±45.2, 80.2±5.2, and 93.2±4.8 ng/mL, respectively. From these results, it was demonstrated that hFZD2(153)-hFcm to hFZD2(175)-hFcm were present at high concentrations in the culture supernatant.

FIG. 3 shows a graph of concentrations of hFZD2(140)-hFcm, hFZD2(153)-hFcm to hFZD2(175)-hFcm, hFZD2 (178)-hFcm, hFZD2(184)-hFcm, hFZD2(190)-hFcm, hFZD2(197)-hFcm, hFZD2(210)-hFcm, and hFZD2(216)-hFcm in the culture supernatant As shown in FIG. 3, the secretion of hFZD2-hFcm recombinants was increased by extending the extracellular region protein by 153 amino acids in length. Also, it was suggested that this improvement in secretion was maintained by 175 amino acids in length.

2-2. Purification and Preparation of hFZD2(X)-hFcm Recombinants 2-2-1. Pre-Treatment of Culture Supernatant The supernatant of the culture solution obtained in Example 2-1-2 was recovered, filtered through a 0.22 μm filter (0.22 μm GP Express Membrane 500 mL, available from Millipore Corporation, Japan), and then cooled to 4° C.

2-2-2. Antibody Affinity Chromatography

An acidic buffer (pH 2.7) was prepared by dissolving 1.24 g boric acid (NACALAI TESQUE, INC., MW: 61.83), 7.16 g disodium hydrogen phosphate•12-hydrate (Wako Pure Chemical Industries, Ltd., MW: 358.14), 4.20 g citric acid•monohydrate (NACALAI TESQUE, INC., MW: 210.14) and 8.77 g sodium chloride (NACALAI TESQUE, INC., MW: 58.44) in Milli Q water and adding 15.55 mL of 1 M hydrochloric acid solution (prepared by 12 times diluting 12 N hydrochloric acid from Wako Pure Chemical Industries, Ltd. in Milli Q water), followed by making 1 L total volume using Milli Q water.

A neutral buffer (pH 7.3) was prepared by dissolving 1.24 g boric acid (NACALAI TESQUE, INC., MW: 61.83), 7.16 g disodium hydrogen phosphate. 12-hydrate (Wako Pure Chemical Industries, Ltd., MW: 358.14), 4.20 g citric acid•monohydrate (NACALAI TESQUE, INC., MW: 210.14) and 8.77 g sodium chloride (NACALAI TESQUE, INC., MW: 58.44) in Milli Q water and adding 11.7 mL of 5 M sodium hydroxide solution (prepared by dissolving 10 g sodium hydroxide from Wako Pure Chemical Industries, Ltd. (MW: 40.00) in Milli Q water to 50 mL total volume), followed by making 1 L total volume using Milli Q water.

A neutralizing buffer was prepared by dissolving 13.1 g sodium dihydrogen phosphate•dihydrate (KANTO CHEMICAL CO., LTD., MW: 156.01), 41.5 g disodium hydrogen phosphate•12-hydrate (Wako Pure Chemical Industries, Ltd., MW: 358.14) and 8.77 g sodium chloride (NACALAI TESQUE, INC., MW: 58.44) in Milli Q water such that a total volume becomes 1 L.

The pre-treated culture supernatant was applied to Protein A column (Hi Trap ProteinA HP 5 mL; available from GE healthcare bioscience, Co., Ltd., Japan) equilibrated using the neutral buffer (pH 7.3). Then, the column was washed using 25 mL or more of the neutral buffer (pH 7.3), followed by using 25 mL or more of a buffer prepared by adding NaCl to D-PBS(−) (NACALAI TESQUE, INC., Japan) at 1.85 M NaCl concentration. Then, the column was again washed using 25 mL of the neutral buffer (pH 7.3).

Then, the column was washed using 10 mL of 55% acidic buffer (pH 2.7). After washing, 70 mL of the acidic buffer (pH 2.7) was added over the column at 55% to 95% gradient to recover target proteins. The isolation and purification process was performed using AKTAexplorer10s or AKTA-purifier (GE healthcare bioscience, Co., Ltd., Japan). Before use, endotoxin was removed.

2-2-3. Preparation of Purified Authentic Sample

The purified authentic sample obtained in Example 2-2-2 was concentrated using an ultrafilter membrane VIVAS-PIN20 10,000 MWCO PES (Sartorius Stedim Japan K. K., Japan). Thereafter, the buffer in the sample was substituted with D-PBS(−) using NAP Columns (GE Healthcare Bio-Sciences Corp, Japan). After the completion of the concentration and substitution procedure, the resultant was filtered through a 0.22 gm filter (Millex GV, Millipore, Japan).

Concentrations of proteins were calculated from specific absorption coefficients by measuring A 280 nm. The specific absorption coefficients were as follows: hFZD2(140)-hFcm is E1%1 cm=9.7, hFZD2(159)-hFcm is E1%1 cm=9.4, hFZD2(165)-hFcm is E1%1 cm=9.3, hFZD2(171)-hFcm is E1%1 cm=9.4, and hFZD2(175)-hFcm is E1%1 cm=9.5.

2-3. Analysis of Mice Administrating the Recombinant hFZD2(X)-hFcm (X=140, 159, 165, 171, 175)

2-3-1. Administration to Mice

The hFZD2(X)-hFcm recombinant was administered to mice in order to evaluate physiological effects thereof on bone tissue. Mice used in this experiment were C57B6 mice (Charles River, Japan). For administration, the recombinant hFZD2(X)-hFcm was prepared at the protein concentration of 0.1 mg/mL in PBS. The formulation was administered to tail vein of each mouse at the dose of 10 mL/kg. Administration was performed total three times at the interval of 10 days.

Also, the group of mice subjected to PBS administration was used as a control group to compare osseous tissue changes. At Day 0, PBS administration was started. PBS was administrated to tail vein total three times at 10 days interval by Day 20. At Day 30, mice were subjected to necropsy.

2-3-2. Bone Structure Analysis (Three-Dimensional Microfocus X-Ray CT)

The left femur samples were obtained at necropsy, and the internal structure of the cancellous bone region of the distal femoral metaphysis was observed using a high-resolution microfocus X-ray CT scanner (micro-CT, Scan Xmate-L090, Comscantecno Co., Ltd.) and the analytic software (TRY 3D-BON, Ratoc System Engineering Co., Ltd.) in a non-invasive manner. The bone volume/tissue volume (BV/TV), the trabecular thickness (Tb. Th), the trabecular number (Tb. N), and the trabecular separation (Tb. Sp), were measured. The results are shown in Table 1.

TABLE 1

| hFZD2(X)-hFcm | Average of bone volume/ tissue volume (BV/TV, %) | Average of trabecular thickness (Tb. Th, μm) | Average of trabecular number (Tb. N, 1/mm) | Average of trabecular separation (Tb. Sp, μm) |
| --- | --- | --- | --- | --- |
| PBS | 18.1 ± 2.3 | 24.8 ± 1.9 | 7.2 ± 0.9 | 114.4 ± 16.0 |
| 140 | 20.2 ± 1.3 | 25.9 ± 0.9 | 7.8 ± 0.4 | 102.5 ± 6.8 |
| 159 | 24.0 ± 2.7 | 27.4 ± 1.7 | 8.7 ± 0.5 | 87.3 ± 7.6 |
| 165 | 22.4 ± 2.5 | 26.8 ± 1.7 | 8.3 ± 0.6 | 93.5 ± 9.0 |
| 171 | 20.8 ± 2.9 | 25.7 ± 1.9 | 8.1 ± 0.6 | 99.1 ± 10.4 |
| 175 | 21.3 ± 2.6 | 26.0 ± 2.0 | 8.1 ± 0.4 | 95.5 ± 7.4 |

As shown in Table 1, when observing the internal structure of the cancellous bone of the distal femoral metaphysis by micro CT, the bone volume/tissue volume (BV/TV) for the group administrating the recombinant hFZD2(140)-hFcm was 20.2±1.3%. In contrast, the bone volume/tissue volume for the groups administrating the recombinants hFZD2(159)-hFcm, hFZD2(165)-hFcm, hFZD2(171)-hFcm, and hFZD2(175)-hFcm was increased by 24.0±2.7, 22.4±2.5, 20.8±2.9, and 21.3±2.6%, respectively. Also, for the group administrating hFZD2(159)-hFcm and hFZD2(165)-hFcm, the trabecular thickness and the trabecular number were increased and the trabecular separation was decreased.

From these results, it is demonstrated that the increase of the bone volume/tissue volume, the trabecular thickness and the trabecular number and the decrease of the trabecular separation in the secondary cancellous bone of the femur metaphysis might be caused by extending the length of amino acids of the extracellular region protein of the recombinant hFZD2(140)-hFcm (Table 1).

All the publications, patents and patent applications cited herein are incorporated herein by reference in their entirety.

While the present invention has been described in detail and with reference to specific embodiments thereof, it will be apparent to one skill in the art that various changes and modifications can be made therein without departing from the spirit and scope thereof. This application is based on the Japanese patent application (No. 2011-137279), filed on Jun. 21, 2011, the entire contents of which are incorporated hereinto by reference.

INDUSTRIAL APPLICABILITY

According to the present invention, a protein comprising a truncated form of an extracellular region protein derived from Frizzled 2 which has improved secretion activity in production cells and bone mass-increasing activity can be produced. Further, by using said protein or DNA, a pharmaceutical composition for treating bone diseases can be effectively produced. Furthermore, a method for treating bone diseases, which uses the pharmaceutical composition, can be provided.

SEQUENCE LISTING

SEQ ID NO:3—Amino acid sequence of human IgG1 Fc variant
SEQ ID NO:4—Nucleotide sequence of DNA encoding human IgG1 Fc variant
SEQ ID NOs:5 and 6—Nucleotide sequences of sense origo DNAs
SEQ ID NOs7 and 8:—Nucleotide sequences of primers
SEQ ID NO:9—Nucleotide sequence of DNA encoding fusion protein
SEQ ID NO:10—Amino acid sequence of fusion protein
SEQ ID NOs:11 to 40—Nucleotide sequences of primers
SEQ ID NOs:42 to 71—Nucleotide sequences of DNAs encoding fusion proteins
SEQ ID NOs:72 to 101—Amino acid sequences of fusion proteins

The invention claimed is:

1. A fusion protein of
   (a) a protein comprising amino acids from the amino acid Q at position 1 of the N-terminal to any one amino acid of A at position 153, G at position 154, G at position 155, T at position 156, P at position 157, G at position 158, G at position 159, P at position 160, G at position 161, G at position 162, G at position 163, G at position 164, A at position 165, P at position 166, P at position 167, R at position 168, Y at position 169, A at position 170, T at position 171, L at position 172, E at position 173, H at position 174, or P at position 175 of the amino acid sequence of SEQ ID NO:1; and
   (b) a mammal-derived immunoglobulin Fc protein or a variant of the mammal-derived immunoglobulin Fc protein.

2. The fusion protein according to claim 1, wherein the mammal-derived immunoglobulin Fc protein consists of the amino acid sequence of SEQ ID NO:3.

3. A fusion protein comprising the amino acid sequence of any one of SEQ ID NOs: 72 to 94.

4. A pharmaceutical composition comprising the fusion protein according to claim 1.

5. A DNA encoding the fusion protein according to claim 1.

6. The DNA according to claim 5, wherein nucleotide sequence encoding the mammal-derived immunoglobulin Fc protein is the nucleotide sequences of SEQ ID NO:4.

7. A DNA consisting of the nucleotide sequence of any one of SEQ ID NOs: 42 to 64.

8. A pharmaceutical composition comprising the DNA according to claim 5.

9. A pharmaceutical composition comprising the fusion protein of claim 3.

10. A DNA encoding the fusion protein according to claim 1.

11. A pharmaceutical composition comprising the DNA according to claim 10.

* * * * *

```
                              SEQUENCE LISTING

<160> NUMBER OF SEQ ID NOS: 103

<210> SEQ ID NO 1
<211> LENGTH: 222
<212> TYPE: PRT
<213> ORGANISM: Homo sapiens

<400> SEQUENCE: 1

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Gly Thr Pro Gly Gly Pro
145                 150                 155                 160

Gly Gly Gly Gly Ala Pro Pro Arg Tyr Ala Thr Leu Glu His Pro Phe
                165                 170                 175

His Cys Pro Arg Val Leu Lys Val Pro Ser Tyr Leu Ser Tyr Lys Phe
            180                 185                 190

Leu Gly Glu Arg Asp Cys Ala Ala Pro Cys Glu Pro Ala Arg Pro Asp
        195                 200                 205

Gly Ser Met Phe Phe Ser Gln Glu Glu Thr Arg Phe Ala Arg
    210                 215                 220

<210> SEQ ID NO 2
<211> LENGTH: 666
<212> TYPE: DNA
<213> ORGANISM: Homo sapiens

<400> SEQUENCE: 2
cagttccacg gggagaaggg catctccatc ccggaccacg gcttctgcca gcccatctcc      60
```

```
atcccgctgt gcacggacat cgcctacaac cagaccatca tgcccaacct tctgggccac    120
acgaaccagg aggacgcagg cctagaggtg caccagttct atccgctggt gaaggtgcag    180
tgctcgcccg aactgcgctt cttcctgtgc tccatgtacg cacccgtgtg caccgtgctg    240
gaacaggcca tcccgccgtg ccgctctatc tgtgagcgcg cgcgccaggg ctgcgaagcc    300
ctcatgaaca agttcggttt tcagtggccc gagcgcctgc gctgcgagca cttcccgcgc    360
cacggcgccg agcagatctg cgtcggccag aaccactccg aggacggagc tcccgcgcta    420
ctcaccaccg cgccgccgcc gggactgcag ccgggtgccg ggggcacccc gggtggcccg    480
ggcggcggcg cgctcccccc gcgctacgcc acgctggagc ccccttcca ctgcccgcgc    540 gtcctcaagg tgccatccta tctcagctac aagtttctgg gcgagcgtga ttgtgctgcg    600
ccctgcgaac tgcgcggcc cgatggttcc atgttcttct cacaggagga gacgcgtttc    660
gcgcgc                                                                666
```

<210> SEQ ID NO 3
<211> LENGTH: 233
<212> TYPE: PRT
<213> ORGANISM: Artificial
<220> FEATURE:
<223> OTHER INFORMATION: Syntheic construct of human IgG1 Fc variant

<400> SEQUENCE: 3

```
Ala Glu Pro Arg Ser Ser Asp Lys Thr His Thr Cys Pro Pro Cys Pro
1               5                   10                  15

Ala Pro Glu Ala Glu Gly Ala Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Ala Val Ser Asn Lys
            100                 105                 110

Ala Leu Pro Ala Ser Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 4

<211> LENGTH: 702
<212> TYPE: DNA
<213> ORGANISM: Artificial
<220> FEATURE:
<223> OTHER INFORMATION: Syntheic construct of human IgG1 Fc variant

<400> SEQUENCE: 4

```
gccgagccta ggtcttcaga caaaactcac acatgcccac cgtgcccagc acctgaagcc      60
gagggggccc cgtcagtctt cctcttcccc ccaaaaccca aggacaccct catgatctcc     120
cggacccctg aggtcacatg cgtggtggtg gacgtgagcc acgaagaccc tgaggtcaag     180
ttcaactggt acgtggacgg cgtggaggtg cataatgcca agacaaagcc gcgggaggag     240
cagtacaaca gcacgtaccg tgtggtcagc gtcctcaccg tcctgcacca ggactggctg     300
aatggcaagg agtacaagtg cgccgtctcc aacaaagccc tcccagcctc catcgagaaa     360
accatctcca aagccaaagg gcagccccga gaaccacagg tgtacaccct gcccccatcc     420
cgggatgagc tgaccaagaa ccaggtcagc ctgacctgcc tggtcaaagg cttctatccc     480
agcgacatcg ccgtggagtg ggagagcaat gggcagccgg agaacaacta caagaccacg     540
cctcccgtgc tggactccga cggctccttc ttcctctaca gcaagctcac cgtggacaag     600
agcaggtggc agcaggggaa cgtcttctca tgctccgtga tgcatgaggc tctgcacaac     660
cactacacgc agaagagcct ctccctgtct ccgggtaaat ga                         702
```

<210> SEQ ID NO 5
<211> LENGTH: 63
<212> TYPE: DNA
<213> ORGANISM: Artificial
<220> FEATURE:
<223> OTHER INFORMATION: antisense oligoDNA

<400> SEQUENCE: 5

```
gatccgctag cgtcgacggt aagcctatcc ctaaccctct cctcggtctc gattctacgt      60
gac                                                                    63
```

<210> SEQ ID NO 6
<211> LENGTH: 63
<212> TYPE: DNA
<213> ORGANISM: Artificial
<220> FEATURE:
<223> OTHER INFORMATION: antisense oligoDNA

<400> SEQUENCE: 6

```
tcgagtcacg tagaatcgag accgaggaga gggttaggga taggcttacc gtcgacgcta      60
gcg                                                                    63
```

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7

```
cgggatccac catgcggccc cgcagcgccc                                        30
```

<210> SEQ ID NO 8
<211> LENGTH: 35
<212> TYPE: DNA
<213> ORGANISM: Artificial
<220> FEATURE:
<223> OTHER INFORMATION: primer -continued

<400> SEQUENCE: 8
atagtttagc ggccgctcat ttacccggag acagg                                 35

<210> SEQ ID NO 9
<211> LENGTH: 1191
<212> TYPE: DNA
<213> ORGANISM: Artificial
<220> FEATURE:
<223> OTHER INFORMATION: DNA encoding fusion protein

<400> SEQUENCE: 9

```
atgcggcccc gcagcgccct gccccgcctg ctgctgccgc tgctgctgct gcccgccgcc    60
gggccggccc agttccacgg ggagaagggc atctccatcc cggaccacgg cttctgccag   120
cccatctcca tcccgctgtg cacggacatc gcctacaacc agaccatcat gcccaacctt   180
ctgggccaca cgaaccagga ggacgcaggc ctagaggtgc accagttcta ccgctggtg    240
aaggtgcagt gctcgcccga actgcgcttc ttcctgtgct ccatgtacgc acccgtgtgc   300
accgtgctgg aacaggccat cccgccgtgc cgctctatct gtgagcgcgc gcgccagggc   360
tgcgaagccc tcatgaacaa gttcggtttt cagtggcccg agcgcctgcg ctgcgagcac   420
ttcccgcgcc acggcgccga gcagatctgc gtcggccaga accactccga ggacggagct   480
cccgcgctag ccgagcctag gtcttcagac aaaactcaca catgcccacc gtgcccagca   540
cctgaagccg agggggcccc gtcagtcttc ctcttccccc caaaacccaa ggacaccctc   600
atgatctccc ggacccctga ggtcacatgc gtggtggtgg acgtgagcca cgaagaccct   660
gaggtcaagt tcaactggta cgtggacggc gtggaggtgc ataatgccaa gacaaagccg   720
cgggaggagc agtacaacag cacgtaccgt gtggtcagcg tcctcaccgt cctgcaccag   780
gactggctga atggcaagga gtacaagtgc gccgtctcca acaaagccct cccagcctcc   840
atcgagaaaa ccatctccaa agccaaaggg cagccccgag aaccacaggt gtacaccctg   900
cccccatccc gggatgagct gaccaagaac caggtcagcc tgacctgcct ggtcaaaggc   960
ttctatccca gcgacatcgc cgtggagtgg gagagcaatg ggcagccgga gaacaactac  1020
aagaccacgc ctcccgtgct ggactccgac ggctccttct tcctctacag caagctcacc  1080
gtggacaaga gcaggtggca gcaggggaac gtcttctcat gctccgtgat gcatgaggct  1140
ctgcacaacc actacacgca gaagagcctc tccctgtctc cgggtaaatg a           1191
```

<210> SEQ ID NO 10
<211> LENGTH: 396
<212> TYPE: PRT
<213> ORGANISM: Artificial
<220> FEATURE:
<223> OTHER INFORMATION: fusion protein

<400> SEQUENCE: 10

Met Arg Pro Arg Ser Ala Leu Pro Arg Leu Leu Leu Pro Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
        35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
            85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
            115                 120                 125

Gly Phe Gln Trp Pro Glu Arg Leu Arg Cys Glu His Phe Pro Arg His
            130                 135                 140

Gly Ala Glu Gln Ile Cys Val Gly Gln Asn His Ser Glu Asp Gly Ala
145                 150                 155                 160

Pro Ala Leu Ala Glu Pro Arg Ser Ser Asp Lys Thr His Thr Cys Pro
            165                 170                 175

Pro Cys Pro Ala Pro Glu Ala Glu Gly Ala Pro Ser Val Phe Leu Phe
            180                 185                 190

Pro Pro Lys Pro Lys Asp Thr Leu Met Ile Ser Arg Thr Pro Glu Val
            195                 200                 205

Thr Cys Val Val Val Asp Val Ser His Glu Asp Pro Glu Val Lys Phe
            210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
            245                 250                 255

Val Leu His Gln Asp Trp Leu Asn Gly Lys Glu Tyr Lys Cys Ala Val
            260                 265                 270

Ser Asn Lys Ala Leu Pro Ala Ser Ile Glu Lys Thr Ile Ser Lys Ala
            275                 280                 285

Lys Gly Gln Pro Arg Glu Pro Gln Val Tyr Thr Leu Pro Pro Ser Arg
            290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
            325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
            355                 360                 365

Gly Asn Val Phe Ser Cys Ser Val Met His Glu Ala Leu His Asn His
            370                 375                 380

Tyr Thr Gln Lys Ser Leu Ser Leu Ser Pro Gly Lys
385                 390                 395

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
cgcctaggct cggcgccacc cggggtgccc                                    30

<210> SEQ ID NO 12
<211> LENGTH: 30
<212> TYPE: DNA
<213> ORGANISM: Artificial
<220> FEATURE:

<223> OTHER INFORMATION: primer

<400> SEQUENCE: 12
cgcctaggct cggccccggc acccggctgc                                              30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
cgcctaggct cggcgccccc ggcacccggc                                              30

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
cgcctaggct cggcggtgcc cccggcaccc                                              30

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
cgcctaggct cggccggggt gcccccggca                                              30

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
cgcctaggct cggcacccgg ggtgcccccg                                              30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
cgcctaggct cggcgccacc cggggtgccc                                              30

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
cgcctaggct cggccgggcc acccggggtg                                              30

```
<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
cgcctaggct cggcgcccgg gccacccggg                                    30

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
cgcctaggct cggcgccgcc cgggccaccc                                    30

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
cgcctaggct cggcgccgcc gcccgggcca                                    30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
cgcctaggct cggcgccgcc gccgcccggg                                    30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
cgcctaggct cggcagcgcc gccgccgccc                                    30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
cgcctaggct cggcgggagc gccgccgccg                                    30

<210> SEQ ID NO 25
<211> LENGTH: 30
<212> TYPE: DNA
<213> ORGANISM: Artificial
<220> FEATURE:
<223> OTHER INFORMATION: primer
```

<400> SEQUENCE: 25
cgcctaggct cggccggggg agcgccgccg                                               30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
cgcctaggct cggcgcgcgg gggagcgccg                                               30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
cgcctaggct cggcgtagcg cggggagcg                                                30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
cgcctaggct cggcggcgta gcgcggggga                                               30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
cgcctaggct cggccgtggc gtagcgcggg                                               30

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
cgcctaggct cggccagcgt ggcgtagcgc                                               30

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
cgcctaggct cggcctccag cgtggcgtag                                               30

<210> SEQ ID NO 32
<211> LENGTH: 30

```
<212> TYPE: DNA
<213> ORGANISM: Artificial
<220> FEATURE:
<223> OTHER INFORMATION: primer

<400> SEQUENCE: 32
cgcctaggct cggcgtgctc cagcgtggcg                                    30

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
cgcctaggct cggcggggtg ctccagcgtg                                    30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
cgcctaggct cggcgcagtg aaggggtgc                                     30

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
cgcctaggct cggccaccttg aggacgcgc                                    30

<210> SEQ ID NO 36
<211> LENGTH: 30
<212> TYPE: DNA
<213> ORGANISM: Artificial
<220> FEATURE:
<223> OTHER INFORMATION: primer

<400> SEQUENCE: 36
cgcctaggct cggcgtagct gagataggat                                    30

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
cgcctaggct cggcatcacg ctcgcccaga                                    30

<210> SEQ ID NO 38
<211> LENGTH: 30
<212> TYPE: DNA
<213> ORGANISM: Artificial
<220> FEATURE:
<223> OTHER INFORMATION: primer

<400> SEQUENCE: 38
```
cgcctaggct cggcggaacc atcgggccgc                                      30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
cgcctaggct cggcctcctg tgagaagaac                                      30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
cgcctaggct cggcgcgcgc gaaacgcgtc                                      30

<210> SEQ ID NO 41
<211> LENGTH: 1698
<212> TYPE: DNA
<213> ORGANISM: Homo sapiens

<400> SEQUENCE: 41
atgcggcccc gcagcgccct gccccgcctg ctgctgccgc tgctgctgct gcccgccgcc     60
gggccggccc agttcacgg ggagaagggc atctccatcc ggaccacgg cttctgccag     120
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg gggcaccccg    540
ggtggcccgg gcgcggcgg cgctccccg cgctacgcca cgctggagca ccccttccac    600
tgcccgcgcg tcctcaaggt gccatcctat ctcagctaca gtttctgggt cgagcgtgat    660
tgtgctgcgc cctgcgaacc tgcgcggccc gatggttcca tgttcttctc acaggaggag    720
acgcgtttcg cgcgcctctg gatcctcacc tggtcggtgc tgtgctgcgc ttccaccttc    780
ttcactgtca ccacgtactt ggtagacatg cagcgcttcc gctacccaga gcggcctatc    840
atttttctgt cgggctgcta caccatggtg tcggtggcct acatcgcggg cttcgtgctc    900
caggagcgcg tggtgtgcaa cgagcgcttc tccgaggacg gttaccgcac ggtggtgcag    960
ggcaccaaga aggagggctg caccatcctc ttcatgatgc tctacttctt cagcatggcc    1020
agctccatct ggtgggtcat cctgtcgctc acctggttcc tggcagccgg catgaagtgg    1080
ggccacgagg ccatcgaggc caactctcag tacttccacc tggccgcctg gccgtgccg    1140
gccgtcaaga ccatcaccat cctggccatg ggccagatcg acggcgacct gctgagcggc    1200
gtgtgcttcg taggcctcaa cagcctggac ccgctgcggg gcttcgtgct agcgccgctc    1260
ttcgtgtacc tgttcatcgg cacgtccttc ctcctggccg gcttcgtgtc gctcttccgc    1320
atccgcacca tcatgaagca cgacggcacc aagaccgaaa agctggagcg gctcatggtg    1380

| | |
|---|---|
| cgcatcggcg tcttctccgt gctctacaca gtgcccgcca ccatcgtcat cgcttgctac | 1440 |
| ttctacgagc aggccttccg cgagcactgg gagcgctcgt gggtgagcca gcactgcaag | 1500 |
| agcctggcca tcccgtgccc ggcgcactac acgccgcgca tgtcgcccga cttcacggtc | 1560 |
| tacatgatca aatacctcat gacgctcatc gtgggcatca cgtcgggctt ctggatctgg | 1620 |
| tcgggcaaga cgctgcactc gtggaggaag ttctacactc gcctcaccaa cagccgacac | 1680 |
| ggtgagacca ccgtgtga | 1698 |

<210> SEQ ID NO 42
<211> LENGTH: 1230
<212> TYPE: DNA
<213> ORGANISM: Artificial
<220> FEATURE:
<223> OTHER INFORMATION: DNA encoding fusion protein

<400> SEQUENCE: 42

| | |
|---|---|
| atgcggcccc gcagcgccct gccccgcctg ctgctgccgc tgctgctgct gcccgccgcc | 60 |
| gggccggccc agttccacgg ggagaagggc atctccatcc cggaccacgg cttctgccag | 120 |
| cccatctcca tcccgctgtg cacggacatc gcctacaacc agaccatcat gcccaacctt | 180 |
| ctgggccaca cgaaccagga ggacgcaggc ctagaggtgc accagttcta tccgctggtg | 240 |
| aaggtgcagt gctcgcccga actgcgcttc ttcctgtgct ccatgtacgc acccgtgtgc | 300 |
| accgtgctgg aacaggccat cccgccgtgc cgctctatct gtgagcgcgc gcgccagggc | 360 |
| tgcgaagccc tcatgaacaa gttcggtttt cagtggcccg agcgcctgcg ctgcgagcac | 420 |
| ttcccgcgcc acggcgccga gcagatctgc gtcggccaga accactccga ggacggagct | 480 |
| cccgcgctac tcaccaccgc gccgccgccg ggactgcagc cgggtgccgc cgagcctagg | 540 |
| tcttcagaca aaactcacac atgcccaccg tgcccagcac ctgaagccga ggggccccg | 600 |
| tcagtcttcc tcttcccccc aaaacccaag gacaccctca tgatctcccg gacccctgag | 660 |
| gtcacatgcg tggtggtgga cgtgagccac gaagaccctg aggtcaagtt caactggtac | 720 |
| gtggacggcg tggaggtgca taatgccaag acaaagccgc gggaggagca gtacaacagc | 780 |
| acgtaccgtg tggtcagcgt cctcaccgtc ctgcaccagg actggctgaa tggcaaggag | 840 |
| tacaagtgcg ccgtctccaa caaagccctc ccagcctcca tcgagaaaac catctccaaa | 900 |
| gccaaagggc agccccgaga accacaggtg tacaccctgc ccccatcccg ggatgagctg | 960 |
| accaagaacc aggtcagcct gacctgcctg gtcaaaggct tctatcccag cgacatcgcc | 1020 |
| gtggagtggg agagcaatgg gcagccggag aacaactaca agaccacgcc tcccgtgctg | 1080 |
| gactccgacg gctccttctt cctctacagc aagctcaccg tggacaagag caggtggcag | 1140 |
| caggggaacg tcttctcatg ctccgtgatg catgaggctc tgcacaacca ctacacgcag | 1200 |
| aagagcctct ccctgtctcc gggtaaatga | 1230 |

<210> SEQ ID NO 43
<211> LENGTH: 1233
<212> TYPE: DNA
<213> ORGANISM: Artificial
<220> FEATURE:
<223> OTHER INFORMATION: DNA encoding human fusion protein

<400> SEQUENCE: 43

| | |
|---|---|
| atgcggcccc gcagcgccct gccccgcctg ctgctgccgc tgctgctgct gcccgccgcc | 60 |
| gggccggccc agttccacgg ggagaagggc atctccatcc cggaccacgg cttctgccag | 120 |

```
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg ggccgagcct    540
aggtcttcag acaaaactca cacatgccca ccgtgcccag cacctgaagc cgagggggcc    600
ccgtcagtct tcctcttccc cccaaaaccc aaggacaccc tcatgatctc ccggacccct    660
gaggtcacat gcgtggtggt ggacgtgagc cacgaagacc ctgaggtcaa gttcaactgg    720
tacgtggacg gcgtggaggt gcataatgcc aagacaaagc cgcgggagga gcagtacaac    780
agcacgtacc gtgtggtcag cgtcctcacc gtcctgcacc aggactggct gaatggcaag    840
gagtacaagt gcgccgtctc caacaaagcc ctcccagcct ccatcgagaa aaccatctcc    900
aaagccaaag ggcagccccg agaaccacag gtgtacaccc tgcccccatc ccgggatgag    960
ctgaccaaga accaggtcag cctgacctgc ctggtcaaag gcttctatcc cagcgacatc    1020
gccgtggagt gggagagcaa tgggcagccg gagaacaact acaagaccac gcctcccgtg    1080
ctggactccg acggctcctt cttcctctac agcaagctca ccgtggacaa gagcaggtgg    1140
cagcagggga acgtcttctc atgctccgtg atgcatgagg ctctgcacaa ccactacacg    1200
cagaagagcc tctccctgtc tccgggtaaa tga                                 1233

<210> SEQ ID NO 44
<211> LENGTH: 1236
<212> TYPE: DNA
<213> ORGANISM: Artificial
<220> FEATURE:
<223> OTHER INFORMATION: DNA encoding fusion protein

<400> SEQUENCE: 44
atgcggcccc gcagcgccct gccccgcctg ctgctgccgc tgctgctgct gcccgccgcc     60
gggccggccc agttccacgg ggagaagggc atctccatcc ggaccacgg cttctgccag    120 cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg ggcgccgag    540 cctaggtctt cagacaaaac tcacacatgc ccaccgtgcc cagcacctga gccgaggggg    600
gccccgtcag tcttcctctt cccccccaaaa cccaaggaca ccctcatgat ctcccggacc    660
cctgaggtca catgcgtggt ggtggacgtg agccacgaag accctgaggt caagttcaac    720
tggtacgtgg acggcgtgga ggtgcataat gccaagacaa agccgcggga ggagcagtac    780
aacagcacgt accgtgtggt cagcgtcctc accgtcctgc accaggactg gctgaatggc    840
aaggagtaca agtgcgccgt ctccaacaaa gccctcccag cctccatcga gaaaaccatc    900
tccaaagcca aagggcagcc ccgagaacca caggtgtaca ccctgccccc atcccgggat    960
```

```
gagctgacca agaaccaggt cagcctgacc tgcctggtca aaggcttcta tcccagcgac    1020
atcgccgtgg agtgggagag caatgggcag ccggagaaca actacaagac cacgcctccc    1080
gtgctggact ccgacggctc cttcttcctc tacagcaagc tcaccgtgga caagagcagg    1140
tggcagcagg ggaacgtctt ctcatgctcc gtgatgcatg aggctctgca caaccactac    1200
acgcagaaga gcctctccct gtctccgggt aaatga                              1236

<210> SEQ ID NO 45
<211> LENGTH: 1239
<212> TYPE: DNA
<213> ORGANISM: Artificial
<220> FEATURE:
<223> OTHER INFORMATION: DNA encoding fusion protein

<400> SEQUENCE: 45
atgcggcccc gcagcgccct gccccgcctg ctgctgccgc tgctgctgct gcccgccgcc     60
gggccggccc agttccacgg ggagaagggc atctccatcc cggaccacgg cttctgccag    120
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg gggcaccgcc    540
gagcctaggt cttcagacaa aactcacaca tgcccaccgt gcccagcacc tgaagccgag    600
ggggccccgt cagtcttcct cttccccccaa aacccaagg acaccctcat gatctcccgg    660
acccctgagg tcacatgcgt ggtggtggac gtgagccacg aagaccctga ggtcaagttc    720
aactggtacg tggacggcgt ggaggtgcat aatgccaaga caaagccgcg ggaggagcag    780
tacaacagca cgtaccgtgt ggtcagcgtc ctcaccgtcc tgcaccagga ctggctgaat    840
ggcaaggagt acaagtgcgc cgtctccaac aaagccctcc cagcctccat cgagaaaacc    900
atctccaaag ccaaagggca gccccgagaa ccacaggtgt acaccctgcc cccatcccgg    960
gatgagctga ccaagaacca ggtcagcctg acctgcctgg tcaaaggctt ctatcccagc    1020
gacatcgccg tggagtggga gagcaatggg cagccggaga caactacaa gaccacgcct    1080 cccgtgctga ctccgacgg ctccttcttc ctctacagca agctcaccgt ggacaagagc    1140
aggtggcagc aggggaacgt cttctcatgc tccgtgatgc atgaggctct gcacaaccac    1200
tacacgcaga agagcctctc cctgtctccg ggtaaatga                          1239

<210> SEQ ID NO 46
<211> LENGTH: 1242
<212> TYPE: DNA
<213> ORGANISM: Artificial
<220> FEATURE:
<223> OTHER INFORMATION: DNA encoding fusion protein

<400> SEQUENCE: 46
atgcggcccc gcagcgccct gccccgcctg ctgctgccgc tgctgctgct gcccgccgcc     60
gggccggccc agttccacgg ggagaagggc atctccatcc cggaccacgg cttctgccag    120
cccatctcca tcccgctgtg cacggacatc gcctacaacc agaccatcat gcccaacctt    180
```

```
ctgggccaca cgaaccagga ggacgcaggc ctagaggtgc accagttcta tccgctggtg      240
aaggtgcagt gctcgcccga actgcgcttc ttcctgtgct ccatgtacgc acccgtgtgc      300
accgtgctgg aacaggccat cccgccgtgc cgctctatct gtgagcgcgc gcgccagggc      360
tgcgaagccc tcatgaacaa gttcggtttt cagtggcccg agcgcctgcg ctgcgagcac      420
ttcccgcgcc acggcgccga gcagatctgc gtcggccaga accactccga ggacggagct      480
cccgcgctac tcaccaccgc gccgccgccg ggactgcagc cgggtgccgg ggcaccccg       540 gccgagccta ggtcttcaga caaaactcac acatgcccac cgtgcccagc acctgaagcc      600
gagggggccc cgtcagtctt cctcttcccc ccaaaaccca aggacaccct catgatctcc      660
cggacccctg aggtcacatg cgtggtggtg gacgtgagcc acgaagaccc tgaggtcaag      720
ttcaactggt acgtggacgg cgtggaggtg cataatgcca agacaaagcc gcggaggag       780 cagtacaaca gcacgtaccg tgtggtcagc gtcctcaccg tcctgcacca ggactggctg      840
aatggcaagg agtacaagtg cgccgtctcc aacaaagccc tcccagcctc catcgagaaa      900
accatctcca agccaaagg gcagcccga gaaccacagg tgtacaccct gccccatcc        960 cgggatgagc tgaccaagaa ccaggtcagc ctgacctgcc tggtcaaagg cttctatccc     1020
agcgacatcg ccgtggagtg ggagagcaat gggcagccgg agaacaacta caagaccacg     1080
cctcccgtgc tggactccga cggctccttc ttcctctaca gcaagctcac cgtggacaag     1140
agcaggtggc agcaggggaa cgtcttctca tgctccgtga tgcatgaggc tctgcacaac     1200
cactacacgc agaagagcct ctccctgtct ccgggtaaat ga                        1242
```

<210> SEQ ID NO 47
<211> LENGTH: 1245
<212> TYPE: DNA
<213> ORGANISM: Artificial
<220> FEATURE:
<223> OTHER INFORMATION: DNA encoding fusion protein

<400> SEQUENCE: 47

```
atgcggcccc gcagcgccct gccccgcctg ctgctgccgc tgctgctgct gccgccgcc        60 gggccggccc agttccacgg ggagaagggc atctccatcc ggaccacgg cttctgccag       120 cccatctcca tcccgctgtg cacggacatc gcctacaacc agaccatcat gcccaacctt      180
ctgggccaca cgaaccagga ggacgcaggc ctagaggtgc accagttcta tccgctggtg     240
aaggtgcagt gctcgcccga actgcgcttc ttcctgtgct ccatgtacgc acccgtgtgc      300
accgtgctgg aacaggccat cccgccgtgc cgctctatct gtgagcgcgc gcgccagggc     360
tgcgaagccc tcatgaacaa gttcggtttt cagtggcccg agcgcctgcg ctgcgagcac     420
ttcccgcgcc acggcgccga gcagatctgc gtcggccaga accactccga ggacggagct    480
cccgcgctac tcaccaccgc gccgccgccg ggactgcagc cgggtgccgg ggcaccccg      540 ggtgccgagc ctaggtcttc agacaaaact cacacatgcc caccgtgccc agcacctgaa    600
gccgaggggg cccgtcagt cttcctcttc ccccaaaac caaggacac cctcatgatc      660 tcccggaccc ctgaggtcac atgcgtggtg gtggacgtga gccacgaaga ccctgaggtc    720
aagttcaact ggtacgtgga cggcgtggag gtgcataatg ccaagacaaa gccgcgggag    780
gagcagtaca acagcacgta ccgtgtggtc agcgtcctca ccgtcctgca ccaggactgg    840
ctgaatggca aggagtacaa gtgcgccgtc tccaacaaag ccctcccagc ctccatcgag    900
aaaaccatct ccaagccaaa gggcagcccc gagaaccac aggtgtacac cctgccccca    960
tcccgggatg agctgaccaa gaaccaggtc agcctgacct gcctggtcaa aggcttctat   1020
```

```
cccagcgaca tcgccgtgga gtgggagagc aatgggcagc cggagaacaa ctacaagacc    1080
acgcctcccg tgctggactc cgacggctcc ttcttcctct acagcaagct caccgtggac    1140
aagagcaggt ggcagcaggg gaacgtcttc tcatgctccg tgatgcatga ggctctgcac    1200
aaccactaca cgcagaagag cctctccctg tctccgggta aatga                     1245
```

<210> SEQ ID NO 48
<211> LENGTH: 1248
<212> TYPE: DNA
<213> ORGANISM: Artificial
<220> FEATURE:
<223> OTHER INFORMATION: DNA encoding fusion protein

<400> SEQUENCE: 48

```
atgcggcccc gcagcgccct gccccgcctg ctgctgccgc tgctgctgct gcccgccgcc     60
gggccggccc agttccacgg ggagaagggc atctccatcc ggaccacgg cttctgccag     120 cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg ggcaccccg     540 ggtggcgccg agcctaggtc ttcagacaaa actcacacat gcccaccgtg cccagcacct    600
gaagccgagg ggccccgtc agtcttcctc ttccccccaa acccaaggga caccctcatg     660
atctccggga ccccctgaggt cacatgcgtg gtggtggacg tgagccacga agaccctgag    720
gtcaagttca actggtacgt ggacggcgtg gaggtgcata atgccaagac aaagccgcgg    780
gaggagcagt acaacagcac gtaccgtgtg gtcagcgtcc tcaccgtcct gcaccaggac    840
tggctgaatg gcaaggagta caagtgcgcc gtctccaaca agccctccc agcctccatc     900 gagaaaacca tctccaaagc caaagggcag ccccgagaac cacaggtgta caccctgccc    960
ccatcccggg atgagctgac caagaaccag gtcagcctga cctgcctggt caaaggcttc    1020
tatcccagcg acatcgccgt ggagtgggag agcaatgggc agccggagaa caactacaag    1080
accacgcctc ccgtgctgga ctccgacggc tccttcttcc tctacagcaa gctcaccgtg    1140
gacaagagca ggtggcagca ggggaacgtc ttctcatgct ccgtgatgca tgaggctctg    1200
cacaaccact acacgcagaa gagcctctcc ctgtctccgg gtaaatga                 1248
```

<210> SEQ ID NO 49
<211> LENGTH: 1251
<212> TYPE: DNA
<213> ORGANISM: Artificial
<220> FEATURE:
<223> OTHER INFORMATION: DNA encoding fusion protein

<400> SEQUENCE: 49

```
atgcggcccc gcagcgccct gccccgcctg ctgctgccgc tgctgctgct gcccgccgcc     60
gggccggccc agttccacgg ggagaagggc atctccatcc ggaccacgg cttctgccag     120 cccatctcca tcccgctgtg cacggacatc gcctacaacc agaccatcat gcccaacctt    180
ctgggccaca cgaaccagga ggacgcaggc ctagaggtgc accagttcta tccgctggtg    240
```

```
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg gggcaccccg    540
ggtggcccgg ccgagcctag gtcttcagac aaaactcaca catgcccacc gtgcccagca    600
cctgaagccg agggggcccc gtcagtcttc ctcttccccc aaaacccaa ggacaccctc    660 atgatctccc ggacccctga ggtcacatgc gtggtggtgg acgtgagcca cgaagaccct    720
gaggtcaagt tcaactggta cgtggacggc gtggaggtgc ataatgccaa gacaaagccg    780
cgggaggagc agtacaacag cacgtaccgt gtggtcagcg tcctcaccgt cctgcaccag    840
gactggctga atggcaagga gtacaagtgc gccgtctcca acaaagccct cccagcctcc    900
atcgagaaaa ccatctccaa agccaaaggg cagccccgag aaccacaggt gtacaccctg    960
cccccatccc gggatgagct gaccaagaac caggtcagcc tgacctgcct ggtcaaaggc   1020
ttctatccca gcgacatcgc cgtggagtgg gagagcaatg ggcagccgga gaacaactac   1080
aagaccacgc ctcccgtgct ggactccgac ggctccttct tcctctacag caagctcacc   1140
gtggacaaga gcaggtggca gcaggggaac gtcttctcat gctccgtgat gcatgaggct   1200
ctgcacaacc actacacgca gaagagcctc tccctgtctc cgggtaaatg a           1251

<210> SEQ ID NO 50
<211> LENGTH: 1254
<212> TYPE: DNA
<213> ORGANISM: Artificial
<220> FEATURE:
<223> OTHER INFORMATION: DNA encoding fusion protein

<400> SEQUENCE: 50
atgcggcccc gcagcgccct gccccgcctg ctgctgccgc tgctgctgct gcccgccgcc     60
gggccggccc agttccacgg ggagaagggc atctccatcc cggaccacgg cttctgccag    120
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg gggcaccccg    540
ggtggcccgg cgccgagcc taggtcttca gacaaaactc acacatgccc accgtgccca    600
gcacctgaag ccgaggggc ccgtcagtc ttcctcttcc ccccaaaacc caaggacacc    660
ctcatgatct cccggacccc tgaggtcaca tgcgtggtgg tggacgtgag ccacgaagac    720
cctgaggtca agttcaactg gtacgtggac ggcgtggagg tgcataatgc caagacaaag    780
ccgcgggagg agcagtacaa cagcacgtac cgtgtggtca gcgtcctcac cgtcctgcac    840
caggactggc tgaatggcaa ggagtacaag tgcgccgtct ccaacaaagc cctcccagcc    900
tccatcgaga aaaccatctc caaagccaaa gggcagcccc gagaaccaca ggtgtacacc    960
ctgcccccat cccgggatga gctgaccaag aaccaggtca gcctgacctg cctggtcaaa   1020
ggcttctatc ccagcgacat cgccgtggag tgggagagca atgggcagcc ggagaacaac   1080
```

```
tacaagacca cgcctcccgt gctggactcc gacggctcct tcttcctcta cagcaagctc    1140
accgtggaca agagcaggtg gcagcagggg aacgtcttct catgctccgt gatgcatgag    1200
gctctgcaca accactacac gcagaagagc ctctccctgt ctccgggtaa atga          1254
```

<210> SEQ ID NO 51
<211> LENGTH: 1257
<212> TYPE: DNA
<213> ORGANISM: Artificial
<220> FEATURE:
<223> OTHER INFORMATION: DNA encoding fusion protein

<400> SEQUENCE: 51

```
atgcggcccc gcagcgccct gccccgcctg ctgctgccgc tgctgctgct gcccgccgcc     60
gggccggccc agttccacgg ggagaagggc atctccatcc cggaccacgg cttctgccag    120
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc accgtgtgc     300 accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg gggcaccccg    540
ggtggcccgg gcgcgccga gcctaggtct tcagacaaaa ctcacacatg cccaccgtgc    600
ccagcacctg aagccgaggg ggccccgtca gtcttcctct tccccccaaa acccaaggac    660
accctcatga tctcccggac ccctgaggtc acatgcgtgg tggtggacgt gagccacgaa    720
gaccctgagg tcaagttcaa ctggtacgtg gacggcgtgg aggtgcataa tgccaagaca    780
aagccgcggg aggagcagta caacagcacg taccgtgtgg tcagcgtcct caccgtcctg    840
caccaggact ggctgaatgg caaggagtac aagtgcgccg tctccaacaa agccctccca    900
gcctccatcg agaaaaccat ctccaaagcc aaagggcagc ccgagaacca caggtgtac    960 accctgcccc catcccggga tgagctgacc aagaaccagg tcagcctgac ctgcctggtc   1020
aaaggcttct atcccagcga catcgccgtg gagtgggaga gcaatgggca gccggagaac   1080
aactacaaga ccacgcctcc cgtgctggac tccgacggct ccttcttcct ctacagcaag   1140
ctcaccgtgg acaagagcag gtggcagcag gggaacgtct tctcatgctc cgtgatgcat   1200
gaggctctgc acaaccacta cacgcagaag agcctctccc tgtctccggg taaatga     1257
```

<210> SEQ ID NO 52
<211> LENGTH: 1260
<212> TYPE: DNA
<213> ORGANISM: Artificial
<220> FEATURE:
<223> OTHER INFORMATION: DNA encoding fusion protein

<400> SEQUENCE: 52

```
atgcggcccc gcagcgccct gccccgcctg ctgctgccgc tgctgctgct gcccgccgcc     60
gggccggccc agttccacgg ggagaagggc atctccatcc cggaccacgg cttctgccag    120
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc accgtgtgc     300
```

```
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg ggcaccccg     540 ggtggcccgg gcggcggcgc cgagcctagg tcttcagaca aaactcacac atgcccaccg    600
tgcccagcac ctgaagccga gggggccccg tcagtcttcc tcttccccc aaaacccaag     660 gacaccctca tgatctcccg gacccctgag gtcacatgcg tggtggtgga cgtgagccac    720
gaagaccctg aggtcaagtt caactggtac gtggacggcg tggaggtgca taatgccaag    780
acaaagccgc gggaggagca gtacaacagc acgtaccgtg tggtcagcgt cctcaccgtc    840
ctgcaccagg actggctgaa tggcaaggag tacaagtgcg ccgtctccaa caaagccctc    900
ccagcctcca tcgagaaaac catctccaaa gccaagggc agccccgaga ccacaggtg      960 tacaccctgc cccatcccg ggatgagctg accaagaacc aggtcagcct gacctgcctg    1020
gtcaaaggct tctatcccag cgacatcgcc gtggagtggg agagcaatgg gcagccggag   1080
aacaactaca agaccacgcc tcccgtgctg gactccgacg gctccttctt cctctacagc   1140
aagctcaccg tggacaagag caggtggcag caggggaacg tcttctcatg ctccgtgatg   1200
catgaggctc tgcacaacca ctacacgcag aagagcctct ccctgtctcc gggtaaatga   1260
```

<210> SEQ ID NO 53
<211> LENGTH: 1263
<212> TYPE: DNA
<213> ORGANISM: Artificial
<220> FEATURE:
<223> OTHER INFORMATION: DNA encoding fusion protein

<400> SEQUENCE: 53

```
atgcggcccc gcagcgccct gccccgcctg ctgctgccgc tgctgctgct gccgccgcc      60 gggccggccc agttccacgg ggagaagggc atctccatcc ggaccacgg cttctgccag    120 cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc accgtgtgc     300 accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg ggcaccccg     540 ggtggcccgg gcggcggcgg cgccgagcct aggtcttcag acaaaactca catgccca      600 ccgtgcccag cacctgaagc cgagggggcc ccgtcagtct tcctcttccc cccaaaaccc    660
aaggacaccc tcatgatctc ccggacccct gaggtcacat gcgtggtggt ggacgtgagc    720
cacgaagacc ctgaggtcaa gttcaactgg tacgtggacg gcgtggaggt gcataatgcc    780
aagacaaagc cgcgggagga gcagtacaac agcacgtacc gtgtggtcag cgtcctcacc    840
gtcctgcacc aggactggct gaatggcaag gagtacaagt gcgccgtctc caacaaagcc    900
ctcccagcct ccatcgagaa aaccatctcc aaagccaaag gcagccccg agaaccacag    960 gtgtacaccc tgccccatc cgggatgag ctgaccaaga accaggtcag cctgacctgc    1020
ctggtcaaag gcttctatcc cagcgacatc gccgtggagt gggagagcaa tgggcagccg   1080
gagaacaact acaagaccac gcctcccgtg ctggactccg acggctcctt cttcctctac   1140
```

| | |
|---|---|
| agcaagctca ccgtggacaa gagcaggtgg cagcagggga acgtcttctc atgctccgtg | 1200 |
| atgcatgagg ctctgcacaa ccactacacg cagaagagcc tctccctgtc tccgggtaaa | 1260 |
| tga | 1263 |

<210> SEQ ID NO 54
<211> LENGTH: 1266
<212> TYPE: DNA
<213> ORGANISM: Artificial
<220> FEATURE:
<223> OTHER INFORMATION: DNA encoding fusion protein

<400> SEQUENCE: 54

| | |
|---|---|
| atgcggcccc gcagcgccct gccccgcctg ctgctgccgc tgctgctgct gcccgccgcc | 60 |
| gggccggccc agttccacgg ggagaagggc atctccatcc ggaccacgg cttctgccag | 120 |
| cccatctcca tcccgctgtg cacggacatc gcctacaacc agaccatcat gcccaacctt | 180 |
| ctgggccaca cgaaccagga ggacgcaggc ctagaggtgc accagttcta tccgctggtg | 240 |
| aaggtgcagt gctcgcccga actgcgcttc ttcctgtgct ccatgtacgc accgtgtgc | 300 |
| accgtgctgg aacaggccat cccgccgtgc cgctctatct gtgagcgcgc gcgccagggc | 360 |
| tgcgaagccc tcatgaacaa gttcggtttt cagtggcccg agcgcctgcg ctgcgagcac | 420 |
| ttcccgcgcc acggcgccga gcagatctgc gtcggccaga accactccga ggacggagct | 480 |
| cccgcgctac tcaccaccgc gccgccgccg ggactgcagc cgggtgccgg ggcaccccg | 540 |
| ggtggcccgg cgcggcggcg cgctgccgag cctaggtctt cagacaaaac tcacacatgc | 600 |
| ccaccgtgcc cagcacctga gccgaggggg gcccgtcag tcttcctctt ccccccaaaa | 660 |
| cccaaggaca ccctcatgat ctcccggacc cctgaggtca catgcgtggt ggtggacgtg | 720 |
| agccacgaag accctgaggt caagttcaac tggtacgtgg acggcgtgga ggtgcataat | 780 |
| gccaagacaa agccgcggga ggagcagtac aacagcacgt accgtgtggt cagcgtcctc | 840 |
| accgtcctgc accaggactg gctgaatggc aaggagtaca agtgcgccgt ctccaacaaa | 900 |
| gccctcccag cctccatcga aaaaccatc tccaaagcca agggcagcc ccgagaacca | 960 |
| caggtgtaca ccctgccccc atcccgggat gagctgacca agaaccaggt cagcctgacc | 1020 |
| tgcctggtca aaggcttcta tcccagcgac atcgccgtgg agtgggagag caatgggcag | 1080 |
| ccggagaaca actacaagac cacgcctccc gtgctggact ccgacggctc cttcttcctc | 1140 |
| tacagcaagc tcaccgtgga caagagcagg tggcagcagg ggaacgtctt ctcatgctcc | 1200 |
| gtgatgcatg aggctctgca caaccactac acgcagaaga gcctctccct gtctccgggt | 1260 |
| aaatga | 1266 |

<210> SEQ ID NO 55
<211> LENGTH: 1269
<212> TYPE: DNA
<213> ORGANISM: Artificial
<220> FEATURE:
<223> OTHER INFORMATION: DNA encoding fusion protein

<400> SEQUENCE: 55

| | |
|---|---|
| atgcggcccc gcagcgccct gccccgcctg ctgctgccgc tgctgctgct gcccgccgcc | 60 |
| gggccggccc agttccacgg ggagaagggc atctccatcc ggaccacgg cttctgccag | 120 |
| cccatctcca tcccgctgtg cacggacatc gcctacaacc agaccatcat gcccaacctt | 180 |
| ctgggccaca cgaaccagga ggacgcaggc ctagaggtgc accagttcta tccgctggtg | 240 |

-continued

| | |
|---|---|
| aaggtgcagt gctcgcccga actgcgcttc ttcctgtgct ccatgtacgc accgtgtgc | 300 |
| accgtgctgg aacaggccat cccgccgtgc cgctctatct gtgagcgcgc gcgccagggc | 360 |
| tgcgaagccc tcatgaacaa gttcggtttt cagtggcccg agcgcctgcg ctgcgagcac | 420 |
| ttcccgcgcc acggcgccga gcagatctgc gtcggccaga accactccga ggacggagct | 480 |
| cccgcgctac tcaccaccgc gccgccgccg ggactgcagc cgggtgccgg gggcaccccg | 540 |
| ggtggcccgg gcggcggcgg cgctcccgcc gagcctaggc cttcagacaa aactcacaca | 600 |
| tgcccaccgt gcccagcacc tgaagccgag ggggcccgt cagtcttcct cttccccca | 660 |
| aaacccaagg acaccctcat gatctcccgg acccctgagg tcacatgcgt ggtggtggac | 720 |
| gtgagccacg aagaccctga ggtcaagttc aactggtacg tggacggcgt ggaggtgcat | 780 |
| aatgccaaga caaagccgcg ggaggagcag tacaacagca cgtaccgtgt ggtcagcgtc | 840 |
| ctcaccgtcc tgcaccagga ctggctgaat ggcaaggagt acaagtgcgc cgtctccaac | 900 |
| aaagcccctcc cagcctccat cgagaaaacc atctccaaag ccaagggca gccccgagaa | 960 |
| ccacaggtgt acaccctgcc cccatcccgg gatgagctga ccaagaacca ggtcagcctg | 1020 |
| acctgcctgg tcaaaggctt ctatcccagc gacatcgccg tggagtggga gagcaatggg | 1080 |
| cagccggaga acaactacaa gaccacgcct cccgtgctgg actccgacgg ctccttcttc | 1140 |
| ctctacagca agctcaccgt ggacaagagc aggtggcagc aggggaacgt cttctcatgc | 1200 |
| tccgtgatgc atgaggctct gcacaaccac tacacgcaga gagcctctc cctgtctccg | 1260 |
| ggtaaatga | 1269 |

<210> SEQ ID NO 56
<211> LENGTH: 1272
<212> TYPE: DNA
<213> ORGANISM: Artificial
<220> FEATURE:
<223> OTHER INFORMATION: DNA encoding protein

<400> SEQUENCE: 56

| | |
|---|---|
| atgcggcccc gcagcgccct gccccgcctg ctgctgccgc tgctgctgct gccgccgcc | 60 |
| gggccggccc agttccacgg ggagaagggc atctccatcc ggaccacgg cttctgccag | 120 |
| cccatctcca tcccgctgtg cacggacatc gcctacaacc agaccatcat gcccaacctt | 180 |
| ctgggccaca cgaaccagga ggacgcaggc ctagaggtgc accagttcta tccgctggtg | 240 |
| aaggtgcagt gctcgcccga actgcgcttc ttcctgtgct ccatgtacgc accgtgtgc | 300 |
| accgtgctgg aacaggccat cccgccgtgc cgctctatct gtgagcgcgc gcgccagggc | 360 |
| tgcgaagccc tcatgaacaa gttcggtttt cagtggcccg agcgcctgcg ctgcgagcac | 420 |
| ttcccgcgcc acggcgccga gcagatctgc gtcggccaga accactccga ggacggagct | 480 |
| cccgcgctac tcaccaccgc gccgccgccg ggactgcagc cgggtgccgg gggcaccccg | 540 |
| ggtggcccgg gcggcggcgg cgctccccgc gccgagccta gtcttcaga caaaactcac | 600 |
| acatgcccac cgtgcccagc acctgaagcc gagggggccc gtcagtctt cctcttcccc | 660 |
| ccaaaaccca aggacaccct catgatctcc cggacccctg aggtcacatg cgtggtggtg | 720 |
| gacgtgagcc acgaagaccc tgaggtcaag ttcaactggt acgtgacgg cgtggaggtg | 780 |
| cataatgcca agacaaagcc gcgggaggag cagtacaaca gcacgtaccg tgtggtcagc | 840 |
| gtcctcaccg tcctgcacca ggactggctg aatggcaagg agtacaagtg cgccgtctcc | 900 |
| aacaaagccc tcccagcctc catcgagaaa accatctccaa agccaaagg gcagcccga | 960 |
| gaaccacagg tgtacaccct gcccccatcc cgggatgagc tgaccaagaa ccaggtcagc | 1020 |

| | |
|---|---:|
| ctgacctgcc tggtcaaagg cttctatccc agcgacatcg ccgtggagtg ggagagcaat | 1080 |
| gggcagccgg agaacaacta caagaccacg cctcccgtgc tggactccga cggctccttc | 1140 |
| ttcctctaca gcaagctcac cgtggacaag agcaggtggc agcagggaa cgtcttctca | 1200 |
| tgctccgtga tgcatgaggc tctgcacaac cactacacgc agaagagcct ctccctgtct | 1260 |
| ccgggtaaat ga | 1272 |

<210> SEQ ID NO 57
<211> LENGTH: 1275
<212> TYPE: DNA
<213> ORGANISM: Artificial
<220> FEATURE:
<223> OTHER INFORMATION: DNA encoding protein

<400> SEQUENCE: 57

| | |
|---|---:|
| atgcggcccc gcagcgccct gccccgcctg ctgctgccgc tgctgctgct gccgccgcc | 60 |
| gggccggccc agttccacgg ggagaagggc atctccatcc cggaccacgg cttctgccag | 120 |
| cccatctcca tcccgctgtg cacggacatc gcctacaacc agaccatcat gcccaacctt | 180 |
| ctgggccaca cgaaccagga ggacgcaggc ctagaggtgc accagttcta tccgctggtg | 240 |
| aaggtgcagt gctcgcccga actgcgcttc ttcctgtgct ccatgtacgc accgtgtgc | 300 |
| accgtgctgg aacaggccat cccgccgtgc cgctctatct gtgagcgcgc gcgccagggc | 360 |
| tgcgaagccc tcatgaacaa gttcggtttt cagtggcccg agcgcctgcg ctgcgagcac | 420 |
| ttcccgcgcc acggcgccga gcagatctgc gtcggccaga accactccga ggacggagct | 480 |
| cccgcgctac tcaccaccgc gccgccgccg ggactgcagc cgggtgccgg ggcaccccg | 540 |
| ggtggcccgg gcggcggcgg cgctccccg cgcgccgagc ctaggtcttc agacaaaact | 600 |
| cacacatgcc caccgtgccc agcacctgaa gcgaggggg cccgtcagt cttcctcttc | 660 |
| cccccaaaac ccaaggacac cctcatgatc tcccggaccc ctgaggtcac atgcgtggtg | 720 |
| gtggacgtga gccacgaaga ccctgaggtc aagttcaact ggtacgtgga cggcgtggag | 780 |
| gtgcataatg ccaagacaaa gccgcgggag gagcagtaca acagcacgta ccgtgtggtc | 840 |
| agcgtcctca ccgtcctgca ccaggactgg ctgaatggca aggagtacaa gtgcgccgtc | 900 |
| tccaacaaag ccctcccagc ctccatcgag aaaaccatct ccaaagccaa agggcagccc | 960 |
| cgagaaccac aggtgtacac cctgccccca tcccgggatg agctgaccaa gaaccaggtc | 1020 |
| agcctgacct gcctggtcaa aggcttctat cccagcgaca tcgccgtgga gtgggagagc | 1080 |
| aatgggcagc cggagaacaa ctacaagacc acgcctcccg tgctggactc cgacggctcc | 1140 |
| ttcttcctct acagcaagct caccgtggac aagagcaggt ggcagcaggg gaacgtcttc | 1200 |
| tcatgctccg tgatgcatga ggctctgcac aaccactaca cgcagaagag cctctccctg | 1260 |
| tctccgggta aatga | 1275 |

<210> SEQ ID NO 58
<211> LENGTH: 1278
<212> TYPE: DNA
<213> ORGANISM: Artificial
<220> FEATURE:
<223> OTHER INFORMATION: DNA encoding fusion protein

<400> SEQUENCE: 58

| | |
|---|---:|
| atgcggcccc gcagcgccct gccccgcctg ctgctgccgc tgctgctgct gccgccgcc | 60 |
| gggccggccc agttccacgg ggagaagggc atctccatcc cggaccacgg cttctgccag | 120 |

```
cccatctcca tcccgctgtg cacggacatc gcctacaacc agaccatcat gcccaacctt      180
ctgggccaca cgaaccagga ggacgcaggc ctagaggtgc accagttcta tccgctggtg      240
aaggtgcagt gctcgcccga actgcgcttc ttcctgtgct ccatgtacgc accgtgtgc       300 accgtgctgg aacaggccat cccgccgtgc cgctctatct gtgagcgcgc gcgccagggc      360
tgcgaagccc tcatgaacaa gttcggtttt cagtggcccg agcgcctgcg ctgcgagcac      420
ttcccgcgcc acggcgccga gcagatctgc gtcggccaga accactccga ggacggagct      480
cccgcgctac tcaccaccgc gccgccgccg ggactgcagc cgggtgccgg gggcaccccg      540
ggtggcccgg gcggcggcgg cgctcccccg cgctacgccg agcctaggtc ttcagacaaa      600
actcacacat gcccaccgtg cccagcacct gaagccgagg gggcccccgtc agtcttcctc     660 ttcccccaa acccaaggac accctcatg atctcccgga cccctgaggt cacatgcgtg        720
gtggtggacg tgagccacga agaccctgag gtcaagttca actggtacgt ggacggcgtg     780
gaggtgcata atgccaagac aaagccgcgg gaggagcagt acaacagcac gtaccgtgtg     840
gtcagcgtcc tcaccgtcct gcaccaggac tggctgaatg gcaaggagta caagtgcgcc    900
gtctccaaca aagccctccc agcctccatc gagaaaacca tctccaaagc caaagggcag    960
ccccgagaac acaggtgta cccctgccc ccatcccggg atgagctgac caagaaccag       1020
gtcagcctga cctgcctggt caaaggcttc tatcccagcg acatcgccgt ggagtgggag    1080
agcaatgggc agccggagaa caactacaag accacgcctc ccgtgctgga ctccgacggc    1140
tccttcttcc tctacagcaa gctcaccgtg gacaagagca ggtggcagca ggggaacgtc    1200
ttctcatgct ccgtgatgca tgaggctctg cacaaccact acacgcagaa gagcctctcc    1260
ctgtctccgg gtaaatga                                                   1278
```

<210> SEQ ID NO 59
<211> LENGTH: 1281
<212> TYPE: DNA
<213> ORGANISM: Artificial
<220> FEATURE:
<223> OTHER INFORMATION: DNA encoding fusion protein

<400> SEQUENCE: 59

```
atgcggcccc gcagcgccct gccccgcctg ctgctgccgc tgctgctgct gcccgccgcc      60
gggccggccc agttccacgg ggagaagggc atctccatcc cggaccacgg cttctgccag     120
cccatctcca tcccgctgtg cacggacatc gcctacaacc agaccatcat gcccaacctt     180
ctgggccaca cgaaccagga ggacgcaggc ctagaggtgc accagttcta tccgctggtg     240
aaggtgcagt gctcgcccga actgcgcttc ttcctgtgct ccatgtacgc accgtgtgc      300 accgtgctgg aacaggccat cccgccgtgc cgctctatct gtgagcgcgc gcgccagggc     360
tgcgaagccc tcatgaacaa gttcggtttt cagtggcccg agcgcctgcg ctgcgagcac     420
ttcccgcgcc acggcgccga gcagatctgc gtcggccaga accactccga ggacggagct     480
cccgcgctac tcaccaccgc gccgccgccg ggactgcagc cgggtgccgg gggcaccccg     540
ggtggcccgg gcggcggcgg cgctcccccg cgctacgccg ccgagcctag gtcttcagac    600
aaaactcaca catgcccacc gtgcccagca cctgaagccg agggggcccc gtcagtcttc    660
ctcttccccc caaaacccaa ggacaccctc atgatctccc ggacccctga ggtcacatgc    720
gtggtggtgg acgtgagcca cgaagaccct gaggtcaagt tcaactggta cgtggacggc    780
gtggaggtgc ataatgccaa gacaaagccg cgggaggagc agtacaacag cacgtaccgt    840
gtggtcagcg tcctcaccgt cctgcaccag gactggctga atggcaagga gtacaagtgc    900
```

```
gccgtctcca acaaagccct cccagcctcc atcgagaaaa ccatctccaa agccaaaggg      960
cagccccgag aaccacaggt gtacaccctg cccccatccc gggatgagct gaccaagaac     1020
caggtcagcc tgacctgcct ggtcaaaggc ttctatccca gcgacatcgc cgtggagtgg     1080
gagagcaatg ggcagccgga gaacaactac aagaccacgc ctcccgtgct ggactccgac     1140
ggctccttct tcctctacag caagctcacc gtggacaaga gcaggtggca gcagggggaac   1200 gtcttctcat gctccgtgat gcatgaggct ctgcacaacc actacacgca gaagagcctc     1260
tccctgtctc cgggtaaatg a                                               1281

<210> SEQ ID NO 60
<211> LENGTH: 1284
<212> TYPE: DNA
<213> ORGANISM: Artificial
<220> FEATURE:
<223> OTHER INFORMATION: DNA encoding fusion protein

<400> SEQUENCE: 60
atgcggcccc gcagcgccct gccccgcctg ctgctgccgc tgctgctgct gcccgccgcc       60
gggccggccc agttccacgg ggagaagggc atctccatcc cggaccacgg cttctgccag      120
cccatctcca tcccgctgtg cacggacatc gcctacaacc agaccatcat gcccaacctt      180
ctgggccaca cgaaccagga ggacgcaggc ctagaggtgc accagttcta tccgctggtg      240
aaggtgcagt gctcgcccga actgcgcttc ttcctgtgct ccatgtacgc accgtgtgc       300 accgtgctgg aacaggccat cccgccgtgc cgctctatct gtgagcgcgc gcgccagggc      360
tgcgaagccc tcatgaacaa gttcggtttt cagtggcccg agcgcctgcg ctgcgagcac      420
ttcccgcgcc acggcgccga gcagatctgc gtcggccaga accactccga ggacggagct      480
cccgcgctac tcaccaccgc gccgccgccg ggactgcagc cgggtgccgg ggcacccccg      540
ggtggcccgg gcggcggcgg cgctcccccg cgctacgcca cggccgagcc taggtcttca      600
gacaaaactc acacatgccc accgtgccca gcacctgaag ccgaggggggc ccgtcagtc     660 ttcctcttcc ccccaaaacc caaggacacc ctcatgatct cccggacccc tgaggtcaca      720
tgcgtggtgg tggacgtgag ccacgaagac cctgaggtca agttcaactg gtacgtggac      780
ggcgtggagg tgcataatgc caagacaaag ccgcgggagg agcagtacaa cagcacgtac      840
cgtgtggtca gcgtcctcac cgtcctgcac caggactggc tgaatggcaa ggagtacaag      900
tgcgccgtct ccaacaaagc cctcccagcc tccatcgaga aaaccatctc caaagccaaa      960
gggcagcccc gagaaccaca ggtgtacacc ctgcccccat cccgggatga gctgaccaag     1020
aaccaggtca gcctgacctg cctggtcaaa ggcttctatc cagcgacat cgccgtggag     1080 tgggagagca atgggcagcc ggagaacaac tacaagacca cgcctcccgt gctggactcc     1140
gacggctcct tcttcctcta cagcaagctc accgtggaca agagcaggtg gcagcagggg     1200
aacgtcttct catgctccgt gatgcatgag gctctgcaca accactacac gcagaagagc     1260
ctctccctgt ctccgggtaa atga                                            1284

<210> SEQ ID NO 61
<211> LENGTH: 1287
<212> TYPE: DNA
<213> ORGANISM: Artificial
<220> FEATURE:
<223> OTHER INFORMATION: DNA encoding fusion protein

<400> SEQUENCE: 61
```

```
atgcggcccc gcagcgccct gccccgcctg ctgctgccgc tgctgctgct gcccgccgcc    60
gggccggccc agttccacgg ggagaagggc atctccatcc cggaccacgg cttctgccag   120
cccatctcca tcccgctgtg cacggacatc gcctacaacc agaccatcat gcccaacctt   180
ctgggccaca cgaaccagga ggacgcaggc ctagaggtgc accagttcta tccgctggtg   240
aaggtgcagt gctcgcccga actgcgcttc ttcctgtgct ccatgtacgc accgtgtgc    300
accgtgctgg aacaggccat cccgccgtgc cgctctatct gtgagcgcgc gcgccagggc   360
tgcgaagccc tcatgaacaa gttcggtttt cagtggcccg agcgcctgcg ctgcgagcac   420
ttcccgcgcc acggcgccga gcagatctgc gtcggccaga accactccga ggacggagct   480
cccgcgctac tcaccaccgc gccgccgccg ggactgcagc cgggtgccgg ggcacccccg   540
ggtggcccgg gcggcggcgg cgctcccccg cgctacgcca cgctggccga gcctaggtct   600
tcagacaaaa ctcacacatg cccaccgtgc ccagcacctg aagccgaggg ggccccgtca   660
gtcttcctct ccccccaaa acccaaggac accctcatga tctcccggac ccctgaggtc   720
acatgcgtgg tggtggacgt gagccacgaa gaccctgagg tcaagttcaa ctggtacgtg   780
gacggcgtgg aggtgcataa tgccaagaca aagccgcggg aggagcagta caacagcacg   840
taccgtgtgg tcagcgtcct caccgtcctg caccaggact ggctgaatgg caaggagtac   900
aagtgcgccg tctccaacaa agcccctccca gcctccatcg agaaaaccat ctccaaagcc   960
aaagggcagc cccgagaacc acaggtgtac accctgcccc catcccggga tgagctgacc  1020
aagaaccagg tcagcctgac ctgcctggtc aaaggcttct atcccagcga catcgccgtg  1080
gagtgggaga gcaatgggca gccggagaac aactacaaga ccacgcctcc cgtgctggac  1140
tccgacggct ccttcttcct ctacagcaag ctcaccgtgg acaagagcag gtggcagcag  1200
gggaacgtct tctcatgctc cgtgatgcat gaggctctgc acaaccacta cacgcagaag  1260
agcctctccc tgtctccggg taaatga                                       1287

<210> SEQ ID NO 62
<211> LENGTH: 1290
<212> TYPE: DNA
<213> ORGANISM: Artificial
<220> FEATURE:
<223> OTHER INFORMATION: DNA encoding fusion protein

<400> SEQUENCE: 62
atgcggcccc gcagcgccct gccccgcctg ctgctgccgc tgctgctgct gcccgccgcc    60
gggccggccc agttccacgg ggagaagggc atctccatcc cggaccacgg cttctgccag   120
cccatctcca tcccgctgtg cacggacatc gcctacaacc agaccatcat gcccaacctt   180
ctgggccaca cgaaccagga ggacgcaggc ctagaggtgc accagttcta tccgctggtg   240
aaggtgcagt gctcgcccga actgcgcttc ttcctgtgct ccatgtacgc accgtgtgc    300
accgtgctgg aacaggccat cccgccgtgc cgctctatct gtgagcgcgc gcgccagggc   360
tgcgaagccc tcatgaacaa gttcggtttt cagtggcccg agcgcctgcg ctgcgagcac   420
ttcccgcgcc acggcgccga gcagatctgc gtcggccaga accactccga ggacggagct   480
cccgcgctac tcaccaccgc gccgccgccg ggactgcagc cgggtgccgg ggcacccccg   540
ggtggcccgg gcggcggcgg cgctcccccg cgctacgcca cgctggaggc cgagcctagg   600
tcttcagaca aaactcacac atgcccaccg tgcccagcac ctgaagccga gggggccccg   660
tcagtcttcc tcttcccccc aaaacccaag gacaccctca tgatctcccg gacccctgag   720
gtcacatgcg tggtggtgga cgtgagccac gaagaccctg aggtcaagtt caactggtac   780
```

```
gtggacggcg tggaggtgca taatgccaag acaaagccgc gggaggagca gtacaacagc    840
acgtaccgtg tggtcagcgt cctcaccgtc ctgcaccagg actggctgaa tgcaaggag    900 tacaagtgcg ccgtctccaa caaagccctc ccagcctcca tcgagaaaac catctccaaa    960 gccaagggc agccccgaga accacaggtg tacaccctgc ccccatcccg ggatgagctg    1020
accaagaacc aggtcagcct gacctgcctg gtcaaaggct ctatcccag cgacatcgcc    1080 gtggagtggg agagcaatgg gcagccggag aacaactaca agaccacgcc tcccgtgctg    1140
gactccgacg gctccttctt cctctacagc aagctcaccg tggacaagag caggtggcag    1200
caggggaacg tcttctcatg ctccgtgatg catgaggctc tgcacaacca ctacacgcag    1260
aagagcctct ccctgtctcc gggtaaatga                                    1290
```

<210> SEQ ID NO 63
<211> LENGTH: 1293
<212> TYPE: DNA
<213> ORGANISM: Artificial
<220> FEATURE:
<223> OTHER INFORMATION: DNA encoding fusion protein

<400> SEQUENCE: 63

```
atgcggcccc gcagcgccct gccccgcctg ctgctgccgc tgctgctgct gcccgccgcc    60
gggccggccc agttccacgg ggagaagggc atctccatcc ggaccacgg cttctgccag    120 cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc accgtgtgc    300 accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg ggcaccccg    540 ggtggcccgg cggcggcgg cgctcccccg cgctacgcca cgctggagca cgccgagcct    600
aggtcttcag acaaaactca cacatgccca ccgtgcccag cacctgaagc cgagggggcc    660
ccgtcagtct tcctcttccc cccaaaaccc aaggacaccc tcatgatctc ccggacccct    720
gaggtcacat gcgtggtggt ggacgtgagc cacgaagacc ctgaggtcaa gttcaactgg    780
tacgtggacg gcgtggaggt gcataatgcc aagacaaagc cgcggggagga gcagtacaac    840 agcacgtacc gtgtggtcag cgtcctcacc gtcctgcacc aggactggct gaatggcaag    900
gagtacaagt gcgccgtctc caacaaagcc ctcccagcct ccatcgagaa aaccatctcc    960
aaagccaaag ggcagccccg agaaccacag gtgtacaccc tgcccccatc ccgggatgag    1020
ctgaccaaga accaggtcag cctgacctgc ctggtcaaag gcttctatcc cagcgacatc    1080
gccgtggagt gggagagcaa tgggcagccg gagaacaact acaagaccac gcctcccgtg    1140
ctggactccg acggctcctt cttcctctac agcaagctca ccgtggacaa gagcaggtgg    1200
cagcagggga cgtcttctc atgctccgtg atgcatgagg ctctgcacaa ccactacacg    1260
cagaagagcc tctccctgtc tccgggtaaa tga                                1293
```

<210> SEQ ID NO 64
<211> LENGTH: 1296
<212> TYPE: DNA
<213> ORGANISM: Artificial
<220> FEATURE:

<223> OTHER INFORMATION: DNA encoding fusion protein

<400> SEQUENCE: 64

```
atgcggcccc gcagcgccct gccccgcctg ctgctgccgc tgctgctgct gcccgccgcc      60
gggccggccc agttccacgg ggagaagggc atctccatcc cggaccacgg cttctgccag     120
cccatctcca tcccgctgtg cacggacatc gcctacaacc agaccatcat gcccaacctt     180
ctgggccaca cgaaccagga ggacgcaggc ctagaggtgc accagttcta tccgctggtg     240
aaggtgcagt gctcgcccga actgcgcttc ttcctgtgct ccatgtacgc accgtgtgc      300
accgtgctgg aacaggccat cccgccgtgc cgctctatct gtgagcgcgc gcgccagggc     360
tgcgaagccc tcatgaacaa gttcggtttt cagtggcccg agcgcctgcg ctgcgagcac     420
ttcccgcgcc acggcgccga gcagatctgc gtcggccaga accactccga ggacggagct     480
cccgcgctac tcaccaccgc gccgccgccg ggactgcagc cgggtgccgg ggcaccccg      540
ggtggcccgg gcggcggcgg cgctcccccg cgctacgcca cgctggagca cccgccgag      600
cctaggtctt cagacaaaac tcacacatgc ccaccgtgcc cagcacctga gccgagggg      660
gccccgtcag tcttcctctt ccccccaaaa cccaaggaca ccctcatgat ctcccggacc     720
cctgaggtca catgcgtggt ggtggacgtg agccacgaag accctgaggt caagttcaac     780
tggtacgtgg acggcgtgga ggtgcataat gccaagacaa agccgcggga ggagcagtac     840
aacagcacgt accgtgtggt cagcgtcctc accgtcctgc accaggactg gctgaatggc     900
aaggagtaca agtgcgccgt ctccaacaaa gccctcccag cctccatcga gaaaaccatc     960
tccaaagcca agggcagccc cgagaaccca caggtgtaca ccctgccccc atcccgggat    1020
gagctgacca agaaccaggt cagcctgacc tgcctggtca aaggcttcta tcccagcgac    1080
atcgccgtgg agtgggagag caatgggcag ccggagaaca actacaagac cacgcctccc    1140
gtgctggact ccgacggctc cttcttcctc tacagcaagc tcaccgtgga caagagcagg    1200
tggcagcagg ggaacgtctt ctcatgctcc gtgatgcatg aggctctgca caaccactac    1260
acgcagaaga gcctctccct gtctccgggt aaatga                              1296
```

<210> SEQ ID NO 65
<211> LENGTH: 1305
<212> TYPE: DNA
<213> ORGANISM: Artificial
<220> FEATURE:
<223> OTHER INFORMATION: DNA encoding fusion protein

<400> SEQUENCE: 65

```
atgcggcccc gcagcgccct gccccgcctg ctgctgccgc tgctgctgct gcccgccgcc      60
gggccggccc agttccacgg ggagaagggc atctccatcc cggaccacgg cttctgccag     120
cccatctcca tcccgctgtg cacggacatc gcctacaacc agaccatcat gcccaacctt     180
ctgggccaca cgaaccagga ggacgcaggc ctagaggtgc accagttcta tccgctggtg     240
aaggtgcagt gctcgcccga actgcgcttc ttcctgtgct ccatgtacgc accgtgtgc      300
accgtgctgg aacaggccat cccgccgtgc cgctctatct gtgagcgcgc gcgccagggc     360
tgcgaagccc tcatgaacaa gttcggtttt cagtggcccg agcgcctgcg ctgcgagcac     420
ttcccgcgcc acggcgccga gcagatctgc gtcggccaga accactccga ggacggagct     480
cccgcgctac tcaccaccgc gccgccgccg ggactgcagc cgggtgccgg ggcaccccg      540
ggtggcccgg gcggcggcgg cgctcccccg cgctacgcca cgctggagca cccccttccac    600
tgcgccgagc ctaggtcttc agacaaaact cacacatgcc caccgtgccc agcacctgaa     660
```

```
gccgagggggg ccccgtcagt cttcctcttc cccccaaaac ccaaggacac cctcatgatc      720
tcccggaccc ctgaggtcac atgcgtggtg gtggacgtga gccacgaaga ccctgaggtc      780
aagttcaact ggtacgtgga cggcgtggag gtgcataatg ccaagacaaa gccgcgggag      840
gagcagtaca acagcacgta ccgtgtggtc agcgtcctca ccgtcctgca ccaggactgg      900
ctgaatggca aggagtacaa gtgcgccgtc tccaacaaag ccctcccagc tccatcgag       960 aaaaccatct ccaaagccaa agggcagccc cgagaaccac aggtgtacac cctgccccca     1020
tcccgggatg agctgaccaa gaaccaggtc agcctgacct gcctggtcaa aggcttctat     1080
cccagcgaca tcgccgtgga gtgggagagc aatgggcagc cggagaacaa ctacaagacc     1140
acgcctcccg tgctggactc cgacggctcc ttcttcctct acagcaagct caccgtggac     1200
aagagcaggt ggcagcaggg gaacgtcttc tcatgctccg tgatgcatga ggctctgcac     1260
aaccactaca cgcagaagag cctctccctg tctccgggta aatga                     1305
```

<210> SEQ ID NO 66
<211> LENGTH: 1323
<212> TYPE: DNA
<213> ORGANISM: Artificial
<220> FEATURE:
<223> OTHER INFORMATION: DNA encoding fusion protein

<400> SEQUENCE: 66

```
atgcggcccc gcagcgccct gccccgcctg ctgctgccgc tgctgctgct gccccgccgcc      60 gggccggccc agttccacgg ggagaagggc atctccatcc cggaccacgg cttctgccag     120
cccatctcca tcccgctgtg cacggacatc gcctacaacc agaccatcat gcccaacctt     180
ctgggccaca cgaaccagga ggacgcaggc ctagaggtgc accagttcta tccgctggtg     240
aaggtgcagt gctcgcccga actgcgcttc ttcctgtgct ccatgtacgc acccgtgtgc     300
accgtgctgg aacaggccat cccgccgtgc cgctctatct gtgagcgcgc gcgccagggc     360
tgcgaagccc tcatgaacaa gttcggtttt cagtggcccg agcgcctgcg ctgcgagcac     420
ttcccgcgcc acggcgccga gcagatctgc gtcggccaga accactccga ggacggagct     480
cccgcgctac tcaccaccgc gccgccgccg ggactgcagc cgggtgccgg gggcacccccg     540 ggtggcccgg gcggcggcgg cgctccccccg cgctacgcca cgctggagca ccccttccac     600
tgcccgcgcg tcctcaaggt ggccgagcct aggtcttcag acaaaactca cacatgccca     660
ccgtgcccag cacctgaagc cgagggggcc ccgtcagtct tcctcttccc cccaaaaccc     720
aaggacaccc tcatgatctc ccggacccct gaggtcacat gcgtggtggt ggacgtgagc     780
cacgaagacc ctgaggtcaa gttcaactgg tacgtggacg gcgtggaggt gcataatgcc     840
aagacaaagc cgcgggagga gcagtacaac agcacgtacc gtgtggtcag cgtcctcacc     900
gtcctgcacc aggactggct gaatggcaag gagtacaagt gcgccgtctc caacaaagcc     960
ctcccagcct ccatcgagaa aaccatctcc aaagccaaag ggcagccccg agaaccacag    1020
gtgtacaccc tgcccccatc ccgggatgag ctgaccaaga accaggtcag cctgacctgc    1080
ctggtcaaag gcttctatcc cagcgacatc gccgtggagt gggagagcaa tgggcagccg    1140
gagaacaact acaagaccac gcctcccgtg ctggactccg acggctcctt cttcctctac    1200
agcaagctca ccgtggacaa gagcaggtgg cagcagggga acgtcttctc atgctccgtg    1260
atgcatgagg ctctgcacaa ccactacacg cagaagagcc tctccctgtc tccgggtaaa    1320
tga                                                                  1323
```

<210> SEQ ID NO 67
<211> LENGTH: 1341
<212> TYPE: DNA
<213> ORGANISM: Artificial
<220> FEATURE:
<223> OTHER INFORMATION: DNA encoding fusion protein

<400> SEQUENCE: 67

| | | | | | |
|---|---|---|---|---|---|
| atgcggcccc | gcagcgccct | gccccgcctg | ctgctgccgc | tgctgctgct | gcccgccgcc | 60 |
| gggccggccc | agttccacgg | ggagaagggc | atctccatcc | cggaccacgg | cttctgccag | 120 |
| cccatctcca | tcccgctgtg | cacggacatc | gcctacaacc | agaccatcat | gcccaacctt | 180 |
| ctgggccaca | cgaaccagga | ggacgcaggc | ctagaggtgc | accagttcta | tccgctggtg | 240 |
| aaggtgcagt | gctcgcccga | actgcgcttc | ttcctgtgct | ccatgtacgc | acccgtgtgc | 300 |
| accgtgctgg | aacaggccat | cccgccgtgc | cgctctatct | gtgagcgcgc | gcgccagggc | 360 |
| tgcgaagccc | tcatgaacaa | gttcggtttt | cagtggcccg | agcgcctgcg | ctgcgagcac | 420 |
| ttcccgcgcc | acggcgccga | gcagatctgc | gtcggccaga | ccactccga | ggacggagct | 480 |
| cccgcgctac | tcaccaccgc | gccgccgccg | ggactgcagc | cgggtgccgg | gggcaccccg | 540 |
| ggtggcccgg | gcggcggcgg | cgctcccccg | cgctacgcca | cgctggagca | ccccttccac | 600 |
| tgcccgcgcg | tcctcaaggt | gccatcctat | ctcagctacg | ccgagcctag | gtcttcagac | 660 |
| aaaactcaca | catgcccacc | gtgcccagca | cctgaagccg | aggggcccc | gtcagtcttc | 720 |
| ctcttccccc | caaaacccaa | ggacaccctc | atgatctccc | ggacccctga | ggtcacatgc | 780 |
| gtggtggtgg | acgtgagcca | cgaagaccct | gaggtcaagt | tcaactggta | cgtggacggc | 840 |
| gtggaggtgc | ataatgccaa | gacaaagccg | cgggaggagc | agtacaacag | cacgtaccgt | 900 |
| gtggtcagcg | tcctcaccgt | cctgcaccag | gactggctga | atggcaagga | gtacaagtgc | 960 |
| gccgtctcca | acaaagccct | cccagcctcc | atcgagaaaa | ccatctccaa | agccaaaggg | 1020 |
| cagccccgag | aaccacaggt | gtacaccctg | ccccatccc | gggatgagct | gaccaagaac | 1080 |
| caggtcagcc | tgacctgcct | ggtcaaaggc | ttctatccca | gcgacatcgc | cgtggagtgg | 1140 |
| gagagcaatg | ggcagccgga | gaacaactac | aagaccacgc | ctcccgtgct | ggactccgac | 1200 |
| ggctccttct | tcctctacag | caagctcacc | gtggacaaga | gcaggtggca | gcaggggaac | 1260 |
| gtcttctcat | gctccgtgat | gcatgaggct | ctgcacaacc | actacacgca | gaagagcctc | 1320 |
| tccctgtctc | cgggtaaatg | a | | | | 1341 |

<210> SEQ ID NO 68
<211> LENGTH: 1362
<212> TYPE: DNA
<213> ORGANISM: Artificial
<220> FEATURE:
<223> OTHER INFORMATION: DNA encoding fusion protein

<400> SEQUENCE: 68

| | | | | | |
|---|---|---|---|---|---|
| atgcggcccc | gcagcgccct | gccccgcctg | ctgctgccgc | tgctgctgct | gcccgccgcc | 60 |
| gggccggccc | agttccacgg | ggagaagggc | atctccatcc | cggaccacgg | cttctgccag | 120 |
| cccatctcca | tcccgctgtg | cacggacatc | gcctacaacc | agaccatcat | gcccaacctt | 180 |
| ctgggccaca | cgaaccagga | ggacgcaggc | ctagaggtgc | accagttcta | tccgctggtg | 240 |
| aaggtgcagt | gctcgcccga | actgcgcttc | ttcctgtgct | ccatgtacgc | acccgtgtgc | 300 |
| accgtgctgg | aacaggccat | cccgccgtgc | cgctctatct | gtgagcgcgc | gcgccagggc | 360 |
| tgcgaagccc | tcatgaacaa | gttcggtttt | cagtggcccg | agcgcctgcg | ctgcgagcac | 420 |

```
ttcccgcgcc acggcgccga gcagatctgc gtcggccaga accactccga ggacggagct    480
cccgcgctac tcaccaccgc gccgccgccg ggactgcagc cgggtgccgg gggcaccccg    540
ggtggcccgg cggcggcggc cgctcccccg cgctacgcca cgctggagca ccccttccac    600
tgcccgcgcg tcctcaaggt gccatcctat ctcagctaca agtttctggg cgagcgtgat    660
gccgagccta ggtcttcaga caaaactcac acatgcccac cgtgcccagc acctgaagcc    720
gagggggccc cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg cgccgtctcc aacaaagccc tcccagcctc catcgagaaa   1020
accatctcca aagccaaagg gcagcccgga gaaccacagg tgtacaccct gcccccatcc   1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat ga                     1362
```

<210> SEQ ID NO 69
<211> LENGTH: 1401
<212> TYPE: DNA
<213> ORGANISM: Artificial
<220> FEATURE:
<223> OTHER INFORMATION: DNA encoding fusion protein

<400> SEQUENCE: 69

```
atgcggcccc gcagcgccct gccccgcctg ctgctgccgc tgctgctgct gcccgccgcc     60
gggccggccc agttccacgg ggagaagggc atctccatcc cggaccacgg cttctgccag    120
cccatctcca tcccgctgtg cacggacatc gcctacaacc agaccatcat gcccaacctt    180
ctgggccaca cgaaccagga ggacgcaggc ctagaggtgc accagttcta tccgctggtg    240
aaggtgcagt gctcgcccga actgcgcttc ttcctgtgct ccatgtacgc acccgtgtgc    300
accgtgctgg aacaggccat cccgccgtgc cgctctatct gtgagcgcgc gcgccagggc    360
tgcgaagccc tcatgaacaa gttcggtttt cagtggcccg agcgcctgcg ctgcgagcac    420
ttcccgcgcc acggcgccga gcagatctgc gtcggccaga accactccga ggacggagct    480
cccgcgctac tcaccaccgc gccgccgccg ggactgcagc cgggtgccgg gggcaccccg    540
ggtggcccgg cggcggcggc cgctcccccg cgctacgcca cgctggagca ccccttccac    600
tgcccgcgcg tcctcaaggt gccatcctat ctcagctaca agtttctggg cgagcgtgat    660
tgtgctgcgc cctgcgaacc tgcgcggccc gatggttccg ccgagcctag gtcttcagac    720
aaaactcaca catgcccacc gtgcccagca cctgaagccg aggggccccc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
gccgtctcca acaaagccct cccagcctcc atcgagaaaa ccatctccaa agccaaaggg   1080
```

```
cagccccgag aaccacaggt gtacaccctg cccccatccc gggatgagct gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcagggggaac   1320 gtcttctcat gctccgtgat gcatgaggct ctgcacaacc actacacgca gaagagcctc    1380
tccctgtctc cgggtaaatg a                                              1401

<210> SEQ ID NO 70
<211> LENGTH: 1419
<212> TYPE: DNA
<213> ORGANISM: Artificial
<220> FEATURE:
<223> OTHER INFORMATION: DNA encoding fusion protein

<400> SEQUENCE: 70
atgcggcccc gcagcgccct gccccgcctg ctgctgccgc tgctgctgct gcccgccgcc      60
gggccggccc agttccacgg ggagaagggc atctccatcc cggaccacgg cttctgccag     120
cccatctcca tcccgctgtg cacggacatc gcctacaacc agaccatcat gcccaacctt     180
ctgggccaca cgaaccagga ggacgcaggc ctagaggtgc accagttcta tccgctggtg     240
aaggtgcagt gctcgcccga actgcgcttc ttcctgtgct ccatgtacgc acccgtgtgc     300
accgtgctgg aacaggccat cccgccgtgc cgctctatct gtgagcgcgc gcgccagggc     360
tgcgaagccc tcatgaacaa gttcggtttt cagtggcccg agcgcctgcg ctgcgagcac     420
ttcccgcgcc acggcgccga gcagatctgc gtcggccaga accactccga ggacggagct     480
cccgcgctac tcaccaccgc gccgccgccg ggactgcagc cgggtgccgg gggcacccgg     540
ggtggcccgg gcggcggcgg cgctcccccg cgctacgcca cgctggagca ccccttccac     600
tgcccgcgcg tcctcaaggt gccatcctat ctcagctaca gtttctgggc gagcgtgat      660 tgtgctgcgc cctgcgaacc tgcgcggccc gatggttcca tgttcttctc acaggaggcc     720
gagcctaggt cttcagacaa aactcacaca tgcccaccgt gcccagcacc tgaagccgag     780 gggccccgt cagtcttcct cttccccca aaacccaagg acaccctcat gatctcccgg       840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcgc cgtctccaac aaagccctcc cagcctccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct     1260 cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga gagcctctc cctgtctccg ggtaaatga                            1419

<210> SEQ ID NO 71
<211> LENGTH: 1437
<212> TYPE: DNA
<213> ORGANISM: Artificial
<220> FEATURE:
<223> OTHER INFORMATION: DNA encoding fusion protein

<400> SEQUENCE: 71
```

```
atgcggcccc gcagcgccct gccccgcctg ctgctgccgc tgctgctgct gccgccgcc    60
gggccggccc agttccacgg ggagaagggc atctccatcc cggaccacgg cttctgccag   120
cccatctcca tcccgctgtg cacggacatc gcctacaacc agaccatcat gcccaacctt   180
ctgggccaca cgaaccagga ggacgcaggc ctagaggtgc accagttcta tccgctggtg   240
aaggtgcagt gctcgcccga actgcgcttc ttcctgtgct ccatgtacgc acccgtgtgc   300
accgtgctgg aacaggccat cccgccgtgc cgctctatct gtgagcgcgc gcgccagggc   360
tgcgaagccc tcatgaacaa gttcggtttt cagtggcccg agcgcctgcg ctgcgagcac   420
ttcccgcgcc acgcgccga gcagatctgc gtcggccaga accactccga ggacggagct   480
cccgcgctac tcaccaccgc gccgccgccg ggactgcagc cgggtgccgg ggcaccccg    540
ggtggcccgg cgcgcggcgg cgctcccccg cgctacgcca cgctggagca ccccttccac   600
tgcccgcgcg tcctcaaggt gccatcctat ctcagctaca gtttctgggc gagcgtgat    660
tgtgctgcgc cctgcgaacc tgcgcggccc gatggttcca tgttcttctc acaggaggag   720
acgcgtttcg cgcgcgccga gcctaggtct tcagacaaaa ctcacacatg cccaccgtgc   780
ccagcacctg aagccgaggg ggccccgtca gtcttcctct ccccccaaa acccaaggac    840
accctcatga tctcccggac ccctgaggtc acatgcgtgg tggtggacgt gagccacgaa   900
gaccctgagg tcaagttcaa ctggtacgtg gacggcgtgg aggtgcataa tgccaagaca   960
aagccgcggg aggagcagta caacagcacg taccgtgtgg tcagcgtcct caccgtcctg  1020
caccaggact ggctgaatgg caaggagtac aagtgcgccg tctccaacaa agccctccca  1080
gcctccatcg agaaaaccat ctccaaagcc aaagggcagc ccgagaacc acaggtgtac   1140
accctgcccc catcccggga tgagctgacc aagaaccagg tcagcctgac ctgcctggtc  1200
aaaggcttct atcccagcga catcgccgtg gagtgggaga gcaatgggca gccggagaac  1260
aactacaaga ccacgcctcc cgtgctggac tccgacggct ccttcttcct ctacagcaag  1320
ctcaccgtgg acaagagcag gtggcagcag gggaacgtct tctcatgctc cgtgatgcat  1380
gaggctctgc acaaccacta cacgcagaag agcctctccc tgtctccggg taaatga     1437
```

<210> SEQ ID NO 72
<211> LENGTH: 386
<212> TYPE: PRT
<213> ORGANISM: Artificial
<220> FEATURE:
<223> OTHER INFORMATION: fusion protein

<400> SEQUENCE: 72

```
Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110
```

```
Leu Arg Cys Glu His Phe Pro Arg His Gly Ala Glu Gln Ile Cys Val
            115                 120                 125

Gly Gln Asn His Ser Glu Asp Gly Ala Pro Ala Leu Leu Thr Thr Ala
        130                 135                 140

Pro Pro Pro Gly Leu Gln Pro Gly Ala Ala Glu Pro Arg Ser Ser Asp
145                 150                 155                 160

Lys Thr His Thr Cys Pro Pro Cys Pro Ala Pro Glu Ala Glu Gly Ala
                165                 170                 175

Pro Ser Val Phe Leu Phe Pro Pro Lys Pro Lys Asp Thr Leu Met Ile
                180                 185                 190

Ser Arg Thr Pro Glu Val Thr Cys Val Val Val Asp Val Ser His Glu
            195                 200                 205

Asp Pro Glu Val Lys Phe Asn Trp Tyr Val Asp Gly Val Glu Val His
            210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Ala Val Ser Asn Lys Ala Leu Pro Ala Ser Ile Glu
            260                 265                 270

Lys Thr Ile Ser Lys Ala Lys Gly Gln Pro Arg Glu Pro Gln Val Tyr
            275                 280                 285

Thr Leu Pro Pro Ser Arg Asp Glu Leu Thr Lys Asn Gln Val Ser Leu
            290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Lys Leu Thr Val Asp
                340                 345                 350

Lys Ser Arg Trp Gln Gln Gly Asn Val Phe Ser Cys Ser Val Met His
            355                 360                 365

Glu Ala Leu His Asn His Tyr Thr Gln Lys Ser Leu Ser Leu Ser Pro
            370                 375                 380

Gly Lys
385

<210> SEQ ID NO 73
<211> LENGTH: 387
<212> TYPE: PRT
<213> ORGANISM: Artificial
<220> FEATURE:
<223> OTHER INFORMATION: fusion protein

<400> SEQUENCE: 73

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
50                  55                  60

Leu Arg Phe Phe Leu Cys Ser Met Tyr Ala Pro Val Cys Thr Val Leu
65                  70                  75                  80
```

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Ala Glu Pro Arg Ser Ser
145                 150                 155                 160

Asp Lys Thr His Thr Cys Pro Pro Cys Pro Ala Pro Glu Ala Glu Gly
                165                 170                 175

Ala Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
    210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Ala Val Ser Asn Lys Ala Leu Pro Ala Ser Ile
            260                 265                 270

Glu Lys Thr Ile Ser Lys Ala Lys Gly Gln Pro Arg Glu Pro Gln Val
        275                 280                 285

Tyr Thr Leu Pro Pro Ser Arg Asp Glu Leu Thr Lys Asn Gln Val Ser
    290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser Leu Ser Leu Ser
    370                 375                 380

Pro Gly Lys
385

<210> SEQ ID NO 74
<211> LENGTH: 388
<212> TYPE: PRT
<213> ORGANISM: Artificial
<220> FEATURE:
<223> OTHER INFORMATION: fusion protein

<400> SEQUENCE: 74

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
                50                  55                  60

Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
                    85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Ala Glu Pro Arg Ser
145                 150                 155                 160

Ser Asp Lys Thr His Thr Cys Pro Pro Cys Pro Ala Pro Glu Ala Glu
                165                 170                 175

Gly Ala Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Ala Val Ser Asn Lys Ala Leu Pro Ala Ser
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Asp Glu Leu Thr Lys Asn Gln Val
290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
370                 375                 380

Ser Pro Gly Lys
385

<210> SEQ ID NO 75
<211> LENGTH: 389
<212> TYPE: PRT
<213> ORGANISM: Artificial
<220> FEATURE:
<223> OTHER INFORMATION: fusion protein

<400> SEQUENCE: 75

Gln Phe His Gly Glu Lys Gly Ile Ser Ile Pro Asp His Gly Phe Cys
 1               5                  10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
 50                  55                  60

Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
            115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Gly Thr Ala Glu Pro Arg
145                 150                 155                 160

Ser Ser Asp Lys Thr His Thr Cys Pro Pro Cys Pro Ala Pro Glu Ala
                165                 170                 175

Glu Gly Ala Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
            195                 200                 205

Ser His Glu Asp Pro Glu Val Lys Phe Asn Trp Tyr Val Asp Gly Val
            210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Ala Val Ser Asn Lys Ala Leu Pro Ala
            260                 265                 270

Ser Ile Glu Lys Thr Ile Ser Lys Ala Lys Gly Gln Pro Arg Glu Pro
            275                 280                 285

Gln Val Tyr Thr Leu Pro Pro Ser Arg Asp Glu Leu Thr Lys Asn Gln
            290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
            355                 360                 365

Val Met His Glu Ala Leu His Asn His Tyr Thr Gln Lys Ser Leu Ser
370                 375                 380

Leu Ser Pro Gly Lys
385

<210> SEQ ID NO 76
<211> LENGTH: 390
<212> TYPE: PRT
<213> ORGANISM: Artificial
<220> FEATURE:

<223> OTHER INFORMATION: fusion protein

<400> SEQUENCE: 76

```
Gln Phe His Gly Glu Lys Gly Ile Ser Ile Pro Asp His Gly Phe Cys
1               5                   10                  15
Gln Pro Ile Ser Ile Pro Leu Cys Thr Asp Ile Ala Tyr Asn Gln Thr
            20                  25                  30
Ile Met Pro Asn Leu Leu Gly His Thr Asn Gln Glu Asp Ala Gly Leu
        35                  40                  45
Glu Val His Gln Phe Tyr Pro Leu Val Lys Val Gln Cys Ser Pro Glu
    50                  55                  60
Leu Arg Phe Phe Leu Cys Ser Met Tyr Ala Pro Val Cys Thr Val Leu
65                  70                  75                  80
Glu Gln Ala Ile Pro Pro Cys Arg Ser Ile Cys Glu Arg Ala Arg Gln
                85                  90                  95
Gly Cys Glu Ala Leu Met Asn Lys Phe Gly Phe Gln Trp Pro Glu Arg
            100                 105                 110
Leu Arg Cys Glu His Phe Pro Arg His Gly Ala Glu Gln Ile Cys Val
        115                 120                 125
Gly Gln Asn His Ser Glu Asp Gly Ala Pro Ala Leu Leu Thr Thr Ala
    130                 135                 140
Pro Pro Pro Gly Leu Gln Pro Gly Ala Gly Thr Pro Ala Glu Pro
145                 150                 155                 160
Arg Ser Ser Asp Lys Thr His Thr Cys Pro Pro Cys Pro Ala Pro Glu
                165                 170                 175
Ala Glu Gly Ala Pro Ser Val Phe Leu Phe Pro Pro Lys Pro Lys Asp
            180                 185                 190
Thr Leu Met Ile Ser Arg Thr Pro Glu Val Thr Cys Val Val Val Asp
        195                 200                 205
Val Ser His Glu Asp Pro Glu Val Lys Phe Asn Trp Tyr Val Asp Gly
    210                 215                 220
Val Glu Val His Asn Ala Lys Thr Lys Pro Arg Glu Glu Gln Tyr Asn
225                 230                 235                 240
Ser Thr Tyr Arg Val Val Ser Val Leu Thr Val Leu His Gln Asp Trp
                245                 250                 255
Leu Asn Gly Lys Glu Tyr Lys Cys Ala Val Ser Asn Lys Ala Leu Pro
            260                 265                 270
Ala Ser Ile Glu Lys Thr Ile Ser Lys Ala Lys Gly Gln Pro Arg Glu
        275                 280                 285
Pro Gln Val Tyr Thr Leu Pro Pro Ser Arg Asp Glu Leu Thr Lys Asn
    290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
            340                 345                 350
Leu Thr Val Asp Lys Ser Arg Trp Gln Gln Gly Asn Val Phe Ser Cys
        355                 360                 365
Ser Val Met His Glu Ala Leu His Asn His Tyr Thr Gln Lys Ser Leu
    370                 375                 380
Ser Leu Ser Pro Gly Lys
385                 390
```

```
<210> SEQ ID NO 77
<211> LENGTH: 391
<212> TYPE: PRT
<213> ORGANISM: Artificial
<220> FEATURE:
<223> OTHER INFORMATION: fusion protein

<400> SEQUENCE: 77
```

| | | | | | | | | | | | | | | |
|---|---|---|---|---|---|---|---|---|---|---|---|---|---|---|
| Gln | Phe | His | Gly | Glu | Lys | Gly | Ile | Ser | Ile | Pro | Asp | His | Gly | Phe | Cys |
| 1 | | | | 5 | | | | | 10 | | | | | 15 |

| Gln | Pro | Ile | Ser | Ile | Pro | Leu | Cys | Thr | Asp | Ile | Ala | Tyr | Asn | Gln | Thr |
|---|---|---|---|---|---|---|---|---|---|---|---|---|---|---|---|
| | | | 20 | | | | 25 | | | | 30 | | | | |

| Ile | Met | Pro | Asn | Leu | Leu | Gly | His | Thr | Asn | Gln | Glu | Asp | Ala | Gly | Leu |
|---|---|---|---|---|---|---|---|---|---|---|---|---|---|---|---|
| | | 35 | | | | | 40 | | | | | 45 | | | |

| Glu | Val | His | Gln | Phe | Tyr | Pro | Leu | Val | Lys | Val | Gln | Cys | Ser | Pro | Glu |
|---|---|---|---|---|---|---|---|---|---|---|---|---|---|---|---|
| | 50 | | | | | 55 | | | | | 60 | | | | |

| Leu | Arg | Phe | Phe | Leu | Cys | Ser | Met | Tyr | Ala | Pro | Val | Cys | Thr | Val | Leu |
|---|---|---|---|---|---|---|---|---|---|---|---|---|---|---|---|
| 65 | | | | | 70 | | | | | 75 | | | | | 80 |

| Glu | Gln | Ala | Ile | Pro | Pro | Cys | Arg | Ser | Ile | Cys | Glu | Arg | Ala | Arg | Gln |
|---|---|---|---|---|---|---|---|---|---|---|---|---|---|---|---|
| | | | | 85 | | | | | 90 | | | | | 95 | |

| Gly | Cys | Glu | Ala | Leu | Met | Asn | Lys | Phe | Gly | Phe | Gln | Trp | Pro | Glu | Arg |
|---|---|---|---|---|---|---|---|---|---|---|---|---|---|---|---|
| | | | 100 | | | | | 105 | | | | | 110 | | |

| Leu | Arg | Cys | Glu | His | Phe | Pro | Arg | His | Gly | Ala | Glu | Gln | Ile | Cys | Val |
|---|---|---|---|---|---|---|---|---|---|---|---|---|---|---|---|
| | | | 115 | | | | | 120 | | | | | 125 | | |

| Gly | Gln | Asn | His | Ser | Glu | Asp | Gly | Ala | Pro | Ala | Leu | Leu | Thr | Thr | Ala |
|---|---|---|---|---|---|---|---|---|---|---|---|---|---|---|---|
| | 130 | | | | | 135 | | | | | 140 | | | | |

| Pro | Pro | Pro | Gly | Leu | Gln | Pro | Gly | Ala | Gly | Thr | Pro | Gly | Ala | Glu |
|---|---|---|---|---|---|---|---|---|---|---|---|---|---|---|
| 145 | | | | | 150 | | | | | 155 | | | | 160 |

| Pro | Arg | Ser | Ser | Asp | Lys | Thr | His | Thr | Cys | Pro | Pro | Cys | Pro | Ala | Pro |
|---|---|---|---|---|---|---|---|---|---|---|---|---|---|---|---|
| | | | | 165 | | | | | 170 | | | | | 175 | |

| Glu | Ala | Glu | Gly | Ala | Pro | Ser | Val | Phe | Leu | Phe | Pro | Pro | Lys | Pro | Lys |
|---|---|---|---|---|---|---|---|---|---|---|---|---|---|---|---|
| | | | 180 | | | | | 185 | | | | | 190 | | |

| Asp | Thr | Leu | Met | Ile | Ser | Arg | Thr | Pro | Glu | Val | Thr | Cys | Val | Val | Val |
|---|---|---|---|---|---|---|---|---|---|---|---|---|---|---|---|
| | 195 | | | | | 200 | | | | | 205 | | | | |

| Asp | Val | Ser | His | Glu | Asp | Pro | Glu | Val | Lys | Phe | Asn | Trp | Tyr | Val | Asp |
|---|---|---|---|---|---|---|---|---|---|---|---|---|---|---|---|
| | 210 | | | | | 215 | | | | | 220 | | | | |

| Gly | Val | Glu | Val | His | Asn | Ala | Lys | Thr | Lys | Pro | Arg | Glu | Glu | Gln | Tyr |
|---|---|---|---|---|---|---|---|---|---|---|---|---|---|---|---|
| 225 | | | | | 230 | | | | | 235 | | | | | 240 |

| Asn | Ser | Thr | Tyr | Arg | Val | Val | Ser | Val | Leu | Thr | Val | Leu | His | Gln | Asp |
|---|---|---|---|---|---|---|---|---|---|---|---|---|---|---|---|
| | | | | 245 | | | | | 250 | | | | | 255 | |

| Trp | Leu | Asn | Gly | Lys | Glu | Tyr | Lys | Cys | Ala | Val | Ser | Asn | Lys | Ala | Leu |
|---|---|---|---|---|---|---|---|---|---|---|---|---|---|---|---|
| | | | | 260 | | | | | 265 | | | | | 270 | |

| Pro | Ala | Ser | Ile | Glu | Lys | Thr | Ile | Ser | Lys | Ala | Lys | Gly | Gln | Pro | Arg |
|---|---|---|---|---|---|---|---|---|---|---|---|---|---|---|---|
| | | | 275 | | | | | 280 | | | | | 285 | | |

| Glu | Pro | Gln | Val | Tyr | Thr | Leu | Pro | Pro | Ser | Arg | Asp | Glu | Leu | Thr | Lys |
|---|---|---|---|---|---|---|---|---|---|---|---|---|---|---|---|
| | 290 | | | | | 295 | | | | | 300 | | | | |

| Asn | Gln | Val | Ser | Leu | Thr | Cys | Leu | Val | Lys | Gly | Phe | Tyr | Pro | Ser | Asp |
|---|---|---|---|---|---|---|---|---|---|---|---|---|---|---|---|
| 305 | | | | | 310 | | | | | 315 | | | | | 320 |

| Ile | Ala | Val | Glu | Trp | Glu | Ser | Asn | Gly | Gln | Pro | Glu | Asn | Asn | Tyr | Lys |
|---|---|---|---|---|---|---|---|---|---|---|---|---|---|---|---|
| | | | | 325 | | | | | 330 | | | | | 335 | |

| Thr | Thr | Pro | Pro | Val | Leu | Asp | Ser | Asp | Gly | Ser | Phe | Phe | Leu | Tyr | Ser |
|---|---|---|---|---|---|---|---|---|---|---|---|---|---|---|---|
| | | | 340 | | | | | 345 | | | | | 350 | | |

| Lys | Leu | Thr | Val | Asp | Lys | Ser | Arg | Trp | Gln | Gln | Gly | Asn | Val | Phe | Ser |
|---|---|---|---|---|---|---|---|---|---|---|---|---|---|---|---|
| | | | 355 | | | | | 360 | | | | | 365 | | |

```
Cys Ser Val Met His Glu Ala Leu His Asn His Tyr Thr Gln Lys Ser
    370                 375                 380

Leu Ser Leu Ser Pro Gly Lys
385                 390

<210> SEQ ID NO 78
<211> LENGTH: 392
<212> TYPE: PRT
<213> ORGANISM: Artificial
<220> FEATURE:
<223> OTHER INFORMATION: fusion protein

<400> SEQUENCE: 78

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Gly Thr Pro Gly Gly Ala
145                 150                 155                 160

Glu Pro Arg Ser Ser Asp Lys Thr His Thr Cys Pro Pro Cys Pro Ala
                165                 170                 175

Pro Glu Ala Glu Gly Ala Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
                245                 250                 255

Asp Trp Leu Asn Gly Lys Glu Tyr Lys Cys Ala Val Ser Asn Lys Ala
            260                 265                 270

Leu Pro Ala Ser Ile Glu Lys Thr Ile Ser Lys Ala Lys Gly Gln Pro
        275                 280                 285

Arg Glu Pro Gln Val Tyr Thr Leu Pro Pro Ser Arg Asp Glu Leu Thr
290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335
```

```
Lys Thr Thr Pro Pro Val Leu Asp Ser Asp Gly Ser Phe Phe Leu Tyr
                340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390

<210> SEQ ID NO 79
<211> LENGTH: 393
<212> TYPE: PRT
<213> ORGANISM: Artificial
<220> FEATURE:
<223> OTHER INFORMATION: fusion protein

<400> SEQUENCE: 79

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Gly Thr Pro Gly Gly Pro
145                 150                 155                 160

Ala Glu Pro Arg Ser Ser Asp Lys Thr His Thr Cys Pro Pro Cys Pro
                165                 170                 175

Ala Pro Glu Ala Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Ala Val Ser Asn Lys
            260                 265                 270

Ala Leu Pro Ala Ser Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300
```

```
Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
            325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390
```

<210> SEQ ID NO 80
<211> LENGTH: 394
<212> TYPE: PRT
<213> ORGANISM: Artificial
<220> FEATURE:
<223> OTHER INFORMATION: fusion protein

<400> SEQUENCE: 80

```
Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Gly Thr Pro Gly Gly Pro
145                 150                 155                 160

Gly Ala Glu Pro Arg Ser Ser Asp Lys Thr His Thr Cys Pro Pro Cys
                165                 170                 175

Pro Ala Pro Glu Ala Glu Gly Ala Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser His Glu Asp Pro Glu Val Lys Phe Asn Trp
210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Ala Val Ser Asn
            260                 265                 270
```

```
Lys Ala Leu Pro Ala Ser Ile Glu Lys Thr Ile Ser Lys Ala Lys Gly
            275                 280                 285

Gln Pro Arg Glu Pro Gln Val Tyr Thr Leu Pro Ser Arg Asp Glu
290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
            355                 360                 365

Val Phe Ser Cys Ser Val Met His Glu Ala Leu His Asn His Tyr Thr
370                 375                 380

Gln Lys Ser Leu Ser Leu Ser Pro Gly Lys
385                 390
```

<210> SEQ ID NO 81
<211> LENGTH: 395
<212> TYPE: PRT
<213> ORGANISM: Artificial
<220> FEATURE:
<223> OTHER INFORMATION: fusion protein

<400> SEQUENCE: 81

```
Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Gly Thr Pro Gly Gly Pro
145                 150                 155                 160

Gly Gly Ala Glu Pro Arg Ser Ser Asp Lys Thr His Thr Cys Pro Pro
                165                 170                 175

Cys Pro Ala Pro Glu Ala Glu Gly Ala Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
210                 215                 220

Trp Tyr Val Asp Gly Val Glu Val His Asn Ala Lys Thr Lys Pro Arg
225                 230                 235                 240
```

```
Glu Glu Gln Tyr Asn Ser Thr Tyr Arg Val Val Ser Val Leu Thr Val
                245                 250                 255

Leu His Gln Asp Trp Leu Asn Gly Lys Glu Tyr Lys Cys Ala Val Ser
            260                 265                 270

Asn Lys Ala Leu Pro Ala Ser Ile Glu Lys Thr Ile Ser Lys Ala Lys
        275                 280                 285

Gly Gln Pro Arg Glu Pro Gln Val Tyr Thr Leu Pro Pro Ser Arg Asp
    290                 295                 300

Glu Leu Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
    370                 375                 380

Thr Gln Lys Ser Leu Ser Leu Ser Pro Gly Lys
385                 390                 395

<210> SEQ ID NO 82
<211> LENGTH: 396
<212> TYPE: PRT
<213> ORGANISM: Artificial
<220> FEATURE:
<223> OTHER INFORMATION: fusion protein

<400> SEQUENCE: 82

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Thr Pro Gly Gly Pro
145                 150                 155                 160

Gly Gly Gly Ala Glu Pro Arg Ser Ser Asp Lys Thr His Thr Cys Pro
                165                 170                 175

Pro Cys Pro Ala Pro Glu Ala Glu Gly Ala Pro Ser Val Phe Leu Phe
            180                 185                 190

Pro Pro Lys Pro Lys Asp Thr Leu Met Ile Ser Arg Thr Pro Glu Val
        195                 200                 205
```

```
Thr Cys Val Val Val Asp Val Ser His Glu Asp Pro Glu Val Lys Phe
    210                 215                 220
Asn Trp Tyr Val Asp Gly Val Glu Val His Asn Ala Lys Thr Lys Pro
225                 230                 235                 240
Arg Glu Glu Gln Tyr Asn Ser Thr Tyr Arg Val Val Ser Val Leu Thr
                245                 250                 255
Val Leu His Gln Asp Trp Leu Asn Gly Lys Glu Tyr Lys Cys Ala Val
                260                 265                 270
Ser Asn Lys Ala Leu Pro Ala Ser Ile Glu Lys Thr Ile Ser Lys Ala
            275                 280                 285
Lys Gly Gln Pro Arg Glu Pro Gln Val Tyr Thr Leu Pro Pro Ser Arg
290                 295                 300
Asp Glu Leu Thr Lys Asn Gln Val Ser Leu Thr Cys Leu Val Lys Gly
305                 310                 315                 320
Phe Tyr Pro Ser Asp Ile Ala Val Glu Trp Glu Ser Asn Gly Gln Pro
                325                 330                 335
Glu Asn Asn Tyr Lys Thr Thr Pro Pro Val Leu Asp Ser Asp Gly Ser
                340                 345                 350
Phe Phe Leu Tyr Ser Lys Leu Thr Val Asp Lys Ser Arg Trp Gln Gln
            355                 360                 365
Gly Asn Val Phe Ser Cys Ser Val Met His Glu Ala Leu His Asn His
370                 375                 380
Tyr Thr Gln Lys Ser Leu Ser Leu Ser Pro Gly Lys
385                 390                 395

<210> SEQ ID NO 83
<211> LENGTH: 397
<212> TYPE: PRT
<213> ORGANISM: Artificial
<220> FEATURE:
<223> OTHER INFORMATION: fusion protein

<400> SEQUENCE: 83

Gln Phe His Gly Glu Lys Gly Ile Ser Ile Pro Asp His Gly Phe Cys
1               5                   10                  15
Gln Pro Ile Ser Ile Pro Leu Cys Thr Asp Ile Ala Tyr Asn Gln Thr
                20                  25                  30
Ile Met Pro Asn Leu Leu Gly His Thr Asn Gln Glu Asp Ala Gly Leu
            35                  40                  45
Glu Val His Gln Phe Tyr Pro Leu Val Lys Val Gln Cys Ser Pro Glu
        50                  55                  60
Leu Arg Phe Phe Leu Cys Ser Met Tyr Ala Pro Val Cys Thr Val Leu
65                  70                  75                  80
Glu Gln Ala Ile Pro Pro Cys Arg Ser Ile Cys Glu Arg Ala Arg Gln
                85                  90                  95
Gly Cys Glu Ala Leu Met Asn Lys Phe Gly Phe Gln Trp Pro Glu Arg
            100                 105                 110
Leu Arg Cys Glu His Phe Pro Arg His Gly Ala Glu Gln Ile Cys Val
        115                 120                 125
Gly Gln Asn His Ser Glu Asp Gly Ala Pro Ala Leu Leu Thr Thr Ala
    130                 135                 140
Pro Pro Pro Gly Leu Gln Pro Gly Ala Gly Thr Pro Gly Gly Pro
145                 150                 155                 160
Gly Gly Gly Gly Ala Glu Pro Arg Ser Ser Asp Lys Thr His Thr Cys
                165                 170                 175
```

```
Pro Pro Cys Pro Ala Pro Glu Ala Glu Gly Ala Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser His Glu Asp Pro Glu Val Lys
    210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
                245                 250                 255

Thr Val Leu His Gln Asp Trp Leu Asn Gly Lys Glu Tyr Lys Cys Ala
            260                 265                 270

Val Ser Asn Lys Ala Leu Pro Ala Ser Ile Glu Lys Thr Ile Ser Lys
    275                 280                 285

Ala Lys Gly Gln Pro Arg Glu Pro Gln Val Tyr Thr Leu Pro Pro Ser
    290                 295                 300

Arg Asp Glu Leu Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
    370                 375                 380

His Tyr Thr Gln Lys Ser Leu Ser Leu Ser Pro Gly Lys
385                 390                 395

<210> SEQ ID NO 84
<211> LENGTH: 398
<212> TYPE: PRT
<213> ORGANISM: Artificial
<220> FEATURE:
<223> OTHER INFORMATION: fusion protein

<400> SEQUENCE: 84

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140
```

Pro Pro Pro Gly Leu Gln Pro Gly Ala Gly Thr Pro Gly Gly Pro
145                 150                 155                 160

Gly Gly Gly Gly Ala Ala Glu Pro Arg Ser Ser Asp Lys Thr His Thr
                165                 170                 175

Cys Pro Pro Cys Pro Ala Pro Glu Ala Glu Gly Ala Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser His Glu Asp Pro Glu Val
210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Ala Val Ser Asn Lys Ala Leu Pro Ala Ser Ile Glu Lys Thr Ile Ser
        275                 280                 285

Lys Ala Lys Gly Gln Pro Arg Glu Pro Gln Val Tyr Thr Leu Pro Pro
290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350

Gly Ser Phe Phe Leu Tyr Ser Lys Leu Thr Val Asp Lys Ser Arg Trp
        355                 360                 365

Gln Gln Gly Asn Val Phe Ser Cys Ser Val Met His Glu Ala Leu His
370                 375                 380

Asn His Tyr Thr Gln Lys Ser Leu Ser Leu Ser Pro Gly Lys
385                 390                 395

<210> SEQ ID NO 85
<211> LENGTH: 399
<212> TYPE: PRT
<213> ORGANISM: Artificial
<220> FEATURE:
<223> OTHER INFORMATION: fusion protein

<400> SEQUENCE: 85

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
            35                  40                  45

Glu Val His Gln Phe Tyr Pro Leu Val Lys Val Gln Cys Ser Pro Glu
        50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

```
Leu Arg Cys Glu His Phe Pro Arg His Gly Ala Glu Gln Ile Cys Val
            115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Thr Pro Gly Gly Pro
145                 150                 155                 160

Gly Gly Gly Gly Ala Pro Ala Glu Pro Arg Ser Ser Asp Lys Thr His
                165                 170                 175

Thr Cys Pro Pro Cys Pro Ala Pro Glu Ala Gly Ala Pro Ser Val
            180                 185                 190

Phe Leu Phe Pro Pro Lys Pro Lys Asp Thr Leu Met Ile Ser Arg Thr
            195                 200                 205

Pro Glu Val Thr Cys Val Val Val Asp Val Ser His Glu Asp Pro Glu
            210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Ala Val Ser Asn Lys Ala Leu Pro Ala Ser Ile Glu Lys Thr Ile
            275                 280                 285

Ser Lys Ala Lys Gly Gln Pro Arg Glu Pro Gln Val Tyr Thr Leu Pro
            290                 295                 300

Pro Ser Arg Asp Glu Leu Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
            355                 360                 365

Trp Gln Gln Gly Asn Val Phe Ser Cys Ser Val Met His Glu Ala Leu
            370                 375                 380

His Asn His Tyr Thr Gln Lys Ser Leu Ser Leu Ser Pro Gly Lys
385                 390                 395

<210> SEQ ID NO 86
<211> LENGTH: 400
<212> TYPE: PRT
<213> ORGANISM: Artificial
<220> FEATURE:
<223> OTHER INFORMATION: fusion protein

<400> SEQUENCE: 86

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
            35                  40                  45

Glu Val His Gln Phe Tyr Pro Leu Val Lys Val Gln Cys Ser Pro Glu
        50                  55                  60

Leu Arg Phe Phe Leu Cys Ser Met Tyr Ala Pro Val Cys Thr Val Leu
65                  70                  75                  80
```

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Thr Pro Gly Gly Pro
145                 150                 155                 160

Gly Gly Gly Ala Pro Pro Ala Glu Pro Arg Ser Ser Asp Lys Thr
            165                 170                 175

His Thr Cys Pro Pro Cys Pro Ala Pro Glu Ala Glu Gly Ala Pro Ser
        180                 185                 190

Val Phe Leu Phe Pro Pro Lys Pro Lys Asp Thr Leu Met Ile Ser Arg
    195                 200                 205

Thr Pro Glu Val Thr Cys Val Val Val Asp Val Ser His Glu Asp Pro
210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
            245                 250                 255

Ser Val Leu Thr Val Leu His Gln Asp Trp Leu Asn Gly Lys Glu Tyr
        260                 265                 270

Lys Cys Ala Val Ser Asn Lys Ala Leu Pro Ala Ser Ile Glu Lys Thr
    275                 280                 285

Ile Ser Lys Ala Lys Gly Gln Pro Arg Glu Pro Gln Val Tyr Thr Leu
290                 295                 300

Pro Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu Ser
            325                 330                 335

Asn Gly Gln Pro Glu Asn Asn Tyr Lys Thr Thr Pro Pro Val Leu Asp
        340                 345                 350

Ser Asp Gly Ser Phe Phe Leu Tyr Ser Lys Leu Thr Val Asp Lys Ser
    355                 360                 365

Arg Trp Gln Gln Gly Asn Val Phe Ser Cys Ser Val Met His Glu Ala
370                 375                 380

Leu His Asn His Tyr Thr Gln Lys Ser Leu Ser Leu Ser Pro Gly Lys
385                 390                 395                 400

<210> SEQ ID NO 87
<211> LENGTH: 401
<212> TYPE: PRT
<213> ORGANISM: Artificial
<220> FEATURE:
<223> OTHER INFORMATION: fusion protein

<400> SEQUENCE: 87

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

```
Glu Val His Gln Phe Tyr Pro Leu Val Lys Val Gln Cys Ser Pro Glu
 50                  55                  60

Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
             85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Gly Leu Gln Pro Gly Ala Gly Thr Pro Gly Gly Pro
145                 150                 155                 160

Gly Gly Gly Gly Ala Pro Pro Arg Ala Glu Pro Arg Ser Ser Asp Lys
                165                 170                 175

Thr His Thr Cys Pro Pro Cys Pro Ala Pro Glu Ala Glu Gly Ala Pro
                180                 185                 190

Ser Val Phe Leu Phe Pro Pro Lys Pro Lys Asp Thr Leu Met Ile Ser
            195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Ala Val Ser Asn Lys Ala Leu Pro Ala Ser Ile Glu Lys
        275                 280                 285

Thr Ile Ser Lys Ala Lys Gly Gln Pro Arg Glu Pro Gln Val Tyr Thr
290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro Gly
385                 390                 395                 400

Lys

<210> SEQ ID NO 88
<211> LENGTH: 402
<212> TYPE: PRT
<213> ORGANISM: Artificial
<220> FEATURE:
<223> OTHER INFORMATION: fusion protein

<400> SEQUENCE: 88

Gln Phe His Gly Glu Lys Gly Ile Ser Ile Pro Asp His Gly Phe Cys
```

```
1               5                   10                  15
Gln Pro Ile Ser Ile Pro Leu Cys Thr Asp Ile Ala Tyr Asn Gln Thr
                20                  25                  30
Ile Met Pro Asn Leu Leu Gly His Thr Asn Gln Glu Asp Ala Gly Leu
                35                  40                  45
Glu Val His Gln Phe Tyr Pro Leu Val Lys Val Gln Cys Ser Pro Glu
        50                  55                  60
Leu Arg Phe Phe Leu Cys Ser Met Tyr Ala Pro Val Cys Thr Val Leu
65                  70                  75                  80
Glu Gln Ala Ile Pro Pro Cys Arg Ser Ile Cys Glu Arg Ala Arg Gln
                85                  90                  95
Gly Cys Glu Ala Leu Met Asn Lys Phe Gly Phe Gln Trp Pro Glu Arg
                100                 105                 110
Leu Arg Cys Glu His Phe Pro Arg His Gly Ala Glu Gln Ile Cys Val
                115                 120                 125
Gly Gln Asn His Ser Glu Asp Gly Ala Pro Ala Leu Leu Thr Thr Ala
                130                 135                 140
Pro Pro Pro Gly Leu Gln Pro Gly Ala Gly Gly Thr Pro Gly Gly Pro
145                 150                 155                 160
Gly Gly Gly Gly Ala Pro Pro Arg Tyr Ala Glu Pro Arg Ser Ser Asp
                165                 170                 175
Lys Thr His Thr Cys Pro Pro Cys Pro Ala Pro Glu Ala Glu Gly Ala
                180                 185                 190
Pro Ser Val Phe Leu Phe Pro Pro Lys Pro Lys Asp Thr Leu Met Ile
                195                 200                 205
Ser Arg Thr Pro Glu Val Thr Cys Val Val Val Asp Val Ser His Glu
210                 215                 220
Asp Pro Glu Val Lys Phe Asn Trp Tyr Val Asp Gly Val Glu Val His
225                 230                 235                 240
Asn Ala Lys Thr Lys Pro Arg Glu Glu Gln Tyr Asn Ser Thr Tyr Arg
                245                 250                 255
Val Val Ser Val Leu Thr Val Leu His Gln Asp Trp Leu Asn Gly Lys
                260                 265                 270
Glu Tyr Lys Cys Ala Val Ser Asn Lys Ala Leu Pro Ala Ser Ile Glu
                275                 280                 285
Lys Thr Ile Ser Lys Ala Lys Gly Gln Pro Arg Glu Pro Gln Val Tyr
                290                 295                 300
Thr Leu Pro Pro Ser Arg Asp Glu Leu Thr Lys Asn Gln Val Ser Leu
305                 310                 315                 320
Thr Cys Leu Val Lys Gly Phe Tyr Pro Ser Asp Ile Ala Val Glu Trp
                325                 330                 335
Glu Ser Asn Gly Gln Pro Glu Asn Asn Tyr Lys Thr Thr Pro Pro Val
                340                 345                 350
Leu Asp Ser Asp Gly Ser Phe Phe Leu Tyr Ser Lys Leu Thr Val Asp
                355                 360                 365
Lys Ser Arg Trp Gln Gln Gly Asn Val Phe Ser Cys Ser Val Met His
                370                 375                 380
Glu Ala Leu His Asn His Tyr Thr Gln Lys Ser Leu Ser Leu Ser Pro
385                 390                 395                 400
Gly Lys

<210> SEQ ID NO 89
<211> LENGTH: 403
```

```
<212> TYPE: PRT
<213> ORGANISM: Artificial
<220> FEATURE:
<223> OTHER INFORMATION: fusion protein

<400> SEQUENCE: 89

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Ala Glu Pro Arg Ser Ser
                165                 170                 175

Asp Lys Thr His Thr Cys Pro Pro Cys Pro Ala Pro Glu Ala Glu Gly
            180                 185                 190

Ala Pro Ser Val Phe Leu Phe Pro Pro Lys Pro Lys Asp Thr Leu Met
        195                 200                 205

Ile Ser Arg Thr Pro Glu Val Thr Cys Val Val Val Asp Val Ser His
    210                 215                 220

Glu Asp Pro Glu Val Lys Phe Asn Trp Tyr Val Asp Gly Val Glu Val
225                 230                 235                 240

His Asn Ala Lys Thr Lys Pro Arg Glu Glu Gln Tyr Asn Ser Thr Tyr
                245                 250                 255

Arg Val Val Ser Val Leu Thr Val Leu His Gln Asp Trp Leu Asn Gly
            260                 265                 270

Lys Glu Tyr Lys Cys Ala Val Ser Asn Lys Ala Leu Pro Ala Ser Ile
        275                 280                 285

Glu Lys Thr Ile Ser Lys Ala Lys Gly Gln Pro Arg Glu Pro Gln Val
    290                 295                 300

Tyr Thr Leu Pro Pro Ser Arg Asp Glu Leu Thr Lys Asn Gln Val Ser
305                 310                 315                 320

Leu Thr Cys Leu Val Lys Gly Phe Tyr Pro Ser Asp Ile Ala Val Glu
                325                 330                 335

Trp Glu Ser Asn Gly Gln Pro Glu Asn Asn Tyr Lys Thr Thr Pro Pro
            340                 345                 350

Val Leu Asp Ser Asp Gly Ser Phe Phe Leu Tyr Ser Lys Leu Thr Val
        355                 360                 365

Asp Lys Ser Arg Trp Gln Gln Gly Asn Val Phe Ser Cys Ser Val Met
    370                 375                 380
```

```
His Glu Ala Leu His Asn His Tyr Thr Gln Lys Ser Leu Ser Leu Ser
385                 390                 395                 400

Pro Gly Lys

<210> SEQ ID NO 90
<211> LENGTH: 404
<212> TYPE: PRT
<213> ORGANISM: Artificial
<220> FEATURE:
<223> OTHER INFORMATION: fusion protein

<400> SEQUENCE: 90

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Gly Thr Pro Gly Gly Pro
145                 150                 155                 160

Gly Gly Gly Gly Ala Pro Pro Arg Tyr Ala Thr Ala Glu Pro Arg Ser
                165                 170                 175

Ser Asp Lys Thr His Thr Cys Pro Pro Cys Pro Ala Pro Glu Ala Glu
            180                 185                 190

Gly Ala Pro Ser Val Phe Leu Phe Pro Pro Lys Pro Lys Asp Thr Leu
        195                 200                 205

Met Ile Ser Arg Thr Pro Glu Val Thr Cys Val Val Val Asp Val Ser
210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
            260                 265                 270

Gly Lys Glu Tyr Lys Cys Ala Val Ser Asn Lys Ala Leu Pro Ala Ser
        275                 280                 285

Ile Glu Lys Thr Ile Ser Lys Ala Lys Gly Gln Pro Arg Glu Pro Gln
    290                 295                 300

Val Tyr Thr Leu Pro Pro Ser Arg Asp Glu Leu Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
```

```
                340              345              350
Pro Val Leu Asp Ser Asp Gly Ser Phe Phe Leu Tyr Ser Lys Leu Thr
        355                  360                 365
Val Asp Lys Ser Arg Trp Gln Gln Gly Asn Val Phe Ser Cys Ser Val
370                  375                 380
Met His Glu Ala Leu His Asn His Tyr Thr Gln Lys Ser Leu Ser Leu
385                  390                 395                 400
Ser Pro Gly Lys

<210> SEQ ID NO 91
<211> LENGTH: 405
<212> TYPE: PRT
<213> ORGANISM: Artificial
<220> FEATURE:
<223> OTHER INFORMATION: fusion protein

<400> SEQUENCE: 91

Gln Phe His Gly Glu Lys Gly Ile Ser Ile Pro Asp His Gly Phe Cys
1               5                   10                  15
Gln Pro Ile Ser Ile Pro Leu Cys Thr Asp Ile Ala Tyr Asn Gln Thr
            20                  25                  30
Ile Met Pro Asn Leu Leu Gly His Thr Asn Gln Glu Asp Ala Gly Leu
        35                  40                  45
Glu Val His Gln Phe Tyr Pro Leu Val Lys Val Gln Cys Ser Pro Glu
    50                  55                  60
Leu Arg Phe Phe Leu Cys Ser Met Tyr Ala Pro Val Cys Thr Val Leu
65                  70                  75                  80
Glu Gln Ala Ile Pro Pro Cys Arg Ser Ile Cys Glu Arg Ala Arg Gln
                85                  90                  95
Gly Cys Glu Ala Leu Met Asn Lys Phe Gly Phe Gln Trp Pro Glu Arg
            100                 105                 110
Leu Arg Cys Glu His Phe Pro Arg His Gly Ala Glu Gln Ile Cys Val
        115                 120                 125
Gly Gln Asn His Ser Glu Asp Gly Ala Pro Ala Leu Leu Thr Thr Ala
    130                 135                 140
Pro Pro Pro Gly Leu Gln Pro Gly Ala Gly Gly Thr Pro Gly Gly Pro
145                 150                 155                 160
Gly Gly Gly Gly Ala Pro Pro Arg Tyr Ala Thr Leu Ala Glu Pro Arg
                165                 170                 175
Ser Ser Asp Lys Thr His Thr Cys Pro Pro Cys Pro Ala Pro Glu Ala
            180                 185                 190
Glu Gly Ala Pro Ser Val Phe Leu Phe Pro Pro Lys Pro Lys Asp Thr
        195                 200                 205
Leu Met Ile Ser Arg Thr Pro Glu Val Thr Cys Val Val Val Asp Val
    210                 215                 220
Ser His Glu Asp Pro Glu Val Lys Phe Asn Trp Tyr Val Asp Gly Val
225                 230                 235                 240
Glu Val His Asn Ala Lys Thr Lys Pro Arg Glu Glu Gln Tyr Asn Ser
                245                 250                 255
Thr Tyr Arg Val Val Ser Val Leu Thr Val Leu His Gln Asp Trp Leu
            260                 265                 270
Asn Gly Lys Glu Tyr Lys Cys Ala Val Ser Asn Lys Ala Leu Pro Ala
        275                 280                 285
Ser Ile Glu Lys Thr Ile Ser Lys Ala Lys Gly Gln Pro Arg Glu Pro
    290                 295                 300
```

Gln Val Tyr Thr Leu Pro Pro Ser Arg Asp Glu Leu Thr Lys Asn Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Lys Leu
        355                 360                 365

Thr Val Asp Lys Ser Arg Trp Gln Gln Gly Asn Val Phe Ser Cys Ser
370                 375                 380

Val Met His Glu Ala Leu His Asn His Tyr Thr Gln Lys Ser Leu Ser
385                 390                 395                 400

Leu Ser Pro Gly Lys
            405

<210> SEQ ID NO 92
<211> LENGTH: 406
<212> TYPE: PRT
<213> ORGANISM: Artificial
<220> FEATURE:
<223> OTHER INFORMATION: fusion protein

<400> SEQUENCE: 92

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Gly Thr Pro Gly Gly Pro
145                 150                 155                 160

Gly Gly Gly Gly Ala Pro Pro Arg Tyr Ala Thr Leu Glu Ala Glu Pro
                165                 170                 175

Arg Ser Ser Asp Lys Thr His Thr Cys Pro Pro Cys Pro Ala Pro Glu
            180                 185                 190

Ala Glu Gly Ala Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

```
Ser Thr Tyr Arg Val Ser Val Leu Thr Val Leu His Gln Asp Trp
            260                 265                 270

Leu Asn Gly Lys Glu Tyr Lys Cys Ala Val Ser Asn Lys Ala Leu Pro
        275                 280                 285

Ala Ser Ile Glu Lys Thr Ile Ser Lys Ala Lys Gly Gln Pro Arg Glu
290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
                340                 345                 350

Thr Pro Pro Val Leu Asp Ser Asp Gly Ser Phe Phe Leu Tyr Ser Lys
            355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys
                405

<210> SEQ ID NO 93
<211> LENGTH: 407
<212> TYPE: PRT
<213> ORGANISM: Artificial
<220> FEATURE:
<223> OTHER INFORMATION: fusion protein

<400> SEQUENCE: 93

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
                100                 105                 110

Leu Arg Cys Glu His Phe Pro Arg His Gly Ala Glu Gln Ile Cys Val
            115                 120                 125

Gly Gln Asn His Ser Glu Asp Gly Ala Pro Ala Leu Leu Thr Thr Ala
        130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Thr Leu Glu His Ala Glu
                165                 170                 175

Pro Arg Ser Ser Asp Lys Thr His Thr Cys Pro Pro Cys Pro Ala Pro
            180                 185                 190

Glu Ala Glu Gly Ala Pro Ser Val Phe Leu Phe Pro Pro Lys Pro Lys
        195                 200                 205
```

-continued

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Ala Val Ser Asn Lys Ala Leu
        275                 280                 285

Pro Ala Ser Ile Glu Lys Thr Ile Ser Lys Ala Lys Gly Gln Pro Arg
    290                 295                 300

Glu Pro Gln Val Tyr Thr Leu Pro Pro Ser Arg Asp Glu Leu Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400

Leu Ser Leu Ser Pro Gly Lys
                405

<210> SEQ ID NO 94
<211> LENGTH: 408
<212> TYPE: PRT
<213> ORGANISM: Artificial
<220> FEATURE:
<223> OTHER INFORMATION: fusion protein

<400> SEQUENCE: 94

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Gly Thr Pro Gly Gly Pro
145                 150                 155                 160

```
Gly Gly Gly Gly Ala Pro Pro Arg Tyr Ala Thr Leu Glu His Pro Ala
            165                 170                 175
Glu Pro Arg Ser Ser Asp Lys Thr His Thr Cys Pro Pro Cys Pro Ala
            180                 185                 190
Pro Glu Ala Glu Gly Ala Pro Ser Val Phe Leu Phe Pro Pro Lys Pro
            195                 200                 205
Lys Asp Thr Leu Met Ile Ser Arg Thr Pro Glu Val Thr Cys Val Val
210                 215                 220
Val Asp Val Ser His Glu Asp Pro Glu Val Lys Phe Asn Trp Tyr Val
225                 230                 235                 240
Asp Gly Val Glu Val His Asn Ala Lys Thr Lys Pro Arg Glu Glu Gln
            245                 250                 255
Tyr Asn Ser Thr Tyr Arg Val Val Ser Val Leu Thr Val Leu His Gln
            260                 265                 270
Asp Trp Leu Asn Gly Lys Glu Tyr Lys Cys Ala Val Ser Asn Lys Ala
            275                 280                 285
Leu Pro Ala Ser Ile Glu Lys Thr Ile Ser Lys Ala Lys Gly Gln Pro
            290                 295                 300
Arg Glu Pro Gln Val Tyr Thr Leu Pro Pro Ser Arg Asp Glu Leu Thr
305                 310                 315                 320
Lys Asn Gln Val Ser Leu Thr Cys Leu Val Lys Gly Phe Tyr Pro Ser
            325                 330                 335
Asp Ile Ala Val Glu Trp Glu Ser Asn Gly Gln Pro Glu Asn Asn Tyr
            340                 345                 350
Lys Thr Thr Pro Pro Val Leu Asp Ser Asp Gly Ser Phe Phe Leu Tyr
            355                 360                 365
Ser Lys Leu Thr Val Asp Lys Ser Arg Trp Gln Gln Gly Asn Val Phe
            370                 375                 380
Ser Cys Ser Val Met His Glu Ala Leu His Asn His Tyr Thr Gln Lys
385                 390                 395                 400
Ser Leu Ser Leu Ser Pro Gly Lys
            405

<210> SEQ ID NO 95
<211> LENGTH: 411
<212> TYPE: PRT
<213> ORGANISM: Artificial
<220> FEATURE:
<223> OTHER INFORMATION: fusion protein

<400> SEQUENCE: 95

Gln Phe His Gly Glu Lys Gly Ile Ser Ile Pro Asp His Gly Phe Cys
1               5                   10                  15
Gln Pro Ile Ser Ile Pro Leu Cys Thr Asp Ile Ala Tyr Asn Gln Thr
            20                  25                  30
Ile Met Pro Asn Leu Leu Gly His Thr Asn Gln Glu Asp Ala Gly Leu
            35                  40                  45
Glu Val His Gln Phe Tyr Pro Leu Val Lys Val Gln Cys Ser Pro Glu
            50                  55                  60
Leu Arg Phe Phe Leu Cys Ser Met Tyr Ala Pro Val Cys Thr Val Leu
65                  70                  75                  80
Glu Gln Ala Ile Pro Pro Cys Arg Ser Ile Cys Glu Arg Ala Arg Gln
            85                  90                  95
Gly Cys Glu Ala Leu Met Asn Lys Phe Gly Phe Gln Trp Pro Glu Arg
            100                 105                 110
```

Leu Arg Cys Glu His Phe Pro Arg His Gly Ala Glu Gln Ile Cys Val
            115                 120                 125

Gly Gln Asn His Ser Glu Asp Gly Ala Pro Ala Leu Leu Thr Thr Ala
        130                 135                 140

Pro Pro Pro Gly Leu Gln Pro Gly Ala Gly Thr Pro Gly Gly Pro
145                 150                 155                 160

Gly Gly Gly Ala Pro Pro Arg Tyr Ala Thr Leu Glu His Pro Phe
            165                 170                 175

His Cys Ala Glu Pro Arg Ser Ser Asp Lys Thr His Thr Cys Pro Pro
                180                 185                 190

Cys Pro Ala Pro Glu Ala Glu Gly Ala Pro Ser Val Phe Leu Phe Pro
            195                 200                 205

Pro Lys Pro Lys Asp Thr Leu Met Ile Ser Arg Thr Pro Glu Val Thr
210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Ala Val Ser
        275                 280                 285

Asn Lys Ala Leu Pro Ala Ser Ile Glu Lys Thr Ile Ser Lys Ala Lys
        290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
        370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 96
<211> LENGTH: 417
<212> TYPE: PRT
<213> ORGANISM: Artificial
<220> FEATURE:
<223> OTHER INFORMATION: fusion protein

<400> SEQUENCE: 96

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
                 85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Thr Leu Glu His Pro Phe
                165                 170                 175

His Cys Pro Arg Val Leu Lys Val Ala Glu Pro Arg Ser Ser Asp Lys
            180                 185                 190

Thr His Thr Cys Pro Pro Cys Pro Ala Pro Glu Ala Glu Gly Ala Pro
        195                 200                 205

Ser Val Phe Leu Phe Pro Pro Lys Pro Lys Asp Thr Leu Met Ile Ser
210                 215                 220

Arg Thr Pro Glu Val Thr Cys Val Val Val Asp Val Ser His Glu Asp
225                 230                 235                 240

Pro Glu Val Lys Phe Asn Trp Tyr Val Asp Gly Val Glu Val His Asn
                245                 250                 255

Ala Lys Thr Lys Pro Arg Glu Glu Gln Tyr Asn Ser Thr Tyr Arg Val
            260                 265                 270

Val Ser Val Leu Thr Val Leu His Gln Asp Trp Leu Asn Gly Lys Glu
        275                 280                 285

Tyr Lys Cys Ala Val Ser Asn Lys Ala Leu Pro Ala Ser Ile Glu Lys
290                 295                 300

Thr Ile Ser Lys Ala Lys Gly Gln Pro Arg Glu Pro Gln Val Tyr Thr
305                 310                 315                 320

Leu Pro Pro Ser Arg Asp Glu Leu Thr Lys Asn Gln Val Ser Leu Thr
                325                 330                 335

Cys Leu Val Lys Gly Phe Tyr Pro Ser Asp Ile Ala Val Glu Trp Glu
            340                 345                 350

Ser Asn Gly Gln Pro Glu Asn Asn Tyr Lys Thr Thr Pro Pro Val Leu
        355                 360                 365

Asp Ser Asp Gly Ser Phe Phe Leu Tyr Ser Lys Leu Thr Val Asp Lys
370                 375                 380

Ser Arg Trp Gln Gln Gly Asn Val Phe Ser Cys Ser Val Met His Glu
385                 390                 395                 400

Ala Leu His Asn His Tyr Thr Gln Lys Ser Leu Ser Leu Ser Pro Gly
                405                 410                 415

Lys

<210> SEQ ID NO 97
<211> LENGTH: 423
<212> TYPE: PRT
<213> ORGANISM: Artificial
<220> FEATURE:
<223> OTHER INFORMATION: fusion protein

<400> SEQUENCE: 97

-continued

```
Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Thr Leu Glu His Pro Phe
            165                 170                 175

His Cys Pro Arg Val Leu Lys Val Pro Ser Tyr Leu Ser Tyr Ala Glu
            180                 185                 190

Pro Arg Ser Ser Asp Lys Thr His Thr Cys Pro Pro Cys Pro Ala Pro
            195                 200                 205

Glu Ala Glu Gly Ala Pro Ser Val Phe Leu Phe Pro Pro Lys Pro Lys
210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255

Gly Val Glu Val His Asn Ala Lys Thr Lys Pro Arg Glu Glu Gln Tyr
            260                 265                 270

Asn Ser Thr Tyr Arg Val Val Ser Val Leu Thr Val Leu His Gln Asp
    275                 280                 285

Trp Leu Asn Gly Lys Glu Tyr Lys Cys Ala Val Ser Asn Lys Ala Leu
        290                 295                 300

Pro Ala Ser Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
    370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys
```

<210> SEQ ID NO 98
<211> LENGTH: 430
<212> TYPE: PRT
<213> ORGANISM: Artificial
<220> FEATURE:
<223> OTHER INFORMATION: fusion protein

<400> SEQUENCE: 98

```
Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu Leu Thr Thr Ala
    130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Thr Leu Glu His Pro Phe
                165                 170                 175

His Cys Pro Arg Val Leu Lys Val Pro Ser Tyr Leu Ser Tyr Lys Phe
            180                 185                 190

Leu Gly Glu Arg Asp Ala Glu Pro Arg Ser Ser Asp Lys Thr His Thr
        195                 200                 205

Cys Pro Pro Cys Pro Ala Pro Glu Ala Glu Gly Ala Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Lys Phe Asn Trp Tyr Val Asp Gly Val Glu Val His Asn Ala Lys Thr
            260                 265                 270

Lys Pro Arg Glu Glu Gln Tyr Asn Ser Thr Tyr Arg Val Val Ser Val
        275                 280                 285

Leu Thr Val Leu His Gln Asp Trp Leu Asn Gly Lys Glu Tyr Lys Cys
    290                 295                 300

Ala Val Ser Asn Lys Ala Leu Pro Ala Ser Ile Glu Lys Thr Ile Ser
305                 310                 315                 320

Lys Ala Lys Gly Gln Pro Arg Glu Pro Gln Val Tyr Thr Leu Pro Pro
                325                 330                 335

Ser Arg Asp Glu Leu Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
```

```
            355                 360                 365
Gln Pro Glu Asn Asn Tyr Lys Thr Thr Pro Val Leu Asp Ser Asp
    370                 375                 380
Gly Ser Phe Phe Leu Tyr Ser Lys Leu Thr Val Asp Lys Ser Arg Trp
385                 390                 395                 400
Gln Gln Gly Asn Val Phe Ser Cys Ser Val Met His Glu Ala Leu His
                405                 410                 415
Asn His Tyr Thr Gln Lys Ser Leu Ser Leu Ser Pro Gly Lys
            420                 425                 430

<210> SEQ ID NO 99
<211> LENGTH: 443
<212> TYPE: PRT
<213> ORGANISM: Artificial
<220> FEATURE:
<223> OTHER INFORMATION: fusion protein

<400> SEQUENCE: 99

Gln Phe His Gly Glu Lys Gly Ile Ser Ile Pro Asp His Gly Phe Cys
1               5                   10                  15
Gln Pro Ile Ser Ile Pro Leu Cys Thr Asp Ile Ala Tyr Asn Gln Thr
            20                  25                  30
Ile Met Pro Asn Leu Leu Gly His Thr Asn Gln Glu Asp Ala Gly Leu
        35                  40                  45
Glu Val His Gln Phe Tyr Pro Leu Val Lys Val Gln Cys Ser Pro Glu
    50                  55                  60
Leu Arg Phe Phe Leu Cys Ser Met Tyr Ala Pro Val Cys Thr Val Leu
65                  70                  75                  80
Glu Gln Ala Ile Pro Pro Cys Arg Ser Ile Cys Glu Arg Ala Arg Gln
                85                  90                  95
Gly Cys Glu Ala Leu Met Asn Lys Phe Gly Phe Gln Trp Pro Glu Arg
            100                 105                 110
Leu Arg Cys Glu His Phe Pro Arg His Gly Ala Glu Gln Ile Cys Val
        115                 120                 125
Gly Gln Asn His Ser Glu Asp Gly Ala Pro Ala Leu Leu Thr Thr Ala
    130                 135                 140
Pro Pro Pro Gly Leu Gln Pro Gly Ala Gly Thr Pro Gly Gly Pro
145                 150                 155                 160
Gly Gly Gly Gly Ala Pro Pro Arg Tyr Ala Thr Leu Glu His Pro Phe
                165                 170                 175
His Cys Pro Arg Val Leu Lys Val Pro Ser Tyr Leu Ser Tyr Lys Phe
            180                 185                 190
Leu Gly Glu Arg Asp Cys Ala Ala Pro Cys Glu Pro Ala Arg Pro Asp
        195                 200                 205
Gly Ser Ala Glu Pro Arg Ser Ser Asp Lys Thr His Thr Cys Pro Pro
    210                 215                 220
Cys Pro Ala Pro Glu Ala Glu Gly Ala Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
```

```
                290                 295                 300
Leu His Gln Asp Trp Leu Asn Gly Lys Glu Tyr Lys Cys Ala Val Ser
305                 310                 315                 320

Asn Lys Ala Leu Pro Ala Ser Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 100
<211> LENGTH: 449
<212> TYPE: PRT
<213> ORGANISM: Artificial
<220> FEATURE:
<223> OTHER INFORMATION: fusion protein

<400> SEQUENCE: 100

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
                35                  40                  45

Glu Val His Gln Phe Tyr Pro Leu Val Lys Val Gln Cys Ser Pro Glu
50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
                100                 105                 110

Leu Arg Cys Glu His Phe Pro Arg His Gly Ala Glu Gln Ile Cys Val
                115                 120                 125

Gly Gln Asn His Ser Glu Asp Gly Ala Pro Ala Leu Leu Thr Thr Ala
                130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Thr Leu Glu His Pro Phe
                165                 170                 175

His Cys Pro Arg Val Leu Lys Val Pro Ser Tyr Leu Ser Tyr Lys Phe
                180                 185                 190

Leu Gly Glu Arg Asp Cys Ala Ala Pro Cys Glu Pro Ala Arg Pro Asp
                195                 200                 205

Gly Ser Met Phe Phe Ser Gln Glu Ala Glu Pro Arg Ser Ser Asp Lys
```

```
                    210                 215                 220
Thr His Thr Cys Pro Pro Cys Pro Ala Pro Glu Ala Glu Gly Ala Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Ser Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Asp Glu Leu Thr Lys Asn Gln Val Ser Leu Thr
                    355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

Lys

<210> SEQ ID NO 101
<211> LENGTH: 455
<212> TYPE: PRT
<213> ORGANISM: Artificial
<220> FEATURE:
<223> OTHER INFORMATION: fusion protein

<400> SEQUENCE: 101

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
                    35                  40                  45

Glu Val His Gln Phe Tyr Pro Leu Val Lys Val Gln Cys Ser Pro Glu
        50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                    85                  90                  95

Gly Cys Glu Ala Leu Met Asn Lys Phe Gly Phe Gln Trp Pro Glu Arg
                100                 105                 110

Leu Arg Cys Glu His Phe Pro Arg His Gly Ala Glu Gln Ile Cys Val
            115                 120                 125
```

Gly Gln Asn His Ser Glu Asp Gly Ala Pro Ala Leu Leu Thr Thr Ala
            130                 135                 140

Pro Pro Pro Gly Leu Gln Pro Gly Ala Gly Thr Pro Gly Gly Pro
145                 150                 155                 160

Gly Gly Gly Gly Ala Pro Pro Arg Tyr Ala Thr Leu Glu His Pro Phe
                165                 170                 175

His Cys Pro Arg Val Leu Lys Val Pro Ser Tyr Leu Ser Tyr Lys Phe
                180                 185                 190

Leu Gly Glu Arg Asp Cys Ala Ala Pro Cys Glu Pro Ala Arg Pro Asp
            195                 200                 205

Gly Ser Met Phe Phe Ser Gln Glu Glu Thr Arg Phe Ala Arg Ala Glu
            210                 215                 220

Pro Arg Ser Ser Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Ala Val Ser Asn Lys Ala Leu
                325                 330                 335

Pro Ala Ser Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 102
<211> LENGTH: 112
<212> TYPE: PRT
<213> ORGANISM: Homo sapiens

<400> SEQUENCE: 102

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
                20                  25                  30

Leu Glu Val His Gln Phe Tyr Pro Leu Val Lys Val Gln Cys Ser Pro

```
                    35                  40                  45
Glu Leu Arg Phe Phe Leu Cys Ser Met Tyr Ala Pro Val Cys Thr Val
    50                  55                  60

Leu Glu Gln Ala Ile Pro Pro Cys Arg Ser Ile Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu His Phe Pro Arg His Gly Ala Glu Gln Ile Cys
                100                 105                 110

<210> SEQ ID NO 103
<211> LENGTH: 336
<212> TYPE: DNA
<213> ORGANISM: Homo sapiens

<400> SEQUENCE: 103
tgccagccca tctccatccc gctgtgcacg gacatcgcct acaaccagac catcatgccc        60
aaccttctgg gccacacgaa ccaggaggac gcaggcctag aggtgcacca gttctatccg       120
ctggtgaagg tgcagtgctc gcccgaactg cgcttcttcc tgtgctccat gtacgcaccc       180
gtgtgcaccg tgctggaaca ggccatcccg ccgtgccgct ctatctgtga gcgcgcgcgc       240
cagggctgcg aagccctcat gaacaagttc ggttttcagt ggcccgagcg cctgcgctgc       300
gagcacttcc cgcgccacgg cgccgagcag atctgc                                 336
```